(12) United States Patent
Capell et al.

(10) Patent No.: US 10,671,705 B2
(45) Date of Patent: Jun. 2, 2020

(54) CUSTOMIZING RECIPE RECOMMENDATIONS

(71) Applicant: ICON Health & Fitness, Inc., Logan, UT (US)

(72) Inventors: Rebecca Lynn Capell, Logan, UT (US); Megan Jane Ostler, North Logan, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 253 days.

(21) Appl. No.: 15/712,682

(22) Filed: Sep. 22, 2017

(65) Prior Publication Data

US 2018/0089396 A1 Mar. 29, 2018

Related U.S. Application Data

(60) Provisional application No. 62/400,773, filed on Sep. 28, 2016.

(51) Int. Cl.
*G09B 19/00* (2006.01)
*G06F 19/00* (2018.01)
(Continued)

(52) U.S. Cl.
CPC ............ *G06F 19/3475* (2013.01); *A61B 5/22* (2013.01); *A63B 24/0062* (2013.01);
(Continued)

(58) Field of Classification Search
CPC .................................................. G06F 19/3475
(Continued)

(56) References Cited

U.S. PATENT DOCUMENTS 321,388 A   6/1885   Ruebsam
348,493 A   8/1886   Greene
(Continued)

FOREIGN PATENT DOCUMENTS

KR   10-2016-0040699   4/2016
KR   10-2016-0054325   5/2016
(Continued)

OTHER PUBLICATIONS

International Search Report issued for PCT/US2017/053273 dated Dec. 11, 2017.
(Continued)

*Primary Examiner* — Kesha Frisby
(74) *Attorney, Agent, or Firm* — Maschoff Brennan

(57) ABSTRACT

A method for customizing recipe recommendations may include receiving a target number of calories for a user, receiving physical movement data of the user from one or more electronic sensors configured to directly measure physical movement of the user, analyzing the received physical movement data, determining one or more physical movement parameters based on the analysis of the received physical movement data, determining the recentness of each of the recipes being recommended or logged to the user, assigning a weight to each of the recipes based on the received target number of calories for the user, the determined one or more physical movement parameters, and the determined recentness of the recipe being recommended or logged to the user, ranking the recipes based on their assigned weights, and generating a custom recipe recommendation for the user based on the ranking of the recipes.

20 Claims, 5 Drawing Sheets

(51) Int. Cl.
  *A61B 5/22* (2006.01)
  *A63B 24/00* (2006.01)
  *G16H 20/60* (2018.01)
  *G16H 40/67* (2018.01)

(52) U.S. Cl.
  CPC ..... *G06F 19/3481* (2013.01); *G09B 19/0092* (2013.01); *G16H 20/60* (2018.01); *G16H 40/67* (2018.01)

(58) Field of Classification Search
  USPC .......................................................... 434/127
  See application file for complete search history.

(56) References Cited

U.S. PATENT DOCUMENTS

| | | |
|---|---|---|
| 470,837 A | 3/1892 | Hart |
| 549,084 A | 10/1895 | Whitaker |
| 601,307 A | 3/1898 | Salisbury |
| 663,486 A | 12/1900 | Boren |
| 881,521 A | 3/1908 | Wilson |
| 1,020,777 A | 3/1912 | Peterson |
| 1,082,940 A | 12/1913 | Flora |
| 1,715,870 A | 6/1929 | Spain |
| 1,850,530 A | 3/1932 | Brown |
| 1,902,694 A | 3/1933 | Edwards |
| 1,928,089 A | 9/1933 | Blickman |
| 1,930,416 A | 10/1933 | Chauvot |
| 1,973,945 A | 9/1934 | Chavin |
| 2,413,841 A | 1/1947 | Minuto |
| 2,779,139 A | 1/1957 | Boettcher |
| 2,855,200 A | 10/1958 | Blickman |
| 2,874,971 A | 2/1959 | Devery |
| 2,906,532 A | 9/1959 | Echols |
| 3,127,171 A | 3/1964 | Noland et al. |
| 3,378,259 A | 4/1968 | Kupchinski |
| 3,394,934 A | 7/1968 | Petros |
| 3,408,067 A | 10/1968 | Armstrong |
| 3,424,005 A | 1/1969 | Brown |
| 3,432,164 A | 3/1969 | Deeks |
| 3,518,985 A | 7/1970 | Quinton |
| 3,589,715 A | 6/1971 | Mark |
| 3,592,466 A | 7/1971 | Parsons |
| 3,602,502 A | 8/1971 | Jaegar |
| 3,614,097 A | 10/1971 | Blickman |
| 3,659,845 A | 5/1972 | Quinton |
| 3,728,940 A | 4/1973 | Peterson |
| 3,731,917 A | 5/1973 | Townsend |
| 3,738,649 A | 6/1973 | Miller |
| 3,741,538 A | 6/1973 | Useldinger |
| 3,744,480 A | 7/1973 | Nasa |
| 3,744,712 A | 7/1973 | Papadopoulos |
| 3,744,794 A | 7/1973 | Nasa |
| 3,751,033 A | 8/1973 | Rosenthal |
| 3,767,195 A | 10/1973 | Dimick |
| 3,782,718 A | 1/1974 | Saylor |
| 3,802,698 A | 4/1974 | Burian et al. |
| 3,818,194 A | 6/1974 | Biro |
| 3,822,599 A | 7/1974 | Brentham |
| 3,826,491 A | 7/1974 | Elder |
| 3,834,696 A | 9/1974 | Spector |
| 3,845,756 A | 11/1974 | Olsson |
| 3,851,874 A | 12/1974 | Wilkin |
| 3,858,938 A | 1/1975 | Kristensson et al. |
| 3,859,840 A | 1/1975 | Nasa |
| 3,874,657 A | 4/1975 | Niebojewski |
| 3,892,404 A | 7/1975 | Martucci |
| 3,902,480 A | 9/1975 | Wilson |
| 3,903,613 A | 9/1975 | Bisberg |
| 3,974,491 A | 8/1976 | Sipe |
| 4,020,795 A | 5/1977 | Marks |
| 4,026,545 A | 5/1977 | Schonenberger |
| 4,027,531 A | 6/1977 | Dawson |
| 4,066,257 A | 1/1978 | Moller |
| 4,071,235 A | 1/1978 | Zent |
| 4,082,267 A | 4/1978 | Flavell |
| 4,112,928 A | 9/1978 | Putsch |
| 4,120,294 A | 10/1978 | Wolfe |
| 4,120,924 A | 10/1978 | Rainville |
| 4,151,988 A | 5/1979 | Nabinger |
| 4,204,673 A | 5/1980 | Speer, Sr. |
| 4,220,996 A | 9/1980 | Searcy |
| 4,236,239 A | 11/1980 | Imgruth et al. |
| 4,239,092 A | 12/1980 | Janson |
| 4,248,476 A | 2/1981 | Phelps |
| 4,274,625 A | 6/1981 | Gaetano |
| 4,278,095 A | 7/1981 | Lapeyre |
| 4,278,249 A | 7/1981 | Forrest |
| 4,298,893 A | 11/1981 | Holmes |
| 4,300,761 A | 11/1981 | Howard |
| 4,301,808 A | 11/1981 | Taus |
| 4,322,609 A | 3/1982 | Kato |
| 4,323,237 A | 4/1982 | Jungerwirth |
| 4,337,529 A | 6/1982 | Morokawa |
| 4,354,676 A | 10/1982 | Ariel |
| 4,355,645 A | 10/1982 | Mitani et al. |
| 4,358,105 A | 11/1982 | Sweeney, Jr. |
| 4,378,111 A | 3/1983 | Tsuchida et al. |
| 4,383,714 A | 5/1983 | Ishida |
| 4,389,047 A | 6/1983 | Hall |
| 4,408,613 A | 10/1983 | Relyea |
| 4,422,635 A | 12/1983 | Herod |
| 4,423,630 A | 1/1984 | Morrison |
| 4,423,864 A | 1/1984 | Wiik |
| 4,480,831 A | 11/1984 | Muller-Deinhardt |
| 4,493,561 A | 1/1985 | Bouchet |
| 4,495,560 A | 1/1985 | Sugimoto et al. |
| 4,504,055 A | 3/1985 | Wells |
| 4,504,968 A | 3/1985 | Kaneko et al. |
| 4,512,566 A | 4/1985 | Bicocchi |
| 4,512,567 A | 4/1985 | Phillips |
| 4,515,988 A | 5/1985 | Bayer et al. |
| 4,519,603 A | 5/1985 | Decloux |
| 4,529,196 A | 7/1985 | Logan |
| 4,533,136 A | 8/1985 | Smith et al. |
| 4,537,396 A | 8/1985 | Hooper |
| 4,542,897 A | 9/1985 | Melton |
| 4,544,152 A | 10/1985 | Taitel |
| 4,549,044 A | 10/1985 | Durham |
| 4,555,108 A | 11/1985 | Monteiro |
| 4,556,216 A | 12/1985 | Pitkanen |
| 4,566,461 A | 1/1986 | Lubell et al. |
| 4,569,518 A | 2/1986 | Fulks |
| 4,571,682 A | 2/1986 | Silverman et al. |
| 4,573,449 A | 3/1986 | Warnke |
| 4,577,860 A | 3/1986 | Matias et al. |
| 4,577,865 A | 3/1986 | Shishido |
| 4,586,495 A | 5/1986 | Petrofsky |
| 4,591,147 A | 5/1986 | Smith et al. |
| 4,592,544 A | 6/1986 | Smith et al. |
| 4,602,779 A | 7/1986 | Ogden |
| 4,625,962 A | 12/1986 | Street |
| 4,630,817 A | 12/1986 | Buckley |
| 4,634,127 A | 1/1987 | Rockwell |
| 4,635,928 A | 1/1987 | Ogden et al. |
| 4,637,605 A | 1/1987 | Ritchie |
| 4,642,769 A | 2/1987 | Petrofsky |
| 4,643,418 A | 2/1987 | Bart |
| 4,647,037 A | 3/1987 | Donohue |
| 4,651,446 A | 3/1987 | Yukawa et al. |
| 4,659,074 A | 4/1987 | Taitel et al. |
| 4,659,078 A | 4/1987 | Blome |
| 4,664,646 A | 5/1987 | Rorabaugh |
| 4,665,388 A | 5/1987 | Ivie et al. |
| 4,671,257 A | 6/1987 | Kaiser et al. |
| 4,678,182 A | 7/1987 | Nakao et al. |
| 4,679,786 A | 7/1987 | Rodgers |
| 4,679,787 A | 7/1987 | Guilbault |
| 4,687,195 A | 8/1987 | Potts |
| 4,702,475 A | 10/1987 | Elstein et al. |
| 4,708,337 A | 11/1987 | Shyu |
| 4,708,338 A | 11/1987 | Potts |
| 4,708,837 A | 11/1987 | Baxter et al. |
| 4,709,917 A | 12/1987 | Yang |

(56) References Cited

U.S. PATENT DOCUMENTS

| | | |
|---|---|---|
| 4,709,918 A | 12/1987 | Grinblat |
| 4,711,447 A | 12/1987 | Mansfield |
| 4,714,244 A | 12/1987 | Kolomayets et al. |
| 4,720,099 A | 1/1988 | Carlson |
| 4,720,789 A | 1/1988 | Hector et al. |
| 4,726,581 A | 2/1988 | Chang |
| 4,726,582 A | 2/1988 | Fulks |
| 4,728,099 A | 3/1988 | Pitre |
| 4,729,558 A | 3/1988 | Kuo |
| 4,730,828 A | 3/1988 | Lane |
| 4,730,829 A | 3/1988 | Carlson |
| 4,743,009 A | 5/1988 | Beale |
| 4,750,738 A | 6/1988 | Dang |
| 4,757,495 A | 7/1988 | Decker et al. |
| 4,759,540 A | 7/1988 | Yu et al. |
| 4,763,284 A | 8/1988 | Carlin |
| 4,765,613 A | 8/1988 | Voris |
| 4,770,411 A | 9/1988 | Armstrong et al. |
| 4,771,148 A | 9/1988 | Bersonnet |
| 4,771,577 A | 9/1988 | Abe |
| 4,774,679 A | 9/1988 | Carlin |
| 4,776,582 A | 10/1988 | Ramhorst |
| 4,786,049 A | 11/1988 | Lautenschlager |
| 4,786,050 A | 11/1988 | Geschwender |
| 4,789,153 A | 12/1988 | Brown |
| 4,790,522 A | 12/1988 | Drutchas |
| 4,790,528 A | 12/1988 | Nakao et al. |
| 4,798,377 A | 1/1989 | White |
| 4,805,901 A | 2/1989 | Kulick |
| 4,813,665 A | 3/1989 | Carr |
| 4,813,743 A | 3/1989 | Mizelle |
| 4,814,661 A | 3/1989 | Ratzlaff et al. |
| 4,817,938 A | 4/1989 | Nakao et al. |
| 4,817,939 A | 4/1989 | Augspurger et al. |
| 4,817,940 A | 4/1989 | Shaw et al. |
| 4,818,234 A | 4/1989 | Redington |
| 4,819,818 A | 4/1989 | Simkus |
| 4,824,104 A | 4/1989 | Bloch |
| 4,826,153 A | 5/1989 | Schalip |
| 4,828,257 A | 5/1989 | Dyer et al. |
| 4,828,522 A | 5/1989 | Santos |
| 4,828,713 A | 5/1989 | McDonald et al. |
| 4,830,363 A | 5/1989 | Kennedy |
| 4,832,332 A | 5/1989 | Dumbser |
| 4,837,157 A | 6/1989 | Turnell et al. |
| 4,838,543 A | 6/1989 | Armstrong et al. |
| 4,840,372 A | 6/1989 | Oglesby et al. |
| 4,842,266 A | 6/1989 | Sweeney, Sr. |
| 4,842,274 A | 6/1989 | Oosthuizen |
| 4,844,449 A | 7/1989 | Truslaske |
| 4,844,450 A | 7/1989 | Rodgers, Jr. |
| 4,846,693 A | 7/1989 | Baer |
| 4,848,737 A | 7/1989 | Ehrenfield |
| 4,855,942 A | 8/1989 | Bianco |
| 4,860,763 A | 8/1989 | Schminke |
| 4,863,157 A | 9/1989 | Mendel et al. |
| 4,866,704 A | 9/1989 | Bergman |
| 4,867,442 A | 9/1989 | Matthews |
| 4,869,497 A | 9/1989 | Stewart et al. |
| 4,889,108 A | 12/1989 | Bond et al. |
| 4,889,131 A | 12/1989 | Salem et al. |
| 4,891,785 A | 1/1990 | Donohoo |
| 4,900,013 A | 2/1990 | Rodgers, Jr. |
| 4,904,829 A | 2/1990 | Berthaud et al. |
| 4,905,330 A | 3/1990 | Jacobs |
| 4,907,795 A | 3/1990 | Shaw et al. |
| 4,907,973 A | 3/1990 | Hon |
| 4,911,427 A | 3/1990 | Matsumoto et al. |
| 4,912,638 A | 3/1990 | Pratt, Jr. |
| 4,913,396 A | 4/1990 | Dalebout et al. |
| 4,913,423 A | 4/1990 | Farran |
| 4,919,418 A | 4/1990 | Miller |
| 4,921,247 A | 5/1990 | Sterling |
| 4,925,183 A | 5/1990 | Kim |
| 4,925,189 A | 5/1990 | Braeunig |
| 4,927,136 A | 5/1990 | Leask |
| 4,930,770 A | 6/1990 | Baker |
| 4,934,692 A | 6/1990 | Owens |
| 4,934,694 A | 6/1990 | Mcintosh |
| 4,938,469 A | 7/1990 | Crandell |
| 4,938,474 A | 7/1990 | Sweeney et al. |
| 4,949,993 A | 8/1990 | Stark et al. |
| 4,959,713 A | 9/1990 | Morotomi et al. |
| 4,976,424 A | 12/1990 | Sargeant et al. |
| 4,976,435 A | 12/1990 | Shatford |
| 4,983,847 A | 1/1991 | Bryan |
| 4,986,534 A | 1/1991 | Meier et al. |
| 4,986,689 A | 1/1991 | Drutchas |
| 4,992,190 A | 2/1991 | Shtarkman |
| 4,998,725 A | 3/1991 | Watterson et al. |
| 5,000,440 A | 3/1991 | Lynch |
| 5,001,632 A | 3/1991 | Hall Tipping |
| 5,002,271 A | 3/1991 | Gonzales |
| 5,015,926 A | 5/1991 | Casler |
| 5,020,794 A | 6/1991 | Englehardt et al. |
| 5,020,795 A | 6/1991 | Airy et al. |
| 5,027,303 A | 6/1991 | Witte |
| 5,029,801 A | 7/1991 | Dalebout et al. |
| 5,031,455 A | 7/1991 | Cline |
| 5,034,576 A | 7/1991 | Dalebout et al. |
| 5,035,418 A | 7/1991 | Harabayashi |
| RE33,662 E | 8/1991 | Blair et al. |
| 5,037,089 A | 8/1991 | Spagnuolo |
| 5,039,088 A | 8/1991 | Shifferaw |
| 5,039,089 A | 8/1991 | Lapcevic |
| 5,039,091 A | 8/1991 | Johnson |
| 5,046,382 A | 9/1991 | Steinberg |
| 5,052,375 A | 10/1991 | Stark |
| 5,052,684 A | 10/1991 | Kosuge et al. |
| 5,054,774 A | 10/1991 | Chattecx |
| 5,062,632 A | 11/1991 | Dalebout et al. |
| 5,067,710 A | 11/1991 | Watterson et al. |
| 5,078,152 A | 1/1992 | Bond et al. |
| 5,086,385 A | 2/1992 | Launey et al. |
| 5,088,729 A | 2/1992 | Dalebout |
| 5,089,960 A | 2/1992 | Sweeney, Jr. |
| 5,104,119 A | 4/1992 | Lynch |
| 5,104,120 A | 4/1992 | Watterson et al. |
| 5,109,778 A | 5/1992 | Berkowitz et al. |
| 5,113,427 A | 5/1992 | Ryoichi et al. |
| 5,114,391 A | 5/1992 | Pitzen et al. |
| 5,117,674 A | 6/1992 | Howard |
| 5,118,112 A | 6/1992 | Bregman et al. |
| 5,137,501 A | 8/1992 | Mertesdorf |
| 5,142,358 A | 8/1992 | Jason |
| 5,145,475 A | 9/1992 | Cares |
| 5,145,481 A | 9/1992 | Friedebach |
| 5,149,084 A | 9/1992 | Dalebout et al. |
| 5,152,210 A | 10/1992 | Chen |
| 5,158,093 A | 10/1992 | Shvartz |
| 5,162,029 A | 11/1992 | Schine |
| 5,167,159 A | 12/1992 | Lucking |
| 5,167,850 A | 12/1992 | Shtarkman |
| 5,171,196 A | 12/1992 | Lynch |
| 5,176,602 A | 1/1993 | Roberts |
| 5,180,347 A | 1/1993 | Chen |
| 5,180,351 A | 1/1993 | Ehrenfried |
| 5,180,647 A | 1/1993 | Rowland et al. |
| 5,186,471 A | 2/1993 | Vancraeynest |
| 5,192,255 A | 3/1993 | Dalebout et al. |
| 5,192,257 A | 3/1993 | Panasewicz |
| 5,195,935 A | 3/1993 | Fencel |
| 5,201,772 A | 4/1993 | Maxwell |
| 5,202,424 A | 4/1993 | Vlassara et al. |
| 5,204,670 A | 4/1993 | Stinton |
| 5,205,800 A | 4/1993 | Grant |
| 5,206,671 A | 4/1993 | Eydelman et al. |
| 5,207,628 A | 5/1993 | Graham |
| 5,213,555 A | 5/1993 | Hood |
| 5,226,866 A | 7/1993 | Engel et al. |
| 5,230,672 A | 7/1993 | Brown et al. |
| 5,230,673 A | 7/1993 | Maeyama et al. |
| 5,233,520 A | 8/1993 | Kretsch et al. |
| 5,234,392 A | 8/1993 | Clark |

(56) References Cited

U.S. PATENT DOCUMENTS

| | | |
|---|---|---|
| 5,234,395 A | 8/1993 | Miller et al. |
| 5,240,417 A | 8/1993 | Smithson et al. |
| 5,243,998 A | 9/1993 | Silverman et al. |
| 5,246,411 A | 9/1993 | Rackman |
| 5,254,066 A | 10/1993 | Brown et al. |
| 5,256,115 A | 10/1993 | Scholder |
| 5,257,084 A | 10/1993 | Marsh |
| 5,260,870 A | 11/1993 | Tsuchiya et al. |
| 5,261,864 A | 11/1993 | Fitzpatrick |
| 5,267,925 A | 12/1993 | Boyd |
| 5,269,081 A | 12/1993 | Gray |
| 5,269,519 A | 12/1993 | Malone |
| 5,277,678 A | 1/1994 | Friedebach et al. |
| 5,290,205 A | 3/1994 | Densmore et al. |
| 5,292,293 A | 3/1994 | Schumacher |
| 5,299,810 A | 4/1994 | Pierce et al. |
| 5,301,154 A | 4/1994 | Suga |
| 5,306,220 A | 4/1994 | Kearney |
| 5,308,296 A | 5/1994 | Eckstein |
| 5,308,300 A | 5/1994 | Chino et al. |
| 5,309,355 A | 5/1994 | Lockwood |
| 5,313,942 A | 5/1994 | Platzker |
| 5,314,389 A | 5/1994 | Dotan |
| 5,314,391 A | 5/1994 | Potash et al. |
| 5,316,534 A | 5/1994 | Dalebout et al. |
| 5,318,487 A | 6/1994 | Golen et al. |
| 5,318,491 A | 6/1994 | Houston |
| 5,323,650 A | 6/1994 | Fullen et al. |
| 5,323,784 A | 6/1994 | Shu |
| 5,328,420 A | 7/1994 | Allen |
| 5,328,422 A | 7/1994 | Nichols |
| 5,335,188 A | 8/1994 | Brisson |
| 5,336,146 A | 8/1994 | Piaget et al. |
| RE34,728 E | 9/1994 | Hall-Tipping |
| 5,352,166 A | 10/1994 | Chang |
| 5,352,167 A | 10/1994 | Ulicny |
| 5,354,251 A | 10/1994 | Sleamaker |
| 5,357,696 A | 10/1994 | Gray |
| 5,358,461 A | 10/1994 | Bailey, Jr. |
| 5,361,091 A | 11/1994 | Hoarty et al. |
| 5,361,778 A | 11/1994 | Seitz |
| 5,362,069 A | 11/1994 | Hall-Tipping |
| 5,362,298 A | 11/1994 | Brown et al. |
| 5,364,271 A | 11/1994 | Aknin et al. |
| 5,368,532 A | 11/1994 | Farnet |
| 5,372,564 A | 12/1994 | Spirito |
| 5,375,068 A | 12/1994 | Palmer et al. |
| 5,377,171 A | 12/1994 | Schlup |
| 5,377,258 A | 12/1994 | Bro |
| 5,382,207 A | 1/1995 | Skowronski et al. |
| 5,382,209 A | 1/1995 | Pasier |
| 5,383,827 A | 1/1995 | Stern |
| 5,385,519 A | 1/1995 | Hsu |
| 5,385,520 A | 1/1995 | Lepine et al. |
| 5,387,164 A | 2/1995 | Brown, Jr. |
| 5,391,080 A | 2/1995 | Bernacki |
| 5,396,340 A | 3/1995 | Ishii et al. |
| 5,403,252 A | 4/1995 | Leon et al. |
| 5,407,402 A | 4/1995 | Brown et al. |
| 5,409,435 A | 4/1995 | Daniels |
| 5,410,471 A | 4/1995 | Alyfuku et al. |
| 5,410,472 A | 4/1995 | Anderson |
| 5,417,222 A | 5/1995 | Dempsey et al. |
| 5,417,643 A | 5/1995 | Taylor |
| 5,419,562 A | 5/1995 | Cromarty |
| 5,421,801 A | 6/1995 | Davies, III et al. |
| 5,431,612 A | 7/1995 | Holden |
| 5,433,679 A | 7/1995 | Szymczak et al. |
| 5,435,799 A | 7/1995 | Lundin |
| 5,437,289 A | 8/1995 | Liverance |
| 5,445,583 A | 8/1995 | Habing |
| 5,451,922 A | 9/1995 | Hamilton |
| 5,452,269 A | 9/1995 | Cherdak |
| 5,454,772 A | 10/1995 | Rodden |
| 5,456,262 A | 10/1995 | Birnbaum |
| 5,456,648 A | 10/1995 | Edinburg |
| 5,462,051 A | 10/1995 | Oka et al. |
| 5,462,503 A | 10/1995 | Benjamin et al. |
| 5,462,504 A | 10/1995 | Trulaske et al. |
| 5,466,200 A | 11/1995 | Ulrich et al. |
| 5,469,740 A | 11/1995 | French et al. |
| 5,472,205 A | 12/1995 | Bouton |
| 5,474,077 A | 12/1995 | Suga |
| 5,474,090 A | 12/1995 | Begun et al. |
| 5,476,428 A | 12/1995 | Potash et al. |
| 5,476,430 A | 12/1995 | Lee et al. |
| 5,478,295 A | 12/1995 | Fracchia |
| 5,482,472 A | 1/1996 | Garoni et al. |
| 5,484,362 A | 1/1996 | Skowronski et al. |
| 5,484,389 A | 1/1996 | Stark |
| 5,486,001 A | 1/1996 | Baker |
| 5,489,249 A | 2/1996 | Brewer et al. |
| 5,493,127 A | 2/1996 | Lloyd et al. |
| 5,499,956 A | 3/1996 | Habing et al. |
| 5,510,828 A | 4/1996 | Lutterbach |
| 5,512,025 A | 4/1996 | Dalebout et al. |
| 5,512,029 A | 4/1996 | Barnard |
| 5,516,334 A | 5/1996 | Easton |
| 5,518,471 A | 5/1996 | Hettinger et al. |
| 5,519,189 A | 5/1996 | Gibisch |
| 5,520,599 A | 5/1996 | Chen |
| 5,524,110 A | 6/1996 | Danneels et al. |
| 5,524,637 A | 6/1996 | Erickson |
| 5,527,239 A | 6/1996 | Abbondanza |
| 5,527,245 A | 6/1996 | Dalebout et al. |
| 5,535,664 A | 7/1996 | Rokowski |
| 5,538,486 A | 7/1996 | France et al. |
| 5,542,420 A | 8/1996 | Goldman |
| 5,542,672 A | 8/1996 | Meredith |
| 5,547,439 A | 8/1996 | Rawls et al. |
| 5,569,120 A | 10/1996 | Anjanappa et al. |
| 5,572,643 A | 11/1996 | Judson |
| 5,576,951 A | 11/1996 | Lockwood |
| 5,577,186 A | 11/1996 | Mann, II et al. |
| 5,577,981 A | 11/1996 | Jarvik |
| 5,577,985 A | 11/1996 | Miller |
| 5,580,249 A | 12/1996 | Jacobsen et al. |
| 5,582,563 A | 12/1996 | Fan |
| 5,584,700 A | 12/1996 | Feldman et al. |
| 5,584,779 A | 12/1996 | Knecht |
| 5,584,784 A | 12/1996 | Wu |
| 5,585,561 A | 12/1996 | Bahl et al. |
| 5,585,583 A | 12/1996 | Owen |
| 5,586,962 A | 12/1996 | Hallmark |
| 5,590,128 A | 12/1996 | Maloney et al. |
| 5,590,181 A | 12/1996 | Hogan et al. |
| 5,591,104 A | 1/1997 | Andrus et al. |
| 5,591,908 A | 1/1997 | Reid |
| 5,598,849 A | 2/1997 | Browne |
| 5,600,310 A | 2/1997 | Whipple, III et al. |
| 5,605,336 A | 2/1997 | Gaoiran |
| 5,613,216 A | 3/1997 | Galler |
| 5,618,245 A | 4/1997 | Trulaske et al. |
| 5,618,250 A | 4/1997 | Butz |
| 5,619,412 A | 4/1997 | Hapka |
| 5,619,991 A | 4/1997 | Sloane |
| 5,626,539 A | 5/1997 | Piaget |
| 5,638,343 A | 6/1997 | Ticknor |
| 5,643,142 A | 7/1997 | Salerno et al. |
| 5,643,146 A | 7/1997 | Stark et al. |
| 5,643,147 A | 7/1997 | Huang |
| 5,645,509 A | 7/1997 | Brewer et al. |
| 5,645,513 A | 7/1997 | Haydocy et al. |
| 5,652,304 A | 7/1997 | Calderon et al. |
| 5,652,824 A | 7/1997 | Hirayama et al. |
| 5,655,945 A | 8/1997 | Jani |
| 5,655,997 A | 8/1997 | Greenberg et al. |
| 5,659,691 A | 8/1997 | Durward et al. |
| 5,662,557 A | 9/1997 | Watterson et al. |
| 5,665,031 A | 9/1997 | Hsieh |
| 5,667,459 A | 9/1997 | Su |
| 5,669,833 A | 9/1997 | Stone |
| 5,672,140 A | 9/1997 | Watterson et al. |
| 5,674,156 A | 10/1997 | Watterson et al. |

(56) References Cited

U.S. PATENT DOCUMENTS

| | | |
|---|---|---|
| 5,674,453 A | 10/1997 | Watterson et al. |
| 5,676,138 A | 10/1997 | Zawilinski |
| 5,676,624 A | 10/1997 | Watterson et al. |
| 5,685,804 A | 11/1997 | Whan-Tong et al. |
| 5,690,582 A | 11/1997 | Ulrich et al. |
| 5,690,852 A | 11/1997 | Saito et al. |
| 5,693,004 A | 12/1997 | Carlson et al. |
| 5,695,400 A | 12/1997 | Fennell, Jr. et al. |
| 5,697,834 A | 12/1997 | Heumann et al. |
| 5,702,323 A | 12/1997 | Poulton |
| 5,704,875 A | 1/1998 | Tanabe |
| 5,704,879 A | 1/1998 | Watterson et al. |
| 5,710,884 A | 1/1998 | Dedrick |
| 5,711,746 A | 1/1998 | Carlson |
| 5,713,794 A | 2/1998 | Shimojima et al. |
| 5,719,825 A | 2/1998 | Dotter |
| 5,720,771 A | 2/1998 | Snell |
| 5,721,539 A | 2/1998 | Goetzl |
| 5,722,418 A | 3/1998 | Bro |
| 5,722,420 A | 3/1998 | Lee |
| 5,724,025 A | 3/1998 | Tavori |
| 5,733,228 A | 3/1998 | Stevens |
| 5,734,625 A | 3/1998 | Kondo |
| 5,738,612 A | 4/1998 | Tsuda |
| 5,739,457 A | 4/1998 | Devecka |
| 5,741,205 A | 4/1998 | Doll et al. |
| 5,743,833 A | 4/1998 | Watterson et al. |
| 5,743,835 A | 4/1998 | Trotter |
| 5,749,372 A | 5/1998 | Allen |
| 5,749,807 A | 5/1998 | Webb |
| 5,749,809 A | 5/1998 | Lin |
| 5,752,883 A | 5/1998 | Butcher et al. |
| 5,752,897 A | 5/1998 | Skowronski et al. |
| 5,754,765 A | 5/1998 | Danneels et al. |
| 5,755,645 A | 5/1998 | Miller et al. |
| 5,759,199 A | 6/1998 | Snell et al. |
| 5,760,353 A | 6/1998 | Rapp |
| 5,762,503 A | 6/1998 | Hoo et al. |
| 5,769,755 A | 6/1998 | Henry et al. |
| 5,769,759 A | 6/1998 | Alter |
| 5,771,354 A | 6/1998 | Crawford |
| 5,772,508 A | 6/1998 | Sugita et al. |
| 5,777,678 A | 7/1998 | Ogata et al. |
| 5,779,596 A | 7/1998 | Weber |
| 5,782,639 A | 7/1998 | Beal |
| 5,785,630 A | 7/1998 | Bobick et al. |
| 5,785,631 A | 7/1998 | Heidecke |
| 5,785,632 A | 7/1998 | Greenberg et al. |
| 5,790,785 A | 8/1998 | Klug et al. |
| 5,794,210 A | 8/1998 | Goldhaber et al. |
| 5,797,805 A | 8/1998 | Lubell et al. |
| 5,799,281 A | 8/1998 | Login et al. |
| 5,803,870 A | 9/1998 | Buhler |
| 5,810,696 A | 9/1998 | Webb |
| 5,810,747 A | 9/1998 | Brudny et al. |
| 5,813,142 A | 9/1998 | Demon |
| 5,813,864 A | 9/1998 | Ikuta |
| 5,813,945 A | 9/1998 | Bernacki |
| 5,813,947 A | 9/1998 | Densmore |
| 5,816,372 A | 10/1998 | Carlson et al. |
| 5,816,443 A | 10/1998 | Bustos |
| 5,820,525 A | 10/1998 | Riley |
| 5,823,913 A | 10/1998 | Aruin |
| 5,825,983 A | 10/1998 | Park et al. |
| 5,827,154 A | 10/1998 | Gill |
| 5,827,155 A | 10/1998 | Jensen et al. |
| 5,830,107 A | 11/1998 | Brigliadoro |
| 5,830,113 A | 11/1998 | Coody et al. |
| 5,833,577 A | 11/1998 | Hurt |
| 5,833,583 A | 11/1998 | Chuang |
| 5,836,770 A | 11/1998 | Powers |
| 5,838,906 A | 11/1998 | Doyle et al. |
| 5,839,990 A | 11/1998 | Virkkala |
| 5,845,230 A | 12/1998 | Lamberson |
| 5,848,396 A | 12/1998 | Gerace |
| 5,854,833 A | 12/1998 | Hogan et al. |
| 5,855,537 A | 1/1999 | Coody et al. |
| 5,855,538 A | 1/1999 | Argabright |
| 5,857,939 A | 1/1999 | Kaufman |
| 5,860,893 A | 1/1999 | Watterson et al. |
| 5,864,018 A | 1/1999 | Morser et al. |
| 5,865,733 A | 2/1999 | Malinouskas et al. |
| 5,868,648 A | 2/1999 | Coody et al. |
| 5,873,369 A | 2/1999 | Laniado et al. |
| 5,876,095 A | 3/1999 | Johnston |
| 5,879,270 A | 3/1999 | Huish et al. |
| 5,880,677 A | 3/1999 | Lestician |
| 5,888,172 A | 3/1999 | Andrus et al. |
| 5,890,149 A | 3/1999 | Schmonsees |
| 5,890,906 A | 4/1999 | Macri |
| 5,890,995 A | 4/1999 | Bobick et al. |
| 5,890,996 A | 4/1999 | Frame et al. |
| 5,890,997 A | 4/1999 | Roth |
| 5,891,042 A | 4/1999 | Sham et al. |
| 5,897,463 A | 4/1999 | Maresh |
| 5,899,833 A | 5/1999 | Ryan et al. |
| 5,899,834 A | 5/1999 | Dalebout et al. |
| 5,899,963 A | 5/1999 | Hutchings |
| 5,902,214 A | 5/1999 | Makikawa et al. |
| 5,905,442 A | 5/1999 | Mosebrook et al. |
| 5,906,494 A | 5/1999 | Ogawa et al. |
| 5,906,581 A | 5/1999 | Tsuda |
| 5,909,544 A | 6/1999 | Anderson, II et al. |
| 5,910,070 A | 6/1999 | Henry et al. |
| 5,911,044 A | 6/1999 | Lo et al. |
| 5,911,132 A | 6/1999 | Sloane |
| 5,911,687 A | 6/1999 | Sato et al. |
| 5,913,310 A | 6/1999 | Brown |
| 5,913,830 A | 6/1999 | Miles |
| 5,916,063 A | 6/1999 | Alessandri |
| 5,916,065 A | 6/1999 | McBride et al. |
| 5,917,405 A | 6/1999 | Joao |
| 5,919,117 A | 7/1999 | Thompson et al. |
| 5,921,891 A | 7/1999 | Browne |
| 5,921,896 A | 7/1999 | Boland |
| 5,929,748 A | 7/1999 | Odinak |
| 5,929,782 A | 7/1999 | Stark |
| 5,929,848 A | 7/1999 | Albukerk et al. |
| 5,931,763 A | 8/1999 | Alessandri |
| 5,937,387 A | 8/1999 | Summerell et al. |
| 5,938,571 A | 8/1999 | Stevens |
| 5,941,797 A | 8/1999 | Kashiwaguchi |
| 5,944,638 A | 8/1999 | Maresh |
| 5,947,868 A | 9/1999 | Dugan |
| 5,947,869 A | 9/1999 | Shea |
| 5,947,872 A | 9/1999 | Ryan et al. |
| 5,956,509 A | 9/1999 | Kevner |
| 5,957,699 A | 9/1999 | Peterson et al. |
| 5,961,561 A | 10/1999 | Wakefield, II |
| 5,961,593 A | 10/1999 | Gabber et al. |
| 5,964,701 A | 10/1999 | Asada et al. |
| 5,967,975 A | 10/1999 | Ridgeway |
| 5,970,340 A | 10/1999 | Edgar |
| 5,971,902 A | 10/1999 | Robertson et al. |
| 5,973,696 A | 10/1999 | Agranat |
| 5,976,083 A | 11/1999 | Richardson et al. |
| 5,980,429 A | 11/1999 | Nashner |
| 5,981,168 A | 11/1999 | Reiner et al. |
| 5,984,798 A | 11/1999 | Gilmour |
| 5,984,839 A | 11/1999 | Corkum |
| 5,990,405 A | 11/1999 | Auten et al. |
| 5,993,356 A | 11/1999 | Houston et al. |
| 5,993,362 A | 11/1999 | Ghobadi |
| 5,995,868 A | 11/1999 | Dorfmeister et al. |
| 5,997,476 A | 12/1999 | Brown |
| 6,002,982 A | 12/1999 | Fry |
| 6,004,243 A | 12/1999 | Ewert |
| 6,010,451 A | 1/2000 | Clawson |
| 6,013,007 A | 1/2000 | Root et al. |
| 6,013,009 A | 1/2000 | Karkanen |
| 6,013,011 A | 1/2000 | Moore et al. |
| 6,014,432 A | 1/2000 | Modney |
| 6,014,634 A | 1/2000 | Scroggie et al. |
| 6,018,705 A | 1/2000 | Gaudet et al. |

(56) References Cited

U.S. PATENT DOCUMENTS

| | | |
|---|---|---|
| 6,027,428 A | 2/2000 | Thomas et al. |
| 6,027,429 A | 2/2000 | Daniels |
| 6,033,227 A | 3/2000 | Ishige |
| 6,033,344 A | 3/2000 | Trulaske et al. |
| 6,039,677 A | 3/2000 | Spletzer |
| 6,042,516 A | 3/2000 | Norton |
| 6,042,519 A | 3/2000 | Shea |
| 6,045,487 A | 4/2000 | Miller |
| 6,045,490 A | 4/2000 | Shafer |
| 6,050,822 A | 4/2000 | Faughn |
| 6,050,921 A | 4/2000 | Wang |
| 6,050,923 A | 4/2000 | Yu |
| 6,050,924 A | 4/2000 | Shea |
| 6,050,942 A | 4/2000 | Rust et al. |
| 6,053,737 A | 4/2000 | Babbitt et al. |
| 6,053,844 A | 4/2000 | Clem |
| 6,055,513 A | 4/2000 | Katz et al. |
| 6,055,573 A | 4/2000 | Gardenswartz et al. |
| 6,056,670 A | 5/2000 | Shu et al. |
| 6,059,576 A | 5/2000 | Brann |
| 6,059,692 A | 5/2000 | Hickman |
| 6,065,572 A | 5/2000 | Schober et al. |
| 6,066,075 A | 5/2000 | Poulton |
| 6,066,077 A | 5/2000 | Horst |
| 6,066,705 A | 5/2000 | Calderon et al. |
| 6,068,578 A | 5/2000 | Wang |
| 6,075,525 A | 6/2000 | Hsieh |
| 6,086,379 A | 7/2000 | Pendergast et al. |
| 6,090,017 A | 7/2000 | Wang |
| 6,099,439 A | 8/2000 | Ryan et al. |
| 6,102,832 A | 8/2000 | Tani |
| 6,102,846 A | 8/2000 | Patton et al. |
| 6,103,203 A | 8/2000 | Fischer |
| 6,106,297 A | 8/2000 | Pollak et al. |
| 6,110,076 A | 8/2000 | Hurt |
| 6,113,537 A | 9/2000 | Castano |
| 6,122,340 A | 9/2000 | Darley et al. |
| 6,126,577 A | 10/2000 | Chang |
| 6,128,663 A | 10/2000 | Thomas |
| 6,132,337 A | 10/2000 | Krupka et al. |
| 6,132,340 A | 10/2000 | Wang |
| 6,133,610 A | 10/2000 | Bolam et al. |
| 6,135,924 A | 10/2000 | Gibbs et al. |
| 6,142,870 A | 11/2000 | Wada et al. |
| 6,142,912 A | 11/2000 | Profaci |
| 6,142,913 A | 11/2000 | Ewert |
| 6,146,313 A | 11/2000 | Whan-Tong et al. |
| 6,148,262 A | 11/2000 | Fry |
| 6,151,586 A | 11/2000 | Brown |
| 6,152,854 A | 11/2000 | Carmein |
| 6,152,856 A | 11/2000 | Studor et al. |
| 6,159,131 A | 12/2000 | Pfeffer |
| 6,162,151 A | 12/2000 | Tani et al. |
| 6,162,183 A | 12/2000 | Hoover |
| 6,162,189 A | 12/2000 | Girone et al. |
| 6,171,186 B1 | 1/2001 | Kurosawa et al. |
| 6,171,218 B1 | 1/2001 | Shea |
| 6,174,267 B1 | 1/2001 | Dalebout |
| 6,174,268 B1 | 1/2001 | Novak |
| 6,175,608 B1 | 1/2001 | Pyles et al. |
| 6,176,241 B1 | 1/2001 | Blau et al. |
| 6,176,814 B1 | 1/2001 | Ryan et al. |
| 6,179,746 B1 | 1/2001 | Delman |
| 6,179,753 B1 | 1/2001 | Barker et al. |
| 6,183,259 B1 | 2/2001 | Macri et al. |
| 6,183,425 B1 | 2/2001 | Whalen |
| 6,186,145 B1 | 2/2001 | Brown |
| 6,186,290 B1 | 2/2001 | Carlson |
| 6,186,929 B1 | 2/2001 | Endelman et al. |
| 6,193,631 B1 | 2/2001 | Hickman |
| 6,198,394 B1 | 3/2001 | Jacobsen et al. |
| 6,211,451 B1 | 4/2001 | Tohgi et al. |
| 6,220,865 B1 | 4/2001 | Macri et al. |
| 6,221,451 B1 | 4/2001 | Lauer et al. |
| 6,221,667 B1 | 4/2001 | Reiner et al. |
| 6,224,387 B1 | 5/2001 | Jones |
| 6,224,516 B1 | 5/2001 | Disch |
| 6,225,977 B1 | 5/2001 | Li |
| 6,227,968 B1 | 5/2001 | Suzuki et al. |
| 6,230,501 B1 | 5/2001 | Bailey, Sr. et al. |
| 6,231,481 B1 | 5/2001 | Brock |
| 6,231,482 B1 | 5/2001 | Thompson |
| 6,234,936 B1 | 5/2001 | Wang |
| 6,238,323 B1 | 5/2001 | Simonson |
| 6,241,524 B1 | 6/2001 | Aoshima et al. |
| 6,244,987 B1 | 6/2001 | Ohsuga et al. |
| 6,244,988 B1 | 6/2001 | Delman |
| 6,251,048 B1 | 6/2001 | Kaufman |
| 6,252,153 B1 | 6/2001 | Toyama |
| 6,254,513 B1 | 7/2001 | Takenaka et al. |
| 6,259,944 B1 | 7/2001 | Margulis et al. |
| 6,260,970 B1 | 7/2001 | Horn |
| 6,278,378 B1 | 8/2001 | Feiner et al. |
| 6,280,362 B1 | 8/2001 | Dalebout et al. |
| 6,283,760 B1 | 9/2001 | Wakamoto |
| 6,283,859 B1 | 9/2001 | Carlson et al. |
| 6,283,896 B1 | 9/2001 | Grunfeld |
| 6,287,239 B1 | 9/2001 | Hernandez |
| 6,292,688 B1 | 9/2001 | Patton |
| 6,293,802 B1 | 9/2001 | Ahlgren |
| 6,307,167 B1 | 10/2001 | Kajio et al. |
| 6,308,565 B1 | 10/2001 | French |
| 6,312,363 B1 | 11/2001 | Watterson et al. |
| 6,312,366 B1 | 11/2001 | Prusick |
| 6,313,363 B1 | 11/2001 | Joly et al. |
| 6,314,058 B1 | 11/2001 | Lee |
| 6,317,151 B1 | 11/2001 | Ohsuga et al. |
| 6,322,451 B1 | 11/2001 | Miura |
| 6,328,677 B1 | 12/2001 | Drapeau |
| 6,334,624 B1 | 1/2002 | Giglio |
| 6,336,891 B1 | 1/2002 | Fedrigon et al. |
| 6,342,028 B1 | 1/2002 | De Sane |
| 6,345,197 B1 | 2/2002 | Fabrizio |
| 6,350,218 B1 | 2/2002 | Dalebout et al. |
| 6,356,856 B1 | 3/2002 | Damen et al. |
| 6,358,187 B1 | 3/2002 | Smith |
| 6,368,251 B1 | 4/2002 | Casler |
| 6,369,313 B2 | 4/2002 | Devecka |
| 6,371,123 B1 | 4/2002 | Stark et al. |
| 6,371,850 B1 | 4/2002 | Sonoda |
| 6,385,651 B2 | 5/2002 | Dancs et al. |
| 6,390,923 B1 | 5/2002 | Yoshitomi et al. |
| 6,398,695 B2 | 6/2002 | Miller |
| 6,402,520 B1 | 6/2002 | Freer |
| 6,402,558 B1 | 6/2002 | Hung-Ju et al. |
| 6,404,418 B1 | 6/2002 | Leem |
| 6,405,077 B1 | 6/2002 | Birnbaum et al. |
| 6,409,513 B1 | 6/2002 | Kawamura et al. |
| 6,418,394 B1 | 7/2002 | Puolakanaho et al. |
| 6,419,611 B1 | 7/2002 | Levine et al. |
| 6,421,358 B1 | 7/2002 | Stimmel et al. |
| 6,428,449 B1 | 8/2002 | Apseloff |
| 6,446,745 B1 | 9/2002 | Lee |
| 6,447,424 B1 | 9/2002 | Ashby et al. |
| 6,450,922 B1 | 9/2002 | Henderson et al. |
| 6,458,060 B1 | 10/2002 | Watterson et al. |
| 6,458,061 B2 | 10/2002 | Simonson |
| 6,461,279 B1 | 10/2002 | Kuo |
| 6,463,385 B1 | 10/2002 | Fry |
| 6,464,618 B1 | 10/2002 | Shea |
| 6,473,483 B2 | 10/2002 | Pyles |
| 6,474,193 B1 | 11/2002 | Farney |
| 6,475,115 B1 | 11/2002 | Candito |
| 6,475,122 B2 | 11/2002 | Wu |
| 6,478,736 B1 | 11/2002 | Mault |
| 6,484,062 B1 | 11/2002 | Kim |
| 6,493,652 B1 | 12/2002 | Ohlenbusch et al. |
| 6,497,426 B2 | 12/2002 | Vanpelt |
| 6,503,173 B2 | 1/2003 | Clem |
| 6,511,402 B2 | 1/2003 | Shu et al. |
| 6,513,381 B2 | 2/2003 | Fyfe et al. |
| 6,513,532 B2 | 2/2003 | Mault et al. |
| 6,515,593 B1 | 2/2003 | Stark et al. |
| 6,527,674 B1 | 3/2003 | Clem |

(56) References Cited

U.S. PATENT DOCUMENTS

| | | |
|---|---|---|
| 6,527,685 B2 | 3/2003 | Endelman et al. |
| 6,527,711 B1 | 3/2003 | Stivoric et al. |
| 6,527,712 B1 | 3/2003 | Brown et al. |
| 6,530,864 B1 | 3/2003 | Parks |
| 6,539,931 B2 | 4/2003 | Trajkovic et al. |
| 6,547,702 B1 | 4/2003 | Heidecke |
| 6,551,220 B1 | 4/2003 | Schroeder |
| 6,560,903 B1 | 5/2003 | Darley |
| 6,561,951 B2 | 5/2003 | Besser et al. |
| 6,561,955 B1 | 5/2003 | Dreissigacker et al. |
| 6,563,489 B1 | 5/2003 | Latypov et al. |
| 6,572,511 B1 | 6/2003 | Volpe |
| 6,572,512 B2 | 6/2003 | Anderson et al. |
| 6,579,214 B2 | 6/2003 | Crump |
| 6,582,342 B2 | 6/2003 | Kaufman |
| 6,585,622 B1 | 7/2003 | Shum et al. |
| 6,592,502 B1 | 7/2003 | Phillips |
| 6,599,223 B2 | 7/2003 | Wang |
| 6,601,016 B1 | 7/2003 | Brown et al. |
| 6,601,358 B2 | 8/2003 | Panatta |
| 6,602,191 B2 | 8/2003 | Quy |
| 6,604,008 B2 | 8/2003 | Chudley et al. |
| 6,604,023 B1 | 8/2003 | Brown et al. |
| 6,604,419 B2 | 8/2003 | Guzman |
| 6,605,020 B1 | 8/2003 | Huang |
| 6,605,038 B1 | 8/2003 | Teller et al. |
| 6,605,044 B2 | 8/2003 | Bimbaum |
| 6,606,374 B1 | 8/2003 | Rokoff et al. |
| 6,611,789 B1 | 8/2003 | Darley |
| 6,612,170 B2 | 9/2003 | Brown |
| 6,612,492 B1 | 9/2003 | Yen |
| 6,616,578 B2 | 9/2003 | Alessandri |
| 6,619,835 B2 | 9/2003 | Kita |
| 6,626,799 B2 | 9/2003 | Watterson et al. |
| 6,626,800 B1 | 9/2003 | Casler |
| 6,626,803 B1 | 9/2003 | Oglesby et al. |
| 6,629,909 B1 | 10/2003 | Stearns et al. |
| 6,634,992 B1 | 10/2003 | Ogawa |
| 6,635,015 B2 | 10/2003 | Sagel |
| 6,638,160 B2 | 10/2003 | Yoshitomi |
| 6,645,124 B1 | 11/2003 | Clem |
| 6,645,125 B1 | 11/2003 | Stearns et al. |
| 6,645,126 B1 | 11/2003 | Martin et al. |
| 6,648,353 B1 | 11/2003 | Cabal |
| 6,648,798 B2 | 11/2003 | Yoo |
| 6,648,802 B2 | 11/2003 | Ware |
| 6,656,091 B1 | 12/2003 | Abelbeck |
| 6,659,916 B1 | 12/2003 | Shea |
| 6,659,946 B1 | 12/2003 | Batchelor et al. |
| 6,660,949 B2 | 12/2003 | Kamino et al. |
| 6,669,600 B2 | 12/2003 | Warner |
| 6,672,991 B2 | 1/2004 | O'Malley |
| 6,672,994 B1 | 1/2004 | Stearns et al. |
| 6,676,569 B1 | 1/2004 | Radow |
| 6,677,299 B2 | 1/2004 | Stern et al. |
| 6,681,014 B1 | 1/2004 | Ghassabian |
| 6,685,480 B2 | 2/2004 | Nishimoto et al. |
| 6,685,607 B1 | 2/2004 | Olson |
| 6,687,535 B2 | 2/2004 | Hautala et al. |
| 6,689,057 B1 | 2/2004 | Shinsel et al. |
| 6,691,839 B1 | 2/2004 | El-Kassouf |
| 6,695,694 B2 | 2/2004 | Ishikawa et al. |
| 6,695,799 B2 | 2/2004 | Kitadou et al. |
| 6,700,788 B2 | 3/2004 | Matsushita et al. |
| 6,701,271 B2 | 3/2004 | Willner et al. |
| 6,702,719 B1 | 3/2004 | Brown et al. |
| 6,712,737 B1 | 3/2004 | Nusbaum |
| 6,716,139 B1 | 4/2004 | Hosseinzadeh-Dolkhani |
| 6,719,667 B2 | 4/2004 | Wong et al. |
| 6,722,888 B1 | 4/2004 | Macri et al. |
| 6,726,113 B2 | 4/2004 | Guo |
| 6,730,002 B2 | 5/2004 | Hald et al. |
| 6,736,759 B1 | 5/2004 | Stubbs et al. |
| 6,740,007 B2 | 5/2004 | Gordon et al. |
| 6,740,009 B1 | 5/2004 | Hall |
| 6,746,247 B2 | 6/2004 | Barton |
| 6,746,371 B1 | 6/2004 | Brown et al. |
| 6,749,432 B2 | 6/2004 | French et al. |
| 6,749,536 B1 | 6/2004 | Cuskaden et al. |
| 6,749,537 B1 | 6/2004 | Hickman |
| 6,749,540 B1 | 6/2004 | Pasero et al. |
| 6,749,546 B1 | 6/2004 | Yang |
| 6,751,439 B2 | 6/2004 | Tice et al. |
| 6,757,572 B1 | 6/2004 | Forest |
| 6,761,667 B1 | 7/2004 | Cutler et al. |
| 6,764,429 B1 | 7/2004 | Michalow |
| 6,764,431 B2 | 7/2004 | Yoss |
| 6,769,689 B1 | 8/2004 | Shimomura et al. |
| 6,776,740 B1 | 8/2004 | Anderson et al. |
| 6,783,482 B2 | 8/2004 | Oglesby et al. |
| 6,786,415 B2 | 9/2004 | Yiu |
| 6,786,821 B2 | 9/2004 | Nobe et al. |
| 6,786,848 B2 | 9/2004 | Yamashita et al. |
| 6,790,163 B1 | 9/2004 | Van De Laarschot |
| 6,790,178 B1 | 9/2004 | Mault et al. |
| 6,793,607 B2 | 9/2004 | Neil |
| 6,796,927 B2 | 9/2004 | Toyama |
| 6,798,378 B1 | 9/2004 | Walters |
| 6,807,869 B2 | 10/2004 | Farringdon et al. |
| 6,808,472 B1 | 10/2004 | Hickman |
| 6,808,473 B2 | 10/2004 | Hisano et al. |
| 6,811,516 B1 | 11/2004 | Dugan |
| 6,811,520 B2 | 11/2004 | Wu |
| 6,817,979 B2 | 11/2004 | Nihtilä |
| 6,823,036 B1 | 11/2004 | Chen |
| 6,823,327 B1 | 11/2004 | Klug |
| 6,824,502 B1 | 11/2004 | Huang |
| 6,825,164 B1 | 11/2004 | Stern et al. |
| 6,825,876 B1 | 11/2004 | Easwar et al. |
| 6,827,669 B2 | 12/2004 | Cohen et al. |
| 6,827,670 B1 | 12/2004 | Stark et al. |
| 6,827,822 B2 | 12/2004 | Tao et al. |
| 6,830,540 B2 | 12/2004 | Watterson |
| 6,830,541 B2 | 12/2004 | Wu |
| 6,835,166 B1 | 12/2004 | Stearns et al. |
| 6,837,827 B1 | 1/2005 | Lee et al. |
| 6,840,904 B2 | 1/2005 | Goldberg |
| 6,846,270 B1 | 1/2005 | Etnyre |
| 6,852,068 B2 | 2/2005 | Ogawa |
| 6,852,069 B2 | 2/2005 | Park |
| 6,859,215 B1 | 2/2005 | Brown et al. |
| 6,863,641 B1 | 3/2005 | Brown et al. |
| 6,866,613 B1 | 3/2005 | Brown et al. |
| 6,872,077 B2 | 3/2005 | Yeager |
| 6,872,187 B1 | 3/2005 | Stark et al. |
| 6,875,157 B1 | 4/2005 | Wang |
| 6,876,496 B2 | 4/2005 | French et al. |
| 6,876,947 B1 | 4/2005 | Darley et al. |
| 6,878,099 B2 | 4/2005 | Corbalis et al. |
| 6,881,176 B2 | 4/2005 | Oishi et al. |
| 6,882,955 B1 | 4/2005 | Ohlenbusch et al. |
| 6,885,971 B2 | 4/2005 | Vock et al. |
| 6,886,613 B1 | 5/2005 | Zahdeh |
| 6,887,190 B1 | 5/2005 | Azari |
| 6,902,513 B1 | 6/2005 | Mcclure |
| 6,905,440 B2 | 6/2005 | Heppert |
| 6,908,417 B2 | 6/2005 | Jackson |
| 6,915,271 B1 | 7/2005 | Meyer et al. |
| 6,918,858 B2 | 7/2005 | Watterson et al. |
| 6,918,860 B1 | 7/2005 | Nusbaum |
| 6,921,351 B1 | 7/2005 | Hickman et al. |
| 6,923,747 B1 | 8/2005 | Chu |
| 6,934,658 B2 | 8/2005 | Clabes et al. |
| 6,936,007 B2 | 8/2005 | Quy |
| 6,937,289 B1 | 8/2005 | Ranta et al. |
| 6,939,271 B1 | 9/2005 | Whan-Tong et al. |
| 6,942,599 B1 | 9/2005 | Racine |
| 6,945,916 B2 | 9/2005 | Schroeder |
| 6,949,054 B1 | 9/2005 | Stearns |
| 6,952,221 B1 | 10/2005 | Holtz et al. |
| 6,955,542 B2 | 10/2005 | Roncalez et al. |
| 6,960,156 B2 | 11/2005 | Smith |
| 6,971,972 B1 | 12/2005 | Mcgovern |
| 6,971,973 B2 | 12/2005 | Cohen et al. |

(56) References Cited

U.S. PATENT DOCUMENTS

| | | |
|---|---|---|
| 6,974,403 B2 | 12/2005 | Wong et al. |
| 6,974,404 B1 | 12/2005 | Watterson et al. |
| 6,975,910 B1 | 12/2005 | Brown et al. |
| 6,976,624 B2 | 12/2005 | Hsiao |
| 6,976,958 B2 | 12/2005 | Quy |
| 6,991,586 B2 | 1/2006 | Lapcevic |
| 6,996,852 B1 | 2/2006 | Cabrera |
| 6,997,852 B2 | 2/2006 | Watterson et al. |
| 6,997,853 B1 | 2/2006 | Cuskaden et al. |
| 7,008,356 B2 | 3/2006 | Hung |
| 7,015,950 B1 | 3/2006 | Pryor |
| 7,016,812 B2 | 3/2006 | Aritsuka et al. |
| 7,020,508 B2 | 3/2006 | Stivoric |
| 7,022,047 B2 | 4/2006 | Cohen et al. |
| 7,022,048 B1 | 4/2006 | Fernandez |
| 7,022,049 B2 | 4/2006 | Ryan et al. |
| 7,033,176 B2 | 4/2006 | Feldman |
| 7,035,936 B2 | 4/2006 | Fouquet |
| 7,038,855 B2 | 5/2006 | French et al. |
| 7,041,049 B1 | 5/2006 | Raniere |
| 7,044,891 B1 | 5/2006 | Rivera |
| 7,051,049 B2 | 5/2006 | Samn |
| 7,056,265 B1 | 6/2006 | Shea |
| 7,060,006 B1 | 6/2006 | Watterson et al. |
| 7,060,008 B2 | 6/2006 | Watterson et al. |
| 7,060,031 B2 | 6/2006 | Webb et al. |
| 7,063,644 B2 | 6/2006 | Albert et al. |
| 7,065,768 B1 | 6/2006 | Janzig et al. |
| 7,066,865 B2 | 6/2006 | Radow |
| 7,070,415 B2 | 7/2006 | Hojo et al. |
| 7,070,539 B2 | 7/2006 | Brown et al. |
| 7,070,542 B2 | 7/2006 | Reyes et al. |
| 7,070,545 B2 | 7/2006 | Lull et al. |
| 7,072,789 B2 | 7/2006 | Vock et al. |
| 7,091,635 B1 | 8/2006 | Gilliland et al. |
| 7,094,184 B1 | 8/2006 | Chen et al. |
| 7,097,593 B2 | 8/2006 | Chang |
| 7,108,641 B2 | 9/2006 | Pertegaz-Esteban |
| 7,113,166 B1 | 9/2006 | Rosenberg et al. |
| 7,115,076 B2 | 10/2006 | Oglesby et al. |
| 7,121,980 B2 | 10/2006 | Chen |
| 7,128,692 B2 | 10/2006 | Black |
| 7,128,693 B2 | 10/2006 | Brown et al. |
| 7,139,835 B2 | 11/2006 | Fouquet et al. |
| 7,148,879 B2 | 12/2006 | Amento et al. |
| 7,151,214 B2 | 12/2006 | Barry |
| 7,156,808 B2 | 1/2007 | Quy |
| 7,156,809 B2 | 1/2007 | Quy |
| 7,158,938 B2 | 1/2007 | Labbe et al. |
| 7,163,489 B1 | 1/2007 | Nelson |
| 7,166,062 B1 | 1/2007 | Watterson et al. |
| 7,166,064 B2 | 1/2007 | Watterson et al. |
| 7,169,093 B2 | 1/2007 | Simonson et al. |
| 7,170,016 B2 | 1/2007 | Dumornay |
| 7,171,331 B2 | 1/2007 | Vock et al. |
| 7,182,738 B2 | 2/2007 | Bonutti et al. |
| 7,187,961 B2 | 3/2007 | Yamashita et al. |
| 7,188,439 B2 | 3/2007 | DiBenedetto et al. |
| 7,192,387 B2 | 3/2007 | Mendel |
| 7,197,029 B1 | 3/2007 | Osterhout et al. |
| 7,200,517 B2 | 4/2007 | Darley et al. |
| 7,207,930 B2 | 4/2007 | Bonutti |
| 7,217,224 B2 | 5/2007 | Thomas |
| 7,220,219 B2 | 5/2007 | Papadopoulos et al. |
| 7,223,213 B2 | 5/2007 | Golesh |
| 7,224,326 B2 | 5/2007 | Sefton |
| 7,225,282 B1 | 5/2007 | Lyle |
| 7,225,565 B2 | 6/2007 | DiBenedetto et al. |
| 7,236,154 B1 | 6/2007 | Kerr et al. |
| 7,250,022 B2 | 7/2007 | Dalebout |
| 7,254,516 B2 | 8/2007 | Case, Jr. et al. |
| 7,257,468 B1 | 8/2007 | Costa et al. |
| 7,259,906 B1 | 8/2007 | Islam |
| 7,264,554 B2 | 9/2007 | Bentley |
| 7,278,955 B2 | 10/2007 | Giannelli et al. |
| 7,278,966 B2 | 10/2007 | Hjelt et al. |
| 7,285,090 B2 | 10/2007 | Stivoric et al. |
| 7,292,151 B2 | 11/2007 | Ferguson |
| 7,294,095 B2 | 11/2007 | Charnitski |
| 7,303,508 B2 | 12/2007 | Toyama et al. |
| 7,303,510 B2 | 12/2007 | Gebhardt |
| 7,308,818 B2 | 12/2007 | Considine et al. |
| 7,319,457 B2 | 1/2008 | Lin et al. |
| 7,322,907 B2 | 1/2008 | Bowser |
| 7,328,119 B1 | 2/2008 | Pryor |
| 7,329,684 B2 | 2/2008 | Mjalli et al. |
| 7,336,178 B2 | 2/2008 | Le |
| 7,350,787 B2 | 4/2008 | Voss |
| 7,351,187 B2 | 4/2008 | Seliber |
| 7,352,365 B2 | 4/2008 | Trachte |
| 7,354,380 B2 | 4/2008 | Volpe, Jr. |
| 7,357,756 B2 | 4/2008 | Demas |
| 7,365,647 B2 | 4/2008 | Nativ |
| 7,367,926 B2 | 5/2008 | Clark |
| 7,369,121 B2 | 5/2008 | Lane |
| 7,372,485 B1 | 5/2008 | Bodnar et al. |
| 7,373,820 B1 | 5/2008 | James |
| 7,374,519 B2 | 5/2008 | Naidus |
| 7,374,522 B2 | 5/2008 | Arnold |
| 7,383,081 B2 | 6/2008 | Butt et al. |
| 7,398,151 B1 | 7/2008 | Burrell et al. |
| 7,401,918 B2 | 7/2008 | Howell et al. |
| 7,402,125 B2 | 7/2008 | Wang |
| 7,412,206 B1 | 8/2008 | Hutchings et al. |
| 7,416,537 B1 | 8/2008 | Stark et al. |
| 7,418,862 B2 | 9/2008 | Gruben et al. |
| 7,432,184 B2 | 10/2008 | Hosokawa et al. |
| 7,432,454 B1 | 10/2008 | Sze et al. |
| 7,435,202 B2 | 10/2008 | Daly et al. |
| 7,452,336 B2 | 11/2008 | Thompson |
| 7,454,002 B1 | 11/2008 | Gardner et al. |
| 7,455,621 B1 | 11/2008 | Anthony |
| 7,455,622 B2 | 11/2008 | Watterson et al. |
| 7,455,626 B2 | 11/2008 | Trevino et al. |
| 7,462,141 B1 | 12/2008 | Raboin et al. |
| 7,465,257 B1 | 12/2008 | Morgan, Jr. |
| 7,477,890 B1 | 1/2009 | Narayanaswami |
| 7,480,512 B2 | 1/2009 | Graham et al. |
| 7,489,979 B2 | 2/2009 | Rosenberg |
| 7,491,159 B2 | 2/2009 | Patterson |
| 7,494,450 B2 | 2/2009 | Solomon |
| 7,503,476 B2 | 3/2009 | Bhavnani |
| 7,503,878 B1 | 3/2009 | Amsbury et al. |
| 7,507,183 B2 | 3/2009 | Anderson |
| 7,507,187 B2 | 3/2009 | Dyer et al. |
| 7,507,190 B2 | 3/2009 | Piane, Jr. |
| 7,510,509 B2 | 3/2009 | Hickman |
| 7,519,327 B2 | 4/2009 | White |
| 7,519,537 B2 | 4/2009 | Rosenberg |
| 7,521,623 B2 | 4/2009 | Bowen |
| 7,532,977 B2 | 5/2009 | Chen |
| 7,534,206 B1 | 5/2009 | Lovitt et al. |
| 7,537,546 B2 | 5/2009 | Watterson et al. |
| 7,537,549 B2 | 5/2009 | Nelson et al. |
| 7,537,552 B2 | 5/2009 | Dalebout et al. |
| 7,539,487 B2 | 5/2009 | Sinclair et al. |
| 7,542,816 B2 | 6/2009 | Rosenberg |
| 7,543,934 B2 | 6/2009 | Howell et al. |
| 7,549,947 B2 | 6/2009 | Hickman et al. |
| 7,553,260 B2 | 6/2009 | Piaget et al. |
| 7,556,590 B2 | 7/2009 | Watterson et al. |
| 7,561,989 B2 | 7/2009 | Banks et al. |
| 7,562,117 B2 | 7/2009 | Rosenberg |
| 7,575,536 B1 | 8/2009 | Hickman |
| 7,575,538 B1 | 8/2009 | Clark |
| 7,577,522 B2 | 8/2009 | Rosenberg |
| 7,579,946 B2 | 8/2009 | Case, Jr. |
| 7,585,251 B2 | 9/2009 | Doody, Jr. et al. |
| 7,585,254 B1 | 9/2009 | Vittone |
| 7,585,258 B2 | 9/2009 | Watson et al. |
| 7,586,032 B2 | 9/2009 | Louis |
| 7,591,795 B2 | 9/2009 | Whalen et al. |
| 7,598,255 B2 | 10/2009 | Dvorak |
| 7,601,096 B2 | 10/2009 | Negrin |

(56) References Cited

U.S. PATENT DOCUMENTS

| | | |
|---|---|---|
| 7,601,097 B2 | 10/2009 | Miyamaru et al. |
| 7,602,301 B1 | 10/2009 | Stirling et al. |
| 7,603,255 B2 | 10/2009 | Case, Jr. et al. |
| 7,607,243 B2 | 10/2009 | Berner, Jr. et al. |
| 7,616,097 B1 | 11/2009 | Whang |
| 7,618,345 B2 | 11/2009 | Corbalis et al. |
| 7,618,346 B2 | 11/2009 | Crawford et al. |
| 7,618,350 B2 | 11/2009 | Dalebout et al. |
| 7,619,514 B1 | 11/2009 | Stone |
| 7,621,850 B2 | 11/2009 | Piaget et al. |
| 7,625,314 B2 | 12/2009 | Ungari |
| 7,625,315 B2 | 12/2009 | Hickman |
| 7,625,316 B1 | 12/2009 | Amsbury et al. |
| 7,628,730 B1 | 12/2009 | Watterson et al. |
| 7,628,737 B2 | 12/2009 | Kowallis et al. |
| 7,631,382 B2 | 12/2009 | DiBenedetto et al. |
| 7,637,847 B1 | 12/2009 | Hickman |
| 7,641,592 B2 | 1/2010 | Roche |
| 7,643,895 B2 | 1/2010 | Gupta et al. |
| 7,645,212 B2 | 1/2010 | Ashby et al. |
| 7,645,213 B2 | 1/2010 | Watterson |
| 7,647,196 B2 | 1/2010 | Kahn et al. |
| 7,648,443 B2 | 1/2010 | Schenk |
| 7,648,446 B2 | 1/2010 | Chiles et al. |
| 7,648,463 B1 | 1/2010 | Elhag et al. |
| 7,648,858 B2 | 1/2010 | Tang et al. |
| 7,651,442 B2 | 1/2010 | Carlson |
| 7,654,229 B2 | 2/2010 | Smith |
| 7,654,948 B2 | 2/2010 | Kaplan et al. |
| 7,658,694 B2 | 2/2010 | Ungari |
| 7,658,695 B1 | 2/2010 | Amsbury et al. |
| 7,662,065 B1 | 2/2010 | Kahn et al. |
| 7,662,282 B2 | 2/2010 | Lee et al. |
| 7,670,263 B2 | 3/2010 | Ellis |
| 7,676,332 B2 | 3/2010 | Damen |
| 7,677,723 B2 | 3/2010 | Howell et al. |
| 7,678,023 B1 | 3/2010 | Shea |
| 7,682,286 B2 | 3/2010 | Badarneh et al. |
| 7,683,252 B2 | 3/2010 | Oliver et al. |
| 7,689,437 B1 | 3/2010 | Teller et al. |
| 7,690,556 B1 | 4/2010 | Kahn et al. |
| 7,698,101 B2 | 4/2010 | Alten et al. |
| 7,698,359 B2 | 4/2010 | Wray et al. |
| 7,699,752 B1 | 4/2010 | Anderson |
| 7,699,753 B2 | 4/2010 | Daikeler |
| 7,699,754 B2 | 4/2010 | Schneider |
| 7,699,755 B2 | 4/2010 | Feldman et al. |
| 7,702,781 B2 | 4/2010 | Devolites |
| 7,703,974 B2 | 4/2010 | Bouille |
| 7,704,192 B2 | 4/2010 | Dyer et al. |
| 7,705,230 B2 | 4/2010 | Bowen |
| 7,713,171 B1 | 5/2010 | Hickman |
| 7,717,825 B2 | 5/2010 | Van Der Hoeven |
| 7,717,827 B2 | 5/2010 | Veli-Pekka Kurunmäki et al. |
| 7,717,866 B2 | 5/2010 | Damen |
| 7,722,503 B1 | 5/2010 | Smith et al. |
| 7,725,362 B2 | 5/2010 | Weathers, Jr. |
| 7,727,117 B2 | 6/2010 | Feldman et al. |
| 7,727,125 B2 | 6/2010 | Day |
| 7,728,214 B2 | 6/2010 | Oliver et al. |
| 7,736,272 B2 | 6/2010 | Martens |
| 7,739,076 B1 | 6/2010 | Vock et al. |
| 7,740,562 B2 | 6/2010 | Jones |
| 7,740,588 B1 | 6/2010 | Sciarra |
| 7,745,716 B1 | 6/2010 | Murphy |
| 7,747,671 B2 | 6/2010 | Ku |
| 7,749,137 B2 | 7/2010 | Watt et al. |
| 7,753,824 B2 | 7/2010 | Wang |
| 7,753,825 B2 | 7/2010 | Jaquish et al. |
| 7,753,861 B1 | 7/2010 | Kahn et al. |
| 7,758,469 B2 | 7/2010 | Dyer et al. |
| 7,758,523 B2 | 7/2010 | Collings et al. |
| 7,761,300 B2 | 7/2010 | Klingler |
| 7,762,931 B2 | 7/2010 | Fisher et al. |
| 7,762,934 B1 | 7/2010 | Munson, Jr. et al. |
| 7,764,990 B2 | 7/2010 | Martikka et al. |
| 7,765,348 B2 | 7/2010 | Dybsetter |
| 7,766,794 B2 | 8/2010 | Oliver et al. |
| 7,766,798 B2 | 8/2010 | Hamilton |
| 7,770,181 B2 | 8/2010 | Snover et al. |
| 7,771,319 B1 | 8/2010 | Lannon |
| 7,771,320 B2 | 8/2010 | Riley et al. |
| 7,771,325 B2 | 8/2010 | Baker |
| 7,771,329 B2 | 8/2010 | Dalebout et al. |
| 7,775,128 B2 | 8/2010 | Roessingh et al. |
| 7,775,936 B2 | 8/2010 | Wilkinson |
| 7,789,800 B1 | 9/2010 | Watterson et al. |
| 7,794,014 B2 | 9/2010 | Beall et al. |
| 7,798,942 B2 | 9/2010 | Digiulio |
| 7,805,149 B2 | 9/2010 | Werner et al. |
| 7,806,806 B2 | 10/2010 | Jaquish |
| 7,806,815 B2 | 10/2010 | Fernandez |
| 7,809,153 B2 | 10/2010 | Bravomalo et al. |
| 7,811,200 B2 | 10/2010 | Lai |
| 7,811,201 B1 | 10/2010 | Mikan et al. |
| 7,813,715 B2 | 10/2010 | McKillop et al. |
| 7,815,549 B2 | 10/2010 | Crawford et al. |
| 7,822,547 B2 | 10/2010 | Lindroos |
| 7,825,319 B2 | 11/2010 | Turner |
| 7,827,000 B2 | 11/2010 | Stirling et al. |
| 7,830,570 B2 | 11/2010 | Morita et al. |
| 7,833,129 B2 | 11/2010 | Badarneh |
| 7,833,135 B2 | 11/2010 | Radow |
| 7,837,595 B2 | 11/2010 | Rice |
| 7,837,596 B2 | 11/2010 | Astilean |
| 7,837,599 B2 | 11/2010 | Kowalczewski et al. |
| 7,839,058 B1 | 11/2010 | Churchill et al. |
| 7,840,346 B2 | 11/2010 | Huhtala et al. |
| 7,841,967 B1 | 11/2010 | Kahn |
| 7,846,067 B2 | 12/2010 | Hanoun |
| 7,846,080 B2 | 12/2010 | Boren |
| 7,857,731 B2 | 12/2010 | Hickman et al. |
| 7,857,732 B2 | 12/2010 | Nielson |
| 7,862,476 B2 | 1/2011 | Radow |
| 7,862,478 B2 | 1/2011 | Watterson et al. |
| 7,862,483 B2 | 1/2011 | Hendrickson et al. |
| 7,867,088 B2 | 1/2011 | Prum |
| 7,874,957 B2 | 1/2011 | Hurwitz et al. |
| 7,894,177 B2 | 2/2011 | Rothkopf |
| 7,894,849 B2 | 2/2011 | Kass et al. |
| 7,896,782 B2 | 3/2011 | Tamari |
| 7,901,292 B1 | 3/2011 | Uhlir et al. |
| 7,901,323 B2 | 3/2011 | Olason et al. |
| 7,901,325 B2 | 3/2011 | Henderson |
| 7,909,741 B2 | 3/2011 | Kim et al. |
| 7,913,297 B2 | 3/2011 | Wyld |
| 7,914,421 B2 | 3/2011 | Weier et al. |
| 7,914,425 B2 | 3/2011 | Hanoun |
| 7,914,468 B2 | 3/2011 | Shalon et al. |
| 7,917,148 B2 | 3/2011 | Rosenberg |
| 7,918,732 B2 | 4/2011 | Van Noland |
| 7,922,635 B2 | 4/2011 | Lull et al. |
| 7,927,253 B2 | 4/2011 | Vincent |
| 7,927,258 B2 | 4/2011 | Irving et al. |
| 7,931,563 B2 | 4/2011 | Shaw et al. |
| 7,934,983 B1 | 5/2011 | Eisner |
| 7,938,752 B1 | 5/2011 | Wang |
| 7,946,959 B2 | 5/2011 | Shum et al. |
| 7,946,961 B2 | 5/2011 | Blum et al. |
| 7,949,295 B2 | 5/2011 | Kumar et al. |
| 7,950,297 B2 | 5/2011 | Moore et al. |
| 7,951,046 B1 | 5/2011 | Barber, Jr. |
| 7,953,549 B2 | 5/2011 | Graham et al. |
| 7,955,219 B2 | 6/2011 | Birrell et al. |
| 7,959,567 B2 | 6/2011 | Stivoric et al. |
| 7,963,889 B2 | 6/2011 | Badarneh et al. |
| 7,967,728 B2 | 6/2011 | Zavadsky |
| 7,968,574 B2 | 6/2011 | Hangauer, Jr. |
| 7,972,245 B2 | 7/2011 | Temple et al. |
| 7,972,247 B2 | 7/2011 | Daikeler |
| 7,972,249 B1 | 7/2011 | Napalan |
| 7,973,231 B2 | 7/2011 | Bowen |
| 7,974,889 B2 | 7/2011 | Raimbeault |
| 7,976,518 B2 | 7/2011 | Shaughnessy et al. |

(56) References Cited

U.S. PATENT DOCUMENTS

| | | |
|---|---|---|
| 7,978,081 B2 | 7/2011 | Shears et al. |
| 7,980,996 B2 | 7/2011 | Hickman |
| 7,981,000 B2 | 7/2011 | Watterson et al. |
| 7,985,164 B2 | 7/2011 | Ashby |
| 7,988,598 B2 | 8/2011 | Trzecieski |
| 7,988,599 B2 | 8/2011 | Ainsworth et al. |
| 8,002,671 B1 | 8/2011 | Vigilia |
| RE42,698 E | 9/2011 | Kuo et al. |
| 8,012,064 B2 | 9/2011 | Martens |
| 8,012,073 B2 | 9/2011 | Barnett |
| 8,021,270 B2 | 9/2011 | D Eredita |
| 8,021,277 B2 | 9/2011 | Baudhuin |
| 8,025,607 B2 | 9/2011 | Ranky et al. |
| 8,025,612 B1 | 9/2011 | Buzzanco |
| 8,028,443 B2 | 10/2011 | Case, Jr. |
| 8,029,415 B2 | 10/2011 | Ashby et al. |
| 8,033,959 B2 | 10/2011 | Oleson et al. |
| 8,034,294 B1 | 10/2011 | Goldberg |
| 8,037,017 B2 | 10/2011 | Samn |
| 8,038,577 B2 | 10/2011 | Mcintosh |
| 8,040,758 B1 | 10/2011 | Dickinson |
| 8,043,173 B2 | 10/2011 | Menalagha et al. |
| 8,046,803 B1 | 10/2011 | Lee |
| 8,047,965 B2 | 11/2011 | Shea |
| 8,047,966 B2 | 11/2011 | Dorogusker et al. |
| 8,052,580 B2 | 11/2011 | Saalasti et al. |
| 8,052,584 B2 | 11/2011 | Keiser |
| 8,056,687 B2 | 11/2011 | Golden et al. |
| 8,057,360 B2 | 11/2011 | Shea |
| 8,062,182 B2 | 11/2011 | Somers |
| 8,062,192 B1 | 11/2011 | Arstein |
| 8,065,185 B2 | 11/2011 | Foladare et al. |
| 8,066,514 B2 | 11/2011 | Clarke |
| 8,070,655 B1 | 12/2011 | Napolitano |
| 8,075,453 B1 | 12/2011 | Wilkinson |
| 8,078,426 B2 | 12/2011 | Pipinich et al. |
| 8,083,643 B2 | 12/2011 | Ng et al. |
| 8,086,421 B2 | 12/2011 | Case, Jr. et al. |
| 8,088,043 B2 | 1/2012 | Andren et al. |
| 8,088,044 B2 | 1/2012 | Tchao et al. |
| 8,092,381 B2 | 1/2012 | Edwards |
| 8,101,843 B2 | 1/2012 | Turner |
| 8,103,517 B2 | 1/2012 | Hinnebusch |
| 8,105,207 B1 | 1/2012 | Lannon |
| 8,106,563 B2 | 1/2012 | Ritchey |
| 8,109,858 B2 | 2/2012 | Redmann |
| 8,112,281 B2 | 2/2012 | Yeung et al. |
| 8,113,990 B2 | 2/2012 | Kolman et al. |
| 8,113,991 B2 | 2/2012 | Kutliroff |
| 8,116,841 B2 | 2/2012 | Bly et al. |
| 8,121,785 B2 | 2/2012 | Swisher et al. |
| 8,123,527 B2 | 2/2012 | Holljes |
| 8,128,533 B2 | 3/2012 | Nakagawa et al. |
| 8,142,298 B2 | 3/2012 | King et al. |
| 8,142,370 B2 | 3/2012 | Weinberg et al. |
| 8,152,693 B2 | 4/2012 | Nurmela et al. |
| 8,152,695 B2 | 4/2012 | Riley et al. |
| 8,157,706 B2 | 4/2012 | Ainsworth et al. |
| 8,157,731 B2 | 4/2012 | Teller et al. |
| 8,162,804 B2 | 4/2012 | Tagliabue |
| 8,162,857 B2 | 4/2012 | Lanfermann et al. |
| 8,165,893 B1 | 4/2012 | Goldberg et al. |
| 8,167,776 B2 | 5/2012 | Lannon |
| 8,172,723 B1 | 5/2012 | Yanev et al. |
| 8,172,882 B2 | 5/2012 | Klyce et al. |
| 8,176,101 B2 | 5/2012 | Rosenberg |
| 8,177,688 B2 | 5/2012 | Burnfield et al. |
| 8,188,868 B2 | 5/2012 | Case, Jr. |
| 8,192,332 B2 | 6/2012 | Baker et al. |
| 8,200,323 B2 | 6/2012 | Dibenedetto et al. |
| 8,213,908 B2 | 7/2012 | Sangster et al. |
| 8,221,290 B2 | 7/2012 | Vincent et al. |
| 8,221,292 B2 | 7/2012 | Barker et al. |
| 8,224,429 B2 | 7/2012 | Prstojevich et al. |
| 8,225,024 B2 | 7/2012 | Dybsetter |
| 8,231,506 B2 | 7/2012 | Molyneux et al. |
| 8,235,724 B2 | 8/2012 | Gilley et al. |
| 8,241,118 B2 | 8/2012 | Camhi |
| 8,241,186 B2 | 8/2012 | Brodess et al. |
| 8,249,686 B2 | 8/2012 | Libbus et al. |
| 8,251,874 B2 | 8/2012 | Ashby et al. |
| 8,253,586 B1 | 8/2012 | Matak |
| 8,257,228 B2 | 9/2012 | Quatrochi et al. |
| 8,260,667 B2 | 9/2012 | Graham et al. |
| 8,260,858 B2 | 9/2012 | Belz et al. |
| 8,269,093 B2 | 9/2012 | Naik et al. |
| 8,272,996 B2 | 9/2012 | Weier |
| 8,275,143 B2 | 9/2012 | Johnson |
| 8,275,265 B2 | 9/2012 | Kobyakov et al. |
| 8,276,434 B2 | 10/2012 | Senoo |
| 8,280,259 B2 | 10/2012 | George et al. |
| 8,287,434 B2 | 10/2012 | Zavadsky et al. |
| 8,296,172 B2 | 10/2012 | Marci et al. |
| 8,298,123 B2 | 10/2012 | Hickman |
| 8,306,635 B2 | 11/2012 | Pryor |
| 8,308,794 B2 | 11/2012 | Martinson et al. |
| 8,314,840 B1 | 11/2012 | Funk |
| 8,315,823 B2 | 11/2012 | Berme et al. |
| 8,321,004 B2 | 11/2012 | Moon et al. |
| 8,332,544 B1 | 12/2012 | Ralls et al. |
| 8,337,335 B2 | 12/2012 | Dugan |
| 8,341,557 B2 | 12/2012 | Pisula et al. |
| 8,348,840 B2 | 1/2013 | Heit et al. |
| 8,360,785 B2 | 1/2013 | Park et al. |
| 8,360,904 B2 | 1/2013 | Oleson et al. |
| 8,360,935 B2 | 1/2013 | Olsen et al. |
| 8,360,936 B2 | 1/2013 | Dibenedetto et al. |
| 8,363,913 B2 | 1/2013 | Boushey et al. |
| 8,364,250 B2 | 1/2013 | Moon et al. |
| 8,364,389 B2 | 1/2013 | Dorogusker et al. |
| 8,369,936 B2 | 2/2013 | Farringdon et al. |
| 8,371,990 B2 | 2/2013 | Shea |
| 8,374,688 B2 | 2/2013 | Libbus et al. |
| 8,376,910 B2 | 2/2013 | Cheung et al. |
| 8,384,551 B2 | 2/2013 | Ross et al. |
| 8,398,546 B2 | 3/2013 | Pacione et al. |
| 8,403,845 B2 | 3/2013 | Stivoric et al. |
| 8,407,623 B2 | 3/2013 | Kerr et al. |
| 8,412,317 B2 | 4/2013 | Mazar |
| 8,419,593 B2 | 4/2013 | Ainsworth et al. |
| 8,429,223 B2 | 4/2013 | Gilley et al. |
| 8,430,770 B2 | 4/2013 | Dugan |
| 8,437,824 B2 | 5/2013 | Moon et al. |
| 8,452,259 B2 | 5/2013 | Ellis et al. |
| 8,454,437 B2 | 6/2013 | Dugan |
| 8,460,001 B1 | 6/2013 | Chuang |
| 8,460,189 B2 | 6/2013 | Libbus et al. |
| 8,475,338 B2 | 7/2013 | Greenhill et al. |
| 8,475,370 B2 | 7/2013 | McCombie et al. |
| 8,480,541 B1 | 7/2013 | Brunts |
| 8,485,982 B2 | 7/2013 | Gavish et al. |
| 8,485,996 B2 | 7/2013 | Bluman |
| 8,491,446 B2 | 7/2013 | Hinds et al. |
| 8,491,572 B2 | 7/2013 | Martinson et al. |
| 8,493,822 B2 | 7/2013 | Lee et al. |
| 8,503,086 B2 | 8/2013 | French et al. |
| 8,506,457 B2 | 8/2013 | Baudhuin |
| 8,506,458 B2 | 8/2013 | Dugan |
| 8,515,930 B2 | 8/2013 | Hong |
| 8,517,896 B2 | 8/2013 | Robinette et al. |
| 8,517,899 B2 | 8/2013 | Zhou |
| 8,523,789 B2 | 9/2013 | Keiser |
| 8,527,038 B2 | 9/2013 | Moon et al. |
| 8,529,409 B1 | 9/2013 | Lesea-Ames |
| 8,531,386 B1 | 9/2013 | Kerr et al. |
| 8,533,007 B2 | 9/2013 | Egami et al. |
| 8,533,620 B2 | 9/2013 | Hoffman et al. |
| 8,538,333 B2 | 9/2013 | Jain et al. |
| 8,538,723 B2 | 9/2013 | Chang |
| 8,540,641 B2 | 9/2013 | Kroll et al. |
| 8,543,185 B2 | 9/2013 | Yuen et al. |
| 8,545,417 B2 | 10/2013 | Banet et al. |
| 8,554,214 B2 | 10/2013 | Sweeney et al. |
| 8,554,802 B1 | 10/2013 | Barden et al. |

(56) References Cited

U.S. PATENT DOCUMENTS

| | | |
|---|---|---|
| 8,556,778 B1 | 10/2013 | Dugan |
| 8,560,951 B1 | 10/2013 | Snyder et al. |
| 8,562,489 B2 | 10/2013 | Burton et al. |
| 8,568,278 B2 | 10/2013 | Riley et al. |
| 8,571,880 B2 | 10/2013 | Goldberg |
| 8,572,576 B2 | 10/2013 | Elvanoglu et al. |
| 8,579,767 B2 | 11/2013 | Ellis et al. |
| 8,591,411 B2 | 11/2013 | Banet et al. |
| 8,594,772 B2 | 11/2013 | Eggenberger et al. |
| RE44,650 E | 12/2013 | Anderson |
| 8,597,093 B2 | 12/2013 | Engelberg et al. |
| 8,602,997 B2 | 12/2013 | Banet et al. |
| 8,605,048 B2 | 12/2013 | Ye et al. |
| 8,610,593 B2 | 12/2013 | Van Acht et al. |
| 8,613,689 B2 | 12/2013 | Dyer et al. |
| 8,622,873 B2 | 1/2014 | Mcgown |
| 8,628,333 B2 | 1/2014 | Prinzel, III et al. |
| 8,628,453 B2 | 1/2014 | Balakrishnan et al. |
| 8,639,020 B1 | 1/2014 | Kutliroff et al. |
| 8,647,240 B2 | 2/2014 | Heidecke |
| 8,649,890 B2 | 2/2014 | Martin |
| 8,652,010 B2 | 2/2014 | Ellis et al. |
| 8,654,198 B2 | 2/2014 | Pryor |
| 8,655,004 B2 | 2/2014 | Prest et al. |
| 8,662,901 B2 | 3/2014 | Tzao et al. |
| 8,663,106 B2 | 3/2014 | Stivoric et al. |
| 8,667,194 B2 | 3/2014 | Dybsetter et al. |
| 8,670,222 B2 | 3/2014 | Rothkopf |
| 8,672,852 B2 | 3/2014 | Gavish |
| 8,676,170 B2 | 3/2014 | Porrati et al. |
| 8,676,541 B2 | 3/2014 | Schrock et al. |
| 8,678,979 B2 | 3/2014 | Stark et al. |
| 8,684,925 B2 | 4/2014 | Manicka et al. |
| 8,690,578 B1 | 4/2014 | Nusbaum et al. |
| 8,690,735 B2 | 4/2014 | Watterson et al. |
| 8,702,430 B2 | 4/2014 | Dibenedetto et al. |
| 8,704,068 B2 | 4/2014 | Bowen |
| 8,706,530 B2 | 4/2014 | Ohnemus et al. |
| 8,708,842 B2 | 4/2014 | Ganuza |
| 8,712,510 B2 | 4/2014 | Quy |
| 8,718,752 B2 | 5/2014 | Libbus et al. |
| 8,719,202 B1 | 5/2014 | Maeng |
| 8,727,947 B2 | 5/2014 | Tagliabue |
| 8,734,157 B1 | 5/2014 | Hummel, III |
| 8,734,296 B1 | 5/2014 | Brumback et al. |
| 8,734,301 B2 | 5/2014 | Remelius |
| 8,738,732 B2 | 5/2014 | Karidi |
| 8,740,751 B2 | 6/2014 | Shum |
| 8,740,802 B2 | 6/2014 | Banet et al. |
| 8,740,807 B2 | 6/2014 | Banet et al. |
| 8,744,803 B2 | 6/2014 | Park et al. |
| 8,745,104 B1 | 6/2014 | Rosenberg |
| 8,745,496 B2 | 6/2014 | Gilley et al. |
| 8,747,330 B2 | 6/2014 | Banet et al. |
| 8,749,380 B2 | 6/2014 | Vock et al. |
| 8,758,201 B2 | 6/2014 | Ashby et al. |
| 8,762,167 B2 | 6/2014 | Blander et al. |
| 8,762,313 B2 | 6/2014 | Lahav et al. |
| 8,764,609 B1 | 7/2014 | Elahmadie |
| 8,764,651 B2 | 7/2014 | Tran |
| 8,768,769 B2 | 7/2014 | Foladare et al. |
| 8,770,742 B2 | 7/2014 | Howell et al. |
| 8,771,206 B2 | 7/2014 | Gettelman et al. |
| 8,775,454 B2 | 7/2014 | Geer |
| 8,776,264 B2 | 7/2014 | Kiernan |
| 8,777,815 B2 | 7/2014 | Case, Jr. et al. |
| 8,781,568 B2 | 7/2014 | Dugan |
| 8,784,271 B2 | 7/2014 | Brumback et al. |
| 8,784,273 B2 | 7/2014 | Dugan |
| 8,790,220 B2 | 7/2014 | Karvonen |
| 8,790,259 B2 | 7/2014 | Katra et al. |
| 8,795,138 B1 | 8/2014 | Yeh et al. |
| 8,799,200 B2 | 8/2014 | Lahav |
| 8,805,844 B2 | 8/2014 | Schorzman et al. |
| 8,805,941 B2 | 8/2014 | Barak et al. |
| 8,814,754 B2 | 8/2014 | Weast et al. |
| 8,821,350 B2 | 9/2014 | Maertz |
| 8,821,351 B2 | 9/2014 | Abuelsaad et al. |
| 8,825,445 B2 | 9/2014 | Hoffman et al. |
| 8,827,870 B2 | 9/2014 | Dyer et al. |
| 8,831,407 B2 | 9/2014 | Meschter et al. |
| 8,831,538 B2 | 9/2014 | Yuen |
| 8,838,471 B1 | 9/2014 | Shum et al. |
| 8,845,497 B2 | 9/2014 | Turner |
| 8,847,988 B2 | 9/2014 | Geisner et al. |
| 8,861,860 B2 | 10/2014 | Gupta |
| 8,864,587 B2 | 10/2014 | Framel et al. |
| 8,868,448 B2 | 10/2014 | Freishtat et al. |
| 8,870,791 B2 | 10/2014 | Sabatino |
| 8,882,637 B2 | 11/2014 | Ainsworth et al. |
| 8,882,666 B1 | 11/2014 | Goldberg et al. |
| 8,888,583 B2 | 11/2014 | Dugan et al. |
| 8,888,700 B2 | 11/2014 | Banet et al. |
| 8,897,868 B2 | 11/2014 | Mazar et al. |
| 8,900,099 B1 | 12/2014 | Boyette |
| 8,902,714 B2 | 12/2014 | Gossweiler, III et al. |
| 8,903,671 B2 | 12/2014 | Park et al. |
| 8,908,894 B2 | 12/2014 | Amento et al. |
| 8,915,823 B2 | 12/2014 | McKirdy et al. |
| 8,918,465 B2 | 12/2014 | Barak |
| 8,918,543 B2 | 12/2014 | Karstens |
| 8,920,332 B2 | 12/2014 | Hong et al. |
| 8,920,343 B2 | 12/2014 | Sabatino |
| 8,926,475 B2 | 1/2015 | Lin et al. |
| 8,939,831 B2 | 1/2015 | Dugan |
| 8,943,002 B2 | 1/2015 | Zelenko et al. |
| 8,944,958 B1 | 2/2015 | Brumback et al. |
| 8,944,968 B2 | 2/2015 | Miller |
| 8,945,328 B2 | 2/2015 | Longinotti-Buitoni et al. |
| 8,947,226 B2 | 2/2015 | Dugan |
| 8,951,106 B2 | 2/2015 | Crowley |
| 8,951,164 B2 | 2/2015 | Morris et al. |
| 8,951,168 B2 | 2/2015 | Baudhuin |
| 8,954,135 B2 | 2/2015 | Yuen et al. |
| 8,954,290 B2 | 2/2015 | Yuen et al. |
| 8,956,268 B2 | 2/2015 | Huang et al. |
| 8,956,290 B2 | 2/2015 | Gilley et al. |
| 8,956,303 B2 | 2/2015 | Hong et al. |
| 8,958,631 B2 | 2/2015 | Kutliroff et al. |
| 8,961,371 B2 | 2/2015 | Sultan et al. |
| 8,961,413 B2 | 2/2015 | Teller et al. |
| 8,961,414 B2 | 2/2015 | Teller et al. |
| 8,965,348 B1 | 2/2015 | Cronin |
| 8,965,498 B2 | 2/2015 | Katra et al. |
| 8,965,541 B2 | 2/2015 | Martinez et al. |
| 8,965,732 B2 | 2/2015 | Robinette et al. |
| 8,968,161 B2 | 3/2015 | Shapiro et al. |
| 8,972,199 B2 | 3/2015 | Liang |
| 8,976,007 B2 | 3/2015 | Dugan |
| 8,977,194 B2 | 3/2015 | Jain et al. |
| 8,979,765 B2 | 3/2015 | Banet et al. |
| 8,992,383 B2 | 3/2015 | Bilang |
| 8,992,387 B2 | 3/2015 | Watterson et al. |
| 9,005,129 B2 | 4/2015 | Venkatraman et al. |
| 9,011,291 B2 | 4/2015 | Birrell |
| 9,011,292 B2 | 4/2015 | Weast et al. |
| 9,011,293 B2 | 4/2015 | Shavit et al. |
| 9,011,301 B2 | 4/2015 | Balandis et al. |
| 9,017,230 B1 | 4/2015 | Pitts |
| 9,026,927 B2 | 5/2015 | Brumback et al. |
| 9,028,368 B2 | 5/2015 | Ashby et al. |
| 9,028,441 B2 | 5/2015 | Kuhn |
| 9,031,812 B2 | 5/2015 | Roberts et al. |
| 9,037,578 B2 | 5/2015 | Brust et al. |
| 9,039,581 B2 | 5/2015 | Chia et al. |
| 9,039,614 B2 | 5/2015 | Yuen et al. |
| 9,042,596 B2 | 5/2015 | Connor |
| 9,050,498 B2 | 6/2015 | Lu et al. |
| 9,052,798 B1 | 6/2015 | Klassen et al. |
| 9,055,868 B2 | 6/2015 | Islam |
| 9,064,342 B2 | 6/2015 | Yuen et al. |
| 9,069,380 B2 | 6/2015 | Rahman et al. |
| 9,072,930 B2 | 7/2015 | Ashby et al. |
| 9,083,826 B2 | 7/2015 | Lu et al. |

(56) References Cited

U.S. PATENT DOCUMENTS

| | | |
|---|---|---|
| 9,084,912 B2 | 7/2015 | Jaquish et al. |
| 9,089,733 B2 | 7/2015 | Fisbein et al. |
| 9,107,586 B2 | 8/2015 | Tran |
| 9,114,275 B2 | 8/2015 | Lu et al. |
| 9,119,983 B2 | 9/2015 | Rhea |
| 9,123,317 B2 | 9/2015 | Watterson et al. |
| 9,123,380 B2 | 9/2015 | Holtz et al. |
| 9,128,981 B1 | 9/2015 | Geer |
| 9,135,347 B2 | 9/2015 | Damman et al. |
| 9,137,309 B2 | 9/2015 | Ananny et al. |
| 9,138,614 B2 | 9/2015 | Lu et al. |
| 9,138,615 B2 | 9/2015 | Olson et al. |
| 9,141,087 B2 | 9/2015 | Brown et al. |
| 9,143,881 B2 | 9/2015 | Fan et al. |
| 9,144,709 B2 | 9/2015 | Reich |
| 9,146,147 B1 | 9/2015 | Bakhsh |
| 9,162,142 B2 | 10/2015 | Shum et al. |
| 9,168,001 B2 | 10/2015 | Stivoric et al. |
| 9,173,593 B2 | 11/2015 | Banet et al. |
| 9,173,594 B2 | 11/2015 | Banet et al. |
| 9,174,084 B2 | 11/2015 | Morris et al. |
| 9,174,085 B2 | 11/2015 | Foley |
| 9,178,635 B2 | 11/2015 | Ben-Shlomo |
| 9,183,498 B2 | 11/2015 | Landers |
| 9,186,549 B2 | 11/2015 | Watterson et al. |
| 9,189,021 B2 | 11/2015 | Jerauld |
| 9,192,816 B2 | 11/2015 | Molyneux et al. |
| 9,201,405 B2 | 12/2015 | Clarkson et al. |
| 9,205,301 B2 | 12/2015 | Cohen |
| 9,208,764 B2 | 12/2015 | Ghosh et al. |
| 9,211,440 B2 | 12/2015 | Lagree |
| 9,213,803 B2 | 12/2015 | Rolley |
| 9,223,936 B2 | 12/2015 | Aragones et al. |
| 9,224,291 B2 | 12/2015 | Moll-Carrillo et al. |
| 9,229,476 B2 | 1/2016 | Yanev et al. |
| 9,230,064 B2 | 1/2016 | Yanev et al. |
| 9,233,269 B2 | 1/2016 | Lannon |
| 9,241,635 B2 | 1/2016 | Yuen et al. |
| 9,245,428 B2 | 1/2016 | Weddle et al. |
| 9,247,543 B2 | 1/2016 | Berlin et al. |
| 9,253,168 B2 | 2/2016 | Panther |
| 9,254,099 B2 | 2/2016 | Connor |
| 9,256,910 B2 | 2/2016 | Goldberg |
| 9,257,054 B2 | 2/2016 | Coza et al. |
| 9,258,670 B2 | 2/2016 | Goyal et al. |
| 9,259,633 B2 | 2/2016 | Meyers |
| 9,262,064 B2 | 2/2016 | Yanev et al. |
| 9,269,119 B2 | 2/2016 | Warner |
| 9,272,183 B2 | 3/2016 | Quy |
| 9,272,186 B2 | 3/2016 | Reich |
| 9,275,617 B2 | 3/2016 | Regnier |
| 9,279,734 B2 | 3/2016 | Walker |
| 9,283,429 B2 | 3/2016 | Aragones et al. |
| 9,288,298 B2 | 3/2016 | Choudhary et al. |
| 9,295,422 B2 | 3/2016 | Tai |
| 9,295,894 B2 | 3/2016 | Papadopolous |
| 9,305,141 B2 | 4/2016 | Fabrizio |
| 9,317,662 B2 | 4/2016 | Bangera et al. |
| 9,318,030 B2 | 4/2016 | Harris et al. |
| 9,329,053 B2 | 5/2016 | Lakovic et al. |
| 9,332,363 B2 | 5/2016 | Jain et al. |
| 9,339,209 B2 | 5/2016 | Banet et al. |
| 9,339,691 B2 | 5/2016 | Brammer |
| 9,339,692 B2 | 5/2016 | Hashish |
| 9,345,947 B2 | 5/2016 | Harris et al. |
| 9,349,280 B2 | 5/2016 | Baldwin et al. |
| 9,350,598 B2 | 5/2016 | Barak et al. |
| 9,357,551 B2 | 5/2016 | Gutman |
| 9,357,921 B2 | 6/2016 | Chang et al. |
| 9,358,422 B2 | 6/2016 | Brontman |
| 9,358,426 B2 | 6/2016 | Aragones et al. |
| 9,364,158 B2 | 6/2016 | Banet et al. |
| 9,364,714 B2 | 6/2016 | Koduri et al. |
| 9,367,668 B2 | 6/2016 | Flynt et al. |
| 9,370,679 B2 | 6/2016 | Lagree et al. |
| 9,374,279 B2 | 6/2016 | Yuen et al. |
| 9,375,629 B2 | 6/2016 | Schieffer et al. |
| 9,377,314 B2 | 6/2016 | Tseng et al. |
| 9,378,336 B2 | 6/2016 | Ohnemus et al. |
| 9,381,420 B2 | 7/2016 | Burroughs |
| 9,381,445 B2 | 7/2016 | Ventura et al. |
| 9,385,810 B2 | 7/2016 | Hazani |
| 9,389,057 B2 | 7/2016 | Meschter et al. |
| 9,389,718 B1 | 7/2016 | Letourneur |
| 9,389,754 B2 | 7/2016 | Reese et al. |
| 9,390,229 B1 | 7/2016 | Kahn et al. |
| 9,392,941 B2 | 7/2016 | Powch et al. |
| 9,395,754 B2 | 7/2016 | Cronin |
| 9,401,078 B2 | 7/2016 | Barrett |
| 9,403,048 B2 | 8/2016 | Balandis et al. |
| 9,403,053 B2 | 8/2016 | Kaiser et al. |
| 9,405,892 B2 | 8/2016 | Baldwin et al. |
| 9,409,052 B2 | 8/2016 | Werner |
| 9,411,936 B2 | 8/2016 | Landrum et al. |
| 9,411,940 B2 | 8/2016 | Burroughs et al. |
| 9,420,083 B2 | 8/2016 | Roberts et al. |
| 9,420,542 B2 | 8/2016 | Henia |
| 9,421,422 B2 | 8/2016 | Yuen et al. |
| 9,421,448 B2 | 8/2016 | Tropper et al. |
| 9,422,018 B2 | 8/2016 | Pelot et al. |
| 9,430,043 B1 | 8/2016 | Amento et al. |
| 9,430,920 B2 | 8/2016 | Munro et al. |
| 9,439,574 B2 | 9/2016 | McCombie et al. |
| 9,440,134 B2 | 9/2016 | Nicora |
| 9,442,100 B2 | 9/2016 | Connor |
| 9,446,288 B1 | 9/2016 | Pazan |
| 9,451,897 B2 | 9/2016 | Mazar et al. |
| 9,452,320 B2 | 9/2016 | Yang |
| 9,455,784 B2 | 9/2016 | Cune et al. |
| 9,457,256 B2 | 10/2016 | Aragones et al. |
| 9,460,421 B2 | 10/2016 | Lai et al. |
| 9,462,844 B2 | 10/2016 | Schrock et al. |
| 9,463,572 B2 | 10/2016 | Parente |
| 9,468,382 B2 | 10/2016 | Hanoun |
| 9,468,793 B2 | 10/2016 | Salmon |
| 9,468,794 B2 | 10/2016 | Barton |
| 9,473,593 B2 | 10/2016 | Wallace |
| 9,474,925 B1 | 10/2016 | Hsiung |
| 9,474,935 B2 | 10/2016 | Abbondanza et al. |
| 9,477,303 B2 | 10/2016 | Fleischmann et al. |
| 9,486,070 B2 | 11/2016 | Labrosse et al. |
| 9,486,382 B1 | 11/2016 | Boss |
| 9,491,562 B2 | 11/2016 | Cronin |
| 9,495,015 B1 | 11/2016 | Kahn et al. |
| 9,495,860 B2 | 11/2016 | Lett |
| 9,498,066 B2 | 11/2016 | Christianson et al. |
| 9,498,704 B1 | 11/2016 | Cohen et al. |
| 9,500,464 B2 | 11/2016 | Coza |
| 9,504,414 B2 | 11/2016 | Coza et al. |
| 9,509,269 B1 | 11/2016 | Rosenberg |
| 9,511,259 B2 | 12/2016 | Mountain |
| 9,517,378 B2 | 12/2016 | Ashby et al. |
| 9,517,406 B2 | 12/2016 | Shum et al. |
| 9,529,385 B2 | 12/2016 | Connor |
| 9,529,437 B2 | 12/2016 | Kahn et al. |
| 9,532,002 B2 | 12/2016 | Glass et al. |
| 9,532,734 B2 | 1/2017 | Hoffman et al. |
| 9,533,228 B2 | 1/2017 | Dugan |
| 9,535,505 B2 | 1/2017 | Erkkila et al. |
| 9,536,449 B2 | 1/2017 | Connor |
| 9,539,458 B1 | 1/2017 | Ross |
| 9,545,535 B2 | 1/2017 | Lagree |
| 9,545,541 B2 | 1/2017 | Aragones et al. |
| 9,549,585 B2 | 1/2017 | Amos et al. |
| 9,563,336 B2 | 2/2017 | Barak et al. |
| 9,563,700 B2 | 2/2017 | Barak et al. |
| 9,579,534 B2 | 2/2017 | Sutkowski et al. |
| 9,582,071 B2 | 2/2017 | Baldwin et al. |
| 9,585,563 B2 | 3/2017 | Mensinger et al. |
| 9,586,090 B2 | 3/2017 | Watterson et al. |
| 9,589,482 B2 | 3/2017 | Baldwin et al. |
| 9,594,433 B2 | 3/2017 | Baldwin et al. |
| 9,597,540 B2 | 3/2017 | Arnold |
| 9,599,981 B2 | 3/2017 | Crabtree |

(56) References Cited

U.S. PATENT DOCUMENTS

| | | |
|---|---|---|
| 9,600,079 B2 | 3/2017 | Baldwin et al. |
| 9,602,210 B2 | 3/2017 | Berlin et al. |
| 9,604,096 B2 | 3/2017 | Arnold et al. |
| 9,604,099 B2 | 3/2017 | Taylor |
| 9,610,475 B1 | 4/2017 | DeKnock et al. |
| 9,610,506 B2 | 4/2017 | Dugan |
| 9,615,215 B2 | 4/2017 | Yuen et al. |
| 9,615,785 B2 | 4/2017 | Rocker et al. |
| 9,616,281 B2 | 4/2017 | Hsiung |
| 9,621,959 B2 | 4/2017 | Mountain |
| 9,622,537 B2 | 4/2017 | Amos et al. |
| 9,623,286 B1 | 4/2017 | Chen |
| 9,628,286 B1 | 4/2017 | Nguyen et al. |
| 9,632,746 B2 | 4/2017 | Keipert et al. |
| 9,636,543 B2 | 5/2017 | Dyer et al. |
| 9,636,567 B2 | 5/2017 | Brammer et al. |
| 9,642,764 B2 | 5/2017 | Kuehne et al. |
| 9,646,137 B2 | 5/2017 | Gilley et al. |
| 9,646,481 B2 | 5/2017 | Messenger et al. |
| 9,647,758 B2 | 5/2017 | Hazani |
| 9,655,053 B2 | 5/2017 | Park et al. |
| 9,658,066 B2 | 5/2017 | Yuen et al. |
| 9,661,355 B2 | 5/2017 | Ho |
| 9,661,781 B2 | 5/2017 | Anolik et al. |
| 9,669,261 B2 | 6/2017 | Eder |
| 9,672,196 B2 | 6/2017 | Shachar et al. |
| 9,672,754 B2 | 6/2017 | Yuen et al. |
| 9,673,904 B2 | 6/2017 | Palanisamy et al. |
| 9,678,626 B2 | 6/2017 | Whang |
| 9,681,313 B2 | 6/2017 | Malach |
| 9,682,306 B2 | 6/2017 | Lin et al. |
| 9,687,689 B2 | 6/2017 | Lin |
| 9,692,844 B2 | 6/2017 | Messenger et al. |
| RE46,481 E | 7/2017 | Sako et al. |
| 9,694,247 B2 | 7/2017 | Nurnberg |
| 9,697,740 B2 | 7/2017 | Zhang et al. |
| 9,700,802 B2 | 7/2017 | Dugan |
| 9,701,530 B2 | 7/2017 | Kline |
| 9,707,447 B1 | 7/2017 | Lopez Babodilla |
| 9,710,711 B2 | 7/2017 | Dibenedetto et al. |
| 9,712,629 B2 | 7/2017 | Molettiere et al. |
| 9,713,739 B2 | 7/2017 | Dalmia |
| 9,715,774 B2 | 7/2017 | Baldwin et al. |
| 9,719,797 B2 | 8/2017 | Fino et al. |
| 9,720,443 B2 | 8/2017 | Malhotra |
| 9,723,393 B2 | 8/2017 | Nguyen et al. |
| 9,724,563 B2 | 8/2017 | Schmidt |
| 9,724,589 B2 | 8/2017 | Baudhuin |
| 9,728,059 B2 | 8/2017 | Arnold et al. |
| 9,729,921 B2 | 8/2017 | Kim et al. |
| 9,729,989 B2 | 8/2017 | Marten |
| 9,730,025 B2 | 8/2017 | Yuen et al. |
| 9,730,228 B2 | 8/2017 | Harel |
| 9,730,619 B2 | 8/2017 | Messenger et al. |
| 9,734,184 B1 | 8/2017 | Lagace et al. |
| 9,737,261 B2 | 8/2017 | Coza et al. |
| 9,743,861 B2 | 8/2017 | Giedwoyn et al. |
| 9,756,895 B2 | 9/2017 | Rice et al. |
| 9,757,605 B2 | 9/2017 | Olson et al. |
| 9,757,611 B1 | 9/2017 | Colburn |
| 9,763,581 B2 | 9/2017 | Bonutti et al. |
| 9,767,212 B2 | 9/2017 | Lavi et al. |
| 9,769,522 B2 | 9/2017 | Richardson |
| 9,772,612 B2 | 9/2017 | McCarthy, III et al. |
| 9,775,123 B2 | 9/2017 | Harel |
| 9,776,039 B1 | 10/2017 | Xu |
| 9,776,042 B2 | 10/2017 | Prokhorov |
| 9,778,280 B2 | 10/2017 | Yuen et al. |
| 9,782,125 B2 | 10/2017 | Berner, Jr. et al. |
| 9,782,625 B1 | 10/2017 | Blum et al. |
| 9,789,362 B1 | 10/2017 | Su et al. |
| 9,792,361 B1 | 10/2017 | Geer |
| 9,795,828 B2 | 10/2017 | Andrade |
| 9,797,920 B2 | 10/2017 | Kahn et al. |
| 9,798,309 B2 | 10/2017 | Tirpak |
| 9,801,547 B2 | 10/2017 | Yuen et al. |
| 9,802,081 B2 | 10/2017 | Ridgel et al. |
| 9,808,202 B2 | 11/2017 | Wu et al. |
| 9,808,673 B2 | 11/2017 | Robinson |
| 9,811,639 B2 | 11/2017 | Aragones et al. |
| 9,814,920 B1 | 11/2017 | Monterrey |
| 9,814,928 B2 | 11/2017 | Taylor |
| 9,814,930 B2 | 11/2017 | Manzke et al. |
| 9,818,285 B2 | 11/2017 | Clarke et al. |
| 9,819,561 B2 | 11/2017 | Freishtat et al. |
| 9,819,754 B2 | 11/2017 | Park et al. |
| 9,821,191 B2 | 11/2017 | Abbondanza |
| 9,821,212 B2 | 11/2017 | Kolman et al. |
| 9,824,110 B2 | 11/2017 | Giudici et al. |
| 9,824,578 B2 | 11/2017 | Burton et al. |
| 9,829,327 B2 | 11/2017 | Nagy et al. |
| 9,833,141 B2 | 12/2017 | Kampman et al. |
| 9,833,658 B2 | 12/2017 | Wiener et al. |
| 9,838,736 B2 | 12/2017 | Smith et al. |
| 9,841,077 B2 | 12/2017 | Modrezejewski et al. |
| 9,849,333 B2 | 12/2017 | Fung |
| 9,849,361 B2 | 12/2017 | Coza et al. |
| 9,852,271 B2 | 12/2017 | Aragones et al. |
| 9,858,307 B2 | 1/2018 | Sultan et al. |
| 9,861,300 B2 | 1/2018 | Gettelman et al. |
| 9,864,844 B2 | 1/2018 | Durham et al. |
| 9,866,596 B2 | 1/2018 | Das et al. |
| 9,880,805 B1 | 1/2018 | Guralnick |
| 9,881,326 B2 | 1/2018 | Gilley et al. |
| 9,882,736 B2 | 1/2018 | Lett |
| 9,882,992 B2 | 1/2018 | Baldwin et al. |
| 9,886,309 B2 | 2/2018 | Alles et al. |
| 9,886,871 B1 | 2/2018 | Rauhala et al. |
| 9,892,417 B2 | 2/2018 | Shachar et al. |
| 9,901,772 B2 | 2/2018 | Crowley et al. |
| 9,901,780 B2 | 2/2018 | DeLuca et al. |
| 9,906,572 B2 | 2/2018 | Wang et al. |
| 9,907,396 B1 | 3/2018 | Labrosse et al. |
| 9,910,498 B2 | 3/2018 | Kutliroff et al. |
| 9,914,003 B2 | 3/2018 | Kuehne et al. |
| 9,919,198 B2 | 3/2018 | Romeo et al. |
| 9,921,726 B1 | 3/2018 | Sculley et al. |
| 9,940,161 B1 | 4/2018 | Kahn et al. |
| 9,940,682 B2 | 4/2018 | Hoffman et al. |
| 9,943,159 B1 | 4/2018 | Novikova |
| 9,943,719 B2 | 4/2018 | Smith et al. |
| 9,943,722 B2 | 4/2018 | Dalebout |
| 9,946,857 B2 | 4/2018 | Beals |
| 9,948,349 B2 | 4/2018 | Malach |
| 9,948,477 B2 | 4/2018 | Marten |
| 9,950,209 B2 | 4/2018 | Yim et al. |
| 9,959,902 B2 | 5/2018 | McNamee |
| 9,960,980 B2 | 5/2018 | Wilson |
| 9,962,081 B2 | 5/2018 | Mensinger et al. |
| 9,962,305 B2 | 5/2018 | Yamada et al. |
| 9,962,576 B2 | 5/2018 | Anderson |
| 9,965,059 B2 | 5/2018 | Myers et al. |
| 9,967,614 B2 | 5/2018 | McCarthy, III |
| 9,974,997 B2 | 5/2018 | Cei |
| 9,977,874 B2 | 5/2018 | Aragones et al. |
| 9,983,011 B2 | 5/2018 | Mountain |
| 9,986,315 B2 | 5/2018 | Oleson et al. |
| 9,987,513 B2 | 6/2018 | Yim et al. |
| 9,989,507 B2 | 6/2018 | Benn |
| 9,996,066 B2 | 6/2018 | Beals |
| 10,004,656 B2 | 6/2018 | Whalen et al. |
| 10,004,940 B2 | 6/2018 | Badarneh |
| 10,008,090 B2 | 6/2018 | Yuen et al. |
| 10,013,986 B1 | 7/2018 | Bhaya et al. |
| 10,015,216 B2 | 7/2018 | Wang et al. |
| 10,016,655 B2 | 7/2018 | Lagree |
| 10,021,188 B2 | 7/2018 | Oleson et al. |
| 10,022,589 B2 | 7/2018 | Case, Jr. et al. |
| 10,022,590 B2 | 7/2018 | Foley et al. |
| 10,029,172 B2 | 7/2018 | Galasso et al. |
| 10,035,010 B1 | 7/2018 | Wagstaff |
| 10,037,053 B2 | 7/2018 | Malhotra |
| 10,038,952 B2 | 7/2018 | Labrosse et al. |
| 2001/0001303 A1 | 5/2001 | Ohsuga et al. |

(56) References Cited

U.S. PATENT DOCUMENTS

| | | |
|---|---|---|
| 2001/0027266 A1 | 10/2001 | Hautala |
| 2001/0028350 A1 | 10/2001 | Matsuoka et al. |
| 2001/0049320 A1 | 12/2001 | Cohen |
| 2001/0049470 A1 | 12/2001 | Mault et al. |
| 2001/0053883 A1 | 12/2001 | Yoshimura et al. |
| 2002/0004191 A1 | 1/2002 | Tice et al. |
| 2002/0004439 A1 | 1/2002 | Galbraith et al. |
| 2002/0013717 A1 | 1/2002 | Ando |
| 2002/0016235 A1 | 2/2002 | Ashby et al. |
| 2002/0022551 A1 | 2/2002 | Watterson et al. |
| 2002/0022555 A1 | 2/2002 | Nesci |
| 2002/0024521 A1 | 2/2002 | Goden |
| 2002/0026292 A1 | 2/2002 | Isami |
| 2002/0031756 A1 | 3/2002 | Holtz |
| 2002/0039952 A1 | 4/2002 | Clem |
| 2002/0042328 A1 | 4/2002 | Yoo |
| 2002/0042912 A1 | 4/2002 | Iijima |
| 2002/0045519 A1 | 4/2002 | Watterson |
| 2002/0047867 A1 | 4/2002 | Mault |
| 2002/0054244 A1 | 5/2002 | Holtz |
| 2002/0055419 A1 | 5/2002 | Hinnebusch |
| 2002/0055422 A1 | 5/2002 | Airmet |
| 2002/0055857 A1 | 5/2002 | Mault |
| 2002/0060335 A1 | 5/2002 | Edgar |
| 2002/0062236 A1 | 5/2002 | Murashita |
| 2002/0068887 A1 | 6/2002 | Kikumoto |
| 2002/0068991 A1 | 6/2002 | Fitzsimmons, Jr. |
| 2002/0070954 A1 | 6/2002 | Lang |
| 2002/0077219 A1 | 6/2002 | Cohen |
| 2002/0077221 A1 | 6/2002 | Dalebout et al. |
| 2002/0083122 A1 | 6/2002 | Lemchen |
| 2002/0086779 A1 | 7/2002 | Wilkinson |
| 2002/0088337 A1 | 7/2002 | Devecka |
| 2002/0091043 A1 | 7/2002 | Rexach |
| 2002/0091796 A1 | 7/2002 | Higginson |
| 2002/0106617 A1 | 8/2002 | Hersh |
| 2002/0107058 A1 | 8/2002 | Namba et al. |
| 2002/0109710 A1 | 8/2002 | Holtz et al. |
| 2002/0111541 A1 | 8/2002 | Bibl et al. |
| 2002/0115536 A1 | 8/2002 | Hojo |
| 2002/0116266 A1 | 8/2002 | Marshall |
| 2002/0128119 A1 | 9/2002 | Arai |
| 2002/0138023 A1 | 9/2002 | Kume et al. |
| 2002/0142887 A1 | 10/2002 | O'Malley |
| 2002/0151413 A1 | 10/2002 | Dalebout |
| 2002/0155416 A1 | 10/2002 | Barton |
| 2002/0156351 A1 | 10/2002 | Sagel |
| 2002/0156387 A1 | 10/2002 | Dardik |
| 2002/0160883 A1 | 10/2002 | Dugan |
| 2002/0164929 A1 | 11/2002 | Pinson |
| 2002/0169634 A1 | 11/2002 | Nishi |
| 2002/0173407 A1 | 11/2002 | Bowman |
| 2002/0194604 A1 | 12/2002 | Sanchez et al. |
| 2002/0198776 A1 | 12/2002 | Nara |
| 2003/0004424 A1 | 1/2003 | Birnbaum |
| 2003/0013072 A1 | 1/2003 | Thomas |
| 2003/0021273 A1 | 1/2003 | Fouquet |
| 2003/0033600 A1 | 2/2003 | Cliff et al. |
| 2003/0040348 A1 | 2/2003 | Martens |
| 2003/0041076 A1 | 2/2003 | Lucovsky |
| 2003/0043986 A1 | 3/2003 | Creamer et al. |
| 2003/0043989 A1 | 3/2003 | Creamer et al. |
| 2003/0044021 A1 | 3/2003 | Wilkinson |
| 2003/0063133 A1 | 4/2003 | Foote et al. |
| 2003/0065561 A1 | 4/2003 | Brown et al. |
| 2003/0069108 A1 | 4/2003 | Rubinstein |
| 2003/0078138 A1 | 4/2003 | Toyama |
| 2003/0088196 A1 | 5/2003 | Steve |
| 2003/0092540 A1 | 5/2003 | Gillen |
| 2003/0100406 A1 | 5/2003 | Millington |
| 2003/0104907 A1 | 6/2003 | Sankrithi |
| 2003/0105390 A1 | 6/2003 | Alessandri |
| 2003/0115157 A1 | 6/2003 | Circenis |
| 2003/0125165 A1 | 7/2003 | Trevino |
| 2003/0126593 A1 | 7/2003 | Mault |
| 2003/0134714 A1 | 7/2003 | Oishi et al. |
| 2003/0138761 A1 | 7/2003 | Pesnell |
| 2003/0139254 A1 | 7/2003 | Chang |
| 2003/0142951 A1 | 7/2003 | Tsurugai |
| 2003/0148857 A1 | 8/2003 | Yu |
| 2003/0149344 A1 | 8/2003 | Nizan |
| 2003/0153436 A1 | 8/2003 | Ho |
| 2003/0158014 A1 | 8/2003 | Valentin-Sivico |
| 2003/0163287 A1 | 8/2003 | Vock et al. |
| 2003/0165802 A1 | 9/2003 | Murphy |
| 2003/0166434 A1 | 9/2003 | Lopez-Santillana et al. |
| 2003/0171189 A1 | 9/2003 | Kaufman |
| 2003/0171190 A1 | 9/2003 | Rice |
| 2003/0171192 A1 | 9/2003 | Wu |
| 2003/0176815 A1 | 9/2003 | Baba et al. |
| 2003/0181291 A1 | 9/2003 | Ogawa |
| 2003/0195089 A1 | 10/2003 | Schroeder |
| 2003/0207237 A1 | 11/2003 | Glezerman |
| 2003/0208113 A1 | 11/2003 | Mault et al. |
| 2003/0211449 A1 | 11/2003 | Seiller |
| 2003/0211916 A1 | 11/2003 | Capuano |
| 2003/0212536 A1 | 11/2003 | Wang |
| 2003/0214530 A1 | 11/2003 | Wang |
| 2003/0216228 A1 | 11/2003 | Rast |
| 2003/0220143 A1 | 11/2003 | Shteyn et al. |
| 2003/0224337 A1 | 12/2003 | Shum et al. |
| 2003/0227473 A1 | 12/2003 | Shih |
| 2003/0232707 A1 | 12/2003 | Dalebout et al. |
| 2004/0005959 A1 | 1/2004 | Takizawa |
| 2004/0005961 A1 | 1/2004 | Iund |
| 2004/0008220 A1 | 1/2004 | Snyder et al. |
| 2004/0010420 A1 | 1/2004 | Rooks |
| 2004/0012335 A1 | 1/2004 | Shon et al. |
| 2004/0014014 A1 | 1/2004 | Hess |
| 2004/0018915 A1 | 1/2004 | Reyes |
| 2004/0019654 A1 | 1/2004 | Powers |
| 2004/0027368 A1 | 2/2004 | Snyder et al. |
| 2004/0030762 A1 | 2/2004 | Silverthorne |
| 2004/0046692 A1 | 3/2004 | Robson |
| 2004/0051392 A1 | 3/2004 | Badarneh |
| 2004/0054350 A1 | 3/2004 | Shaughnessy |
| 2004/0063549 A1 | 4/2004 | Kuo |
| 2004/0072652 A1 | 4/2004 | Alessandri et al. |
| 2004/0077462 A1 | 4/2004 | Brown |
| 2004/0077975 A1 | 4/2004 | Zimmerman |
| 2004/0078208 A1 | 4/2004 | Burwell |
| 2004/0082444 A1 | 4/2004 | Golesh |
| 2004/0092367 A1 | 5/2004 | Corbalis |
| 2004/0095516 A1 | 5/2004 | Rohlicek |
| 2004/0097331 A1 | 5/2004 | Zillig |
| 2004/0102931 A1 | 5/2004 | Ellis |
| 2004/0103146 A1 | 5/2004 | Park |
| 2004/0116837 A1 | 6/2004 | Yamaguchi |
| 2004/0116899 A1 | 6/2004 | Shaughnessy |
| 2004/0117072 A1 | 6/2004 | Takeda |
| 2004/0117214 A1 | 6/2004 | Shea |
| 2004/0127285 A1 | 7/2004 | Kavana |
| 2004/0127334 A1 | 7/2004 | Heppert |
| 2004/0127335 A1 | 7/2004 | Watterson |
| 2004/0127336 A1 | 7/2004 | Lapcevic |
| 2004/0157546 A1 | 8/2004 | Fantaay |
| 2004/0160336 A1 | 8/2004 | Hoch |
| 2004/0162188 A1 | 8/2004 | Watterson |
| 2004/0162189 A1 | 8/2004 | Hickman |
| 2004/0162702 A1 | 8/2004 | Pandipati et al. |
| 2004/0171460 A1 | 9/2004 | Park |
| 2004/0171464 A1 | 9/2004 | Ashby et al. |
| 2004/0171465 A1 | 9/2004 | Hald |
| 2004/0180719 A1 | 9/2004 | Feldman |
| 2004/0186390 A1 | 9/2004 | Ross et al. |
| 2004/0198555 A1 | 10/2004 | Anderson |
| 2004/0208943 A1 | 10/2004 | Miketin |
| 2004/0210661 A1 | 10/2004 | Thompson |
| 2004/0214693 A1 | 10/2004 | Piaget et al. |
| 2004/0215958 A1 | 10/2004 | Ellis |
| 2004/0220017 A1 | 11/2004 | Gordon |
| 2004/0224740 A1 | 11/2004 | Ball et al. |
| 2004/0225239 A1 | 11/2004 | Yamamoto |
| 2004/0225532 A1 | 11/2004 | Gadiyak |

(56) References Cited

U.S. PATENT DOCUMENTS

| | | |
|---|---|---|
| 2004/0229730 A1 | 11/2004 | Ainsworth et al. |
| 2004/0230138 A1 | 11/2004 | Inoue et al. |
| 2004/0242388 A1 | 12/2004 | Kusminsky |
| 2004/0248713 A1 | 12/2004 | Campanaro |
| 2005/0003338 A1 | 1/2005 | Norcott et al. |
| 2005/0003931 A1 | 1/2005 | Mills et al. |
| 2005/0008992 A1 | 1/2005 | Westergaard et al. |
| 2005/0009668 A1 | 1/2005 | Savettiere |
| 2005/0012622 A1 | 1/2005 | Sutton |
| 2005/0013433 A1 | 1/2005 | Ghassabian |
| 2005/0014571 A1 | 1/2005 | Varner |
| 2005/0015281 A1 | 1/2005 | Clark et al. |
| 2005/0020887 A1 | 1/2005 | Goldberg |
| 2005/0026750 A1 | 2/2005 | Oglesby et al. |
| 2005/0026811 A1 | 2/2005 | Mjalli |
| 2005/0037898 A1 | 2/2005 | Chang |
| 2005/0038698 A1 | 2/2005 | Lukose |
| 2005/0038699 A1 | 2/2005 | Lillibridge |
| 2005/0043145 A1 | 2/2005 | Anderson et al. |
| 2005/0044210 A1 | 2/2005 | Ku |
| 2005/0048461 A1 | 3/2005 | Lahteenmaki |
| 2005/0049121 A1 | 3/2005 | Dalebout |
| 2005/0054492 A1 | 3/2005 | Neff |
| 2005/0054940 A1 | 3/2005 | Almen |
| 2005/0060238 A1 | 3/2005 | Gravina et al. |
| 2005/0062841 A1 | 3/2005 | Rivera-Cintron |
| 2005/0064994 A1 | 3/2005 | Matsumoto |
| 2005/0071462 A1 | 3/2005 | Bodin et al. |
| 2005/0071463 A1 | 3/2005 | Bodin et al. |
| 2005/0075213 A1 | 4/2005 | Arick |
| 2005/0075222 A1 | 4/2005 | Adley |
| 2005/0075903 A1 | 4/2005 | Piccionelli |
| 2005/0079905 A1 | 4/2005 | Martens |
| 2005/0085352 A1 | 4/2005 | Baxter |
| 2005/0102172 A1 | 5/2005 | Sirmans, Jr. |
| 2005/0107216 A1 | 5/2005 | Lee et al. |
| 2005/0107723 A1 | 5/2005 | Wehman et al. |
| 2005/0107726 A1 | 5/2005 | Oyen |
| 2005/0112601 A1 | 5/2005 | Hassibi |
| 2005/0113158 A1 | 5/2005 | Sterchi et al. |
| 2005/0113652 A1 | 5/2005 | Stark et al. |
| 2005/0113723 A1 | 5/2005 | Ueyama |
| 2005/0124463 A1 | 6/2005 | Yeo et al. |
| 2005/0124471 A1 | 6/2005 | Wilkinson |
| 2005/0131319 A1 | 6/2005 | Der Meer |
| 2005/0143226 A1 | 6/2005 | Heidecke |
| 2005/0148442 A1 | 7/2005 | Watterson |
| 2005/0159277 A1 | 7/2005 | Mcvay |
| 2005/0159278 A1 | 7/2005 | Mcvay |
| 2005/0159712 A1 | 7/2005 | Andersen |
| 2005/0160141 A1 | 7/2005 | Galley |
| 2005/0164832 A1 | 7/2005 | Maschke |
| 2005/0164838 A1 | 7/2005 | Watterson |
| 2005/0164839 A1 | 7/2005 | Watterson |
| 2005/0167907 A1 | 8/2005 | Curkendall et al. |
| 2005/0172311 A1 | 8/2005 | Hjelt et al. |
| 2005/0178210 A1 | 8/2005 | Lanham |
| 2005/0181347 A1 | 8/2005 | Barnes et al. |
| 2005/0187704 A1 | 8/2005 | Peters |
| 2005/0195094 A1 | 9/2005 | White |
| 2005/0202862 A1 | 9/2005 | Shuman et al. |
| 2005/0209050 A1 | 9/2005 | Bartels |
| 2005/0209051 A1 | 9/2005 | Santomassimo et al. |
| 2005/0209056 A1 | 9/2005 | Daly |
| 2005/0209061 A1 | 9/2005 | Crawford et al. |
| 2005/0209887 A1 | 9/2005 | Pollner |
| 2005/0210169 A1 | 9/2005 | Chou |
| 2005/0212202 A1 | 9/2005 | Meyer |
| 2005/0213442 A1 | 9/2005 | Sako |
| 2005/0215335 A1 | 9/2005 | Marquardt |
| 2005/0215397 A1 | 9/2005 | Watterson |
| 2005/0227811 A1 | 10/2005 | Shum et al. |
| 2005/0228245 A1 | 10/2005 | Quy |
| 2005/0228883 A1 | 10/2005 | Brown |
| 2005/0233859 A1 | 10/2005 | Takai |
| 2005/0233861 A1 | 10/2005 | Hickman |
| 2005/0233866 A1 | 10/2005 | Miyamaru et al. |
| 2005/0238182 A1 | 10/2005 | Shih et al. |
| 2005/0239601 A1 | 10/2005 | Thomas |
| 2005/0240444 A1 | 10/2005 | Wooten |
| 2005/0245370 A1 | 11/2005 | Boland |
| 2005/0245431 A1 | 11/2005 | Demmer et al. |
| 2005/0261609 A1 | 11/2005 | Collings et al. |
| 2005/0269601 A1 | 12/2005 | Tsubaki |
| 2005/0272561 A1 | 12/2005 | Cammerata |
| 2005/0272564 A1 | 12/2005 | Pyles et al. |
| 2005/0272577 A1 | 12/2005 | Olson |
| 2005/0274188 A1 | 12/2005 | Cabanis et al. |
| 2005/0288954 A1 | 12/2005 | McCarthy et al. |
| 2006/0003872 A1 | 1/2006 | Chiles et al. |
| 2006/0004265 A1 | 1/2006 | Pulkkinen et al. |
| 2006/0006005 A1 | 1/2006 | Dumornay |
| 2006/0009332 A1 | 1/2006 | Jones |
| 2006/0013351 A1 | 1/2006 | Crider |
| 2006/0019224 A1 | 1/2006 | Behar et al. |
| 2006/0020174 A1 | 1/2006 | Matsumura |
| 2006/0020556 A1 | 1/2006 | Hamnen |
| 2006/0020990 A1 | 1/2006 | McEneaney |
| 2006/0034161 A1 | 2/2006 | Muller |
| 2006/0035758 A1 | 2/2006 | Rogozinski |
| 2006/0035768 A1 | 2/2006 | Kowallis |
| 2006/0035774 A1 | 2/2006 | Marks |
| 2006/0040244 A1 | 2/2006 | Kain |
| 2006/0040246 A1 | 2/2006 | Ding et al. |
| 2006/0040793 A1 | 2/2006 | Martens |
| 2006/0046807 A1 | 3/2006 | Sanchez |
| 2006/0046898 A1 | 3/2006 | Harvey |
| 2006/0046905 A1 | 3/2006 | Doody, Jr. |
| 2006/0058155 A1 | 3/2006 | Kumar |
| 2006/0063644 A1 | 3/2006 | Yang |
| 2006/0063980 A1 | 3/2006 | Hwang et al. |
| 2006/0069102 A1 | 3/2006 | Leban et al. |
| 2006/0079800 A1 | 4/2006 | Martikka et al. |
| 2006/0084551 A1 | 4/2006 | Volpe, Jr. |
| 2006/0084851 A1 | 4/2006 | Lee et al. |
| 2006/0089238 A1 | 4/2006 | Huang et al. |
| 2006/0094569 A1 | 5/2006 | Day |
| 2006/0094570 A1 | 5/2006 | Schneider |
| 2006/0097453 A1 | 5/2006 | Feldman |
| 2006/0100546 A1 | 5/2006 | Silk |
| 2006/0104047 A1 | 5/2006 | Guzman |
| 2006/0105888 A1 | 5/2006 | Piane, Jr. |
| 2006/0111944 A1 | 5/2006 | Sirmans, Jr. |
| 2006/0116558 A1 | 6/2006 | Jang |
| 2006/0122034 A1 | 6/2006 | Chen |
| 2006/0122035 A1 | 6/2006 | Felix |
| 2006/0122468 A1 | 6/2006 | Tavor |
| 2006/0122474 A1 | 6/2006 | Teller et al. |
| 2006/0128534 A1 | 6/2006 | Roque |
| 2006/0129432 A1 | 6/2006 | Choi et al. |
| 2006/0142665 A1 | 6/2006 | Garay et al. |
| 2006/0155576 A1 | 7/2006 | Deluz |
| 2006/0160639 A1 | 7/2006 | Klein |
| 2006/0160667 A1 | 7/2006 | Oglesby et al. |
| 2006/0161455 A1 | 7/2006 | Anastasia |
| 2006/0161621 A1 | 7/2006 | Rosenberg |
| 2006/0161656 A1 | 7/2006 | Sorvisto |
| 2006/0161850 A1 | 7/2006 | Seaberg |
| 2006/0166737 A1 | 7/2006 | Bentley |
| 2006/0166790 A1 | 7/2006 | Wang |
| 2006/0173556 A1 | 8/2006 | Rosenberg |
| 2006/0173828 A1 | 8/2006 | Rosenberg |
| 2006/0179044 A1 | 8/2006 | Rosenberg |
| 2006/0179056 A1 | 8/2006 | Rosenberg |
| 2006/0183602 A1 | 8/2006 | Astilean |
| 2006/0183980 A1 | 8/2006 | Yang |
| 2006/0184427 A1 | 8/2006 | Singh |
| 2006/0186197 A1 | 8/2006 | Rosenberg |
| 2006/0189439 A1 | 8/2006 | Baudhuin |
| 2006/0189440 A1 | 8/2006 | Gravagne |
| 2006/0189854 A1 | 8/2006 | Webb et al. |
| 2006/0194679 A1 | 8/2006 | Hatcher |
| 2006/0195361 A1 | 8/2006 | Rosenberg |
| 2006/0198613 A1 | 9/2006 | Lee |

(56) References Cited

U.S. PATENT DOCUMENTS

| | | |
|---|---|---|
| 2006/0199155 A1 | 9/2006 | Mosher |
| 2006/0203972 A1 | 9/2006 | Hays |
| 2006/0205349 A1 | 9/2006 | Passier et al. |
| 2006/0205564 A1 | 9/2006 | Peterson |
| 2006/0205569 A1 | 9/2006 | Watterson |
| 2006/0217231 A1 | 9/2006 | Parks et al. |
| 2006/0218253 A1 | 9/2006 | Hays |
| 2006/0223635 A1 | 10/2006 | Rosenberg |
| 2006/0223637 A1 | 10/2006 | Rosenberg |
| 2006/0223674 A1 | 10/2006 | Korkie |
| 2006/0223680 A1 | 10/2006 | Chang |
| 2006/0223681 A1 | 10/2006 | Loane |
| 2006/0224051 A1 | 10/2006 | Teller et al. |
| 2006/0228683 A1 | 10/2006 | Jianping |
| 2006/0229058 A1 | 10/2006 | Rosenberg |
| 2006/0229163 A1 | 10/2006 | Waters |
| 2006/0229164 A1 | 10/2006 | Einav |
| 2006/0234840 A1 | 10/2006 | Watson |
| 2006/0240947 A1 | 10/2006 | Qu |
| 2006/0247095 A1 | 11/2006 | Rummerfield |
| 2006/0247098 A1 | 11/2006 | Raniere |
| 2006/0248965 A1 | 11/2006 | Wyatt |
| 2006/0250524 A1 | 11/2006 | Roche |
| 2006/0251638 A1 | 11/2006 | Guenzler-Pukall |
| 2006/0252600 A1 | 11/2006 | Grogan |
| 2006/0252602 A1 | 11/2006 | Brown |
| 2006/0252608 A1 | 11/2006 | Kang et al. |
| 2006/0253010 A1 | 11/2006 | Brady et al. |
| 2006/0253210 A1 | 11/2006 | Rosenberg |
| 2006/0256007 A1 | 11/2006 | Rosenberg |
| 2006/0256008 A1 | 11/2006 | Rosenberg |
| 2006/0258515 A1 | 11/2006 | Kang et al. |
| 2006/0259275 A1 | 11/2006 | Maschke |
| 2006/0259574 A1 | 11/2006 | Rosenberg |
| 2006/0262752 A1 | 11/2006 | Moore et al. |
| 2006/0264299 A1 | 11/2006 | Farinelli et al. |
| 2006/0264730 A1 | 11/2006 | Stivoric et al. |
| 2006/0265469 A1 | 11/2006 | Estrade |
| 2006/0269251 A1 | 11/2006 | Hsu |
| 2006/0271286 A1 | 11/2006 | Rosenberg |
| 2006/0276306 A1 | 12/2006 | Pan et al. |
| 2006/0281603 A1 | 12/2006 | Hickman |
| 2006/0281605 A1 | 12/2006 | Lo |
| 2006/0283050 A1 | 12/2006 | Carnes et al. |
| 2006/0287089 A1 | 12/2006 | Addington et al. |
| 2006/0293608 A1 | 12/2006 | Rothman et al. |
| 2006/0293617 A1 | 12/2006 | Einav et al. |
| 2007/0000154 A1 | 1/2007 | Dibenedetto |
| 2007/0004562 A1 | 1/2007 | Pan et al. |
| 2007/0004565 A1 | 1/2007 | Gebhardt |
| 2007/0004736 A1 | 1/2007 | Kubo |
| 2007/0005395 A1 | 1/2007 | Singh |
| 2007/0006489 A1 | 1/2007 | Case, Jr. et al. |
| 2007/0011027 A1 | 1/2007 | Melendez |
| 2007/0011391 A1 | 1/2007 | Kim et al. |
| 2007/0011920 A1 | 1/2007 | DiBenedetto et al. |
| 2007/0013655 A1 | 1/2007 | Rosenberg et al. |
| 2007/0014422 A1 | 1/2007 | Wesemann et al. |
| 2007/0015752 A1 | 1/2007 | Hangauer, Jr. |
| 2007/0016444 A1 | 1/2007 | Holkkola |
| 2007/0016930 A1 | 1/2007 | Wesemann et al. |
| 2007/0026958 A1 | 2/2007 | Barasch et al. |
| 2007/0026999 A1 | 2/2007 | Merolle et al. |
| 2007/0027000 A1 | 2/2007 | Shirai et al. |
| 2007/0027003 A1 | 2/2007 | Clark |
| 2007/0028749 A1 | 2/2007 | Basson |
| 2007/0032345 A1 | 2/2007 | Padmanabhan |
| 2007/0032351 A1 | 2/2007 | Reyes |
| 2007/0032481 A1 | 2/2007 | Dvorak |
| 2007/0033012 A1 | 2/2007 | Rosenberg |
| 2007/0033068 A1 | 2/2007 | Rao |
| 2007/0033069 A1 | 2/2007 | Rao |
| 2007/0038038 A1 | 2/2007 | Stivoric et al. |
| 2007/0038137 A1 | 2/2007 | Arand et al. |
| 2007/0038153 A1 | 2/2007 | Basson |
| 2007/0042866 A1 | 2/2007 | Skilken |
| 2007/0042868 A1 | 2/2007 | Fisher |
| 2007/0049384 A1 | 3/2007 | King et al. |
| 2007/0049461 A1 | 3/2007 | Kim et al. |
| 2007/0049462 A1 | 3/2007 | Asukai et al. |
| 2007/0049470 A1 | 3/2007 | Pyles et al. |
| 2007/0051369 A1 | 3/2007 | Choi et al. |
| 2007/0054778 A1 | 3/2007 | Blanarovich |
| 2007/0060408 A1 | 3/2007 | Schultz et al. |
| 2007/0060446 A1 | 3/2007 | Asukai et al. |
| 2007/0060898 A1 | 3/2007 | Shaughnessy |
| 2007/0061314 A1 | 3/2007 | Rosenberg |
| 2007/0063033 A1 | 3/2007 | Silverbrook et al. |
| 2007/0072156 A1 | 3/2007 | Kaufman et al. |
| 2007/0074617 A1 | 4/2007 | Vergo |
| 2007/0075127 A1 | 4/2007 | Rosenberg |
| 2007/0079691 A1 | 4/2007 | Turner |
| 2007/0083095 A1 | 4/2007 | Rippo et al. |
| 2007/0083323 A1 | 4/2007 | Rosenberg |
| 2007/0083975 A1 | 4/2007 | Senegal |
| 2007/0093360 A1 | 4/2007 | Neff |
| 2007/0093369 A1 | 4/2007 | Bocchicchio |
| 2007/0100595 A1 | 5/2007 | Earles |
| 2007/0100666 A1 | 5/2007 | Stivoric et al. |
| 2007/0106484 A1 | 5/2007 | Sweatman et al. |
| 2007/0109491 A1 | 5/2007 | Howell et al. |
| 2007/0111753 A1 | 5/2007 | Vock |
| 2007/0111858 A1 | 5/2007 | Dugan |
| 2007/0117680 A1 | 5/2007 | Neff |
| 2007/0117683 A1 | 5/2007 | Ercanbrack et al. |
| 2007/0117693 A1 | 5/2007 | Ilioi |
| 2007/0122786 A1 | 5/2007 | Relan et al. |
| 2007/0123390 A1 | 5/2007 | Mathis |
| 2007/0124762 A1 | 5/2007 | Chickering et al. |
| 2007/0129220 A1 | 6/2007 | Bardha |
| 2007/0129907 A1 | 6/2007 | Demon |
| 2007/0135264 A1 | 6/2007 | Rosenberg |
| 2007/0135738 A1 | 6/2007 | Bonutti |
| 2007/0136093 A1 | 6/2007 | Rankin et al. |
| 2007/0137307 A1 | 6/2007 | Gruben |
| 2007/0140403 A1 | 6/2007 | Yuguchi et al. |
| 2007/0142175 A1 | 6/2007 | Morgan |
| 2007/0142177 A1 | 6/2007 | Simms et al. |
| 2007/0142179 A1 | 6/2007 | Terao et al. |
| 2007/0146347 A1 | 6/2007 | Rosenberg |
| 2007/0149362 A1 | 6/2007 | Lee et al. |
| 2007/0149364 A1 | 6/2007 | Blau |
| 2007/0150188 A1 | 6/2007 | Rosenberg |
| 2007/0153639 A1 | 7/2007 | Lafever |
| 2007/0155589 A1 | 7/2007 | Feldman |
| 2007/0156335 A1 | 7/2007 | McBride et al. |
| 2007/0161459 A1 | 7/2007 | Watson |
| 2007/0161466 A1 | 7/2007 | Oglesby et al. |
| 2007/0167291 A1 | 7/2007 | Kuo |
| 2007/0167293 A1 | 7/2007 | Nally |
| 2007/0169381 A1 | 7/2007 | Gordon |
| 2007/0173355 A1 | 7/2007 | Klein |
| 2007/0176035 A1 | 8/2007 | Campbell |
| 2007/0179023 A1 | 8/2007 | Dyer |
| 2007/0179359 A1 | 8/2007 | Goodwin |
| 2007/0180737 A1 | 8/2007 | DiBenedetto et al. |
| 2007/0184953 A1 | 8/2007 | Luberski et al. |
| 2007/0189544 A1 | 8/2007 | Rosenberg |
| 2007/0191141 A1 | 8/2007 | Weber |
| 2007/0197193 A1 | 8/2007 | Zhou |
| 2007/0197274 A1 | 8/2007 | Dugan |
| 2007/0197345 A1 | 8/2007 | Wallace et al. |
| 2007/0197346 A1 | 8/2007 | Seliber |
| 2007/0197920 A1 | 8/2007 | Adams |
| 2007/0201727 A1 | 8/2007 | Birrell et al. |
| 2007/0202992 A1 | 8/2007 | Grasshoff |
| 2007/0203004 A1 | 8/2007 | Campanaro et al. |
| 2007/0207733 A1 | 9/2007 | Wong et al. |
| 2007/0208392 A1 | 9/2007 | Kuschner et al. |
| 2007/0208530 A1 | 9/2007 | Vock |
| 2007/0213110 A1 | 9/2007 | Rosenberg |
| 2007/0213126 A1 | 9/2007 | Deutsch et al. |
| 2007/0213178 A1 | 9/2007 | Lemmela |
| 2007/0213183 A1 | 9/2007 | Menektchiev |

(56) References Cited

U.S. PATENT DOCUMENTS

| | | |
|---|---|---|
| 2007/0218432 A1 | 9/2007 | Glass |
| 2007/0219057 A1 | 9/2007 | Fleishman |
| 2007/0219058 A1 | 9/2007 | Fleishman |
| 2007/0219059 A1 | 9/2007 | Schwartz |
| 2007/0219068 A1 | 9/2007 | Korfmacher |
| 2007/0219074 A1 | 9/2007 | Pride |
| 2007/0219457 A1 | 9/2007 | Lo |
| 2007/0225118 A1 | 9/2007 | Giorno |
| 2007/0225119 A1 | 9/2007 | Schenk |
| 2007/0225120 A1 | 9/2007 | Schenk |
| 2007/0232450 A1 | 10/2007 | Hanoun |
| 2007/0232452 A1 | 10/2007 | Ebrom |
| 2007/0232453 A1 | 10/2007 | Ebrom |
| 2007/0232455 A1 | 10/2007 | Ebrom |
| 2007/0232461 A1 | 10/2007 | Jenkins et al. |
| 2007/0232463 A1 | 10/2007 | Wu |
| 2007/0233743 A1 | 10/2007 | Rosenberg |
| 2007/0239479 A1 | 10/2007 | Arrasvuori |
| 2007/0243974 A1 | 10/2007 | Li |
| 2007/0245258 A1 | 10/2007 | Ginggen et al. |
| 2007/0249467 A1 | 10/2007 | Hong et al. |
| 2007/0249468 A1 | 10/2007 | Chen |
| 2007/0254778 A1 | 11/2007 | Ashby |
| 2007/0260482 A1 | 11/2007 | Nurmela |
| 2007/0265146 A1 | 11/2007 | Kowalczewski |
| 2007/0270663 A1 | 11/2007 | Ng et al. |
| 2007/0270721 A1 | 11/2007 | Ananny et al. |
| 2007/0271065 A1 | 11/2007 | Gupta et al. |
| 2007/0271116 A1 | 11/2007 | Wysocki et al. |
| 2007/0271387 A1 | 11/2007 | Lydon et al. |
| 2007/0272011 A1 | 11/2007 | Chapa, Jr. |
| 2007/0275825 A1 | 11/2007 | O'brien |
| 2007/0275826 A1 | 11/2007 | Niemimaki et al. |
| 2007/0275830 A1 | 11/2007 | Lee |
| 2007/0276870 A1 | 11/2007 | Rosenberg |
| 2007/0281828 A1 | 12/2007 | Rice |
| 2007/0283853 A1 | 12/2007 | Sun |
| 2007/0287141 A1 | 12/2007 | Milner |
| 2007/0287597 A1 | 12/2007 | Cameron |
| 2007/0287930 A1 | 12/2007 | Sutton |
| 2007/0288204 A1 | 12/2007 | Gienke et al. |
| 2007/0288251 A1 | 12/2007 | Ebrom et al. |
| 2007/0288331 A1 | 12/2007 | Ebrom et al. |
| 2007/0288476 A1 | 12/2007 | Flanagan, III |
| 2007/0288969 A1 | 12/2007 | Prum |
| 2007/0293781 A1 | 12/2007 | Sims et al. |
| 2007/0298405 A1 | 12/2007 | Ebrom et al. |
| 2007/0298935 A1 | 12/2007 | Badarneh |
| 2008/0004162 A1 | 1/2008 | Chen |
| 2008/0005276 A1 | 1/2008 | Frederick |
| 2008/0009275 A1 | 1/2008 | Werner |
| 2008/0015061 A1 | 1/2008 | Klein |
| 2008/0015087 A1 | 1/2008 | Negrin |
| 2008/0015088 A1 | 1/2008 | Del Monaco |
| 2008/0015089 A1 | 1/2008 | Hurwitz |
| 2008/0020898 A1 | 1/2008 | Pyles et al. |
| 2008/0026838 A1 | 1/2008 | Dunstan et al. |
| 2008/0027337 A1 | 1/2008 | Dugan |
| 2008/0027673 A1 | 1/2008 | Trumm |
| 2008/0032864 A1 | 2/2008 | Hakki |
| 2008/0032865 A1 | 2/2008 | Wu |
| 2008/0032870 A1 | 2/2008 | Wu |
| 2008/0037375 A1 | 2/2008 | Ellner et al. |
| 2008/0045384 A1 | 2/2008 | Matsubara |
| 2008/0051256 A1 | 2/2008 | Ashby et al. |
| 2008/0051258 A1 | 2/2008 | Schmehl et al. |
| 2008/0051261 A1 | 2/2008 | Lewis |
| 2008/0051919 A1 | 2/2008 | Sakai et al. |
| 2008/0051993 A1 | 2/2008 | Graham |
| 2008/0058170 A1 | 3/2008 | Giannascoli et al. |
| 2008/0059064 A1 | 3/2008 | Werner |
| 2008/0062818 A1 | 3/2008 | Plancon et al. |
| 2008/0064571 A1 | 3/2008 | Lee |
| 2008/0068559 A1 | 3/2008 | Howell et al. |
| 2008/0076969 A1 | 3/2008 | Kraft |
| 2008/0076972 A1 | 3/2008 | Dorogusker et al. |
| 2008/0077489 A1 | 3/2008 | Gilley et al. |
| 2008/0082311 A1 | 4/2008 | Meijer et al. |
| 2008/0086318 A1 | 4/2008 | Gilley et al. |
| 2008/0089551 A1 | 4/2008 | Heather et al. |
| 2008/0090703 A1 | 4/2008 | Rosenberg |
| 2008/0096726 A1 | 4/2008 | Riley et al. |
| 2008/0097633 A1 | 4/2008 | Jochelson et al. |
| 2008/0098797 A1 | 5/2008 | Considine |
| 2008/0103023 A1 | 5/2008 | Chung |
| 2008/0103024 A1 | 5/2008 | Habing |
| 2008/0103030 A1 | 5/2008 | Watson et al. |
| 2008/0108481 A1 | 5/2008 | Limma |
| 2008/0108917 A1 | 5/2008 | Joutras et al. |
| 2008/0109121 A1 | 5/2008 | Takeda |
| 2008/0109243 A1 | 5/2008 | Ebrom et al. |
| 2008/0109295 A1 | 5/2008 | McConochie et al. |
| 2008/0109310 A1 | 5/2008 | Ebrom et al. |
| 2008/0109841 A1 | 5/2008 | Heather et al. |
| 2008/0109851 A1 | 5/2008 | Heather et al. |
| 2008/0119332 A1 | 5/2008 | Roman |
| 2008/0119333 A1 | 5/2008 | Bowser |
| 2008/0119337 A1 | 5/2008 | Wilkins |
| 2008/0120436 A1 | 5/2008 | Cowgill et al. |
| 2008/0129825 A1 | 6/2008 | DeAngelis et al. |
| 2008/0132798 A1 | 6/2008 | Hong et al. |
| 2008/0139370 A1 | 6/2008 | Charnitski |
| 2008/0141135 A1 | 6/2008 | Mason et al. |
| 2008/0146334 A1 | 6/2008 | Kil |
| 2008/0146336 A1 | 6/2008 | Feldman |
| 2008/0146416 A1 | 6/2008 | Mueller et al. |
| 2008/0146890 A1 | 6/2008 | LeBoeuf et al. |
| 2008/0146892 A1 | 6/2008 | LeBoeuf et al. |
| 2008/0147502 A1 | 6/2008 | Baker |
| 2008/0153670 A1 | 6/2008 | Mckirdy |
| 2008/0153671 A1 | 6/2008 | Ogg et al. |
| 2008/0155077 A1 | 6/2008 | James |
| 2008/0161168 A1 | 7/2008 | Hsiao |
| 2008/0161653 A1 | 7/2008 | Lin et al. |
| 2008/0167535 A1 | 7/2008 | Stivoric et al. |
| 2008/0167536 A1 | 7/2008 | Teller |
| 2008/0167958 A1 | 7/2008 | Balaban et al. |
| 2008/0171636 A1 | 7/2008 | Usui et al. |
| 2008/0171945 A1 | 7/2008 | Dotter |
| 2008/0172328 A1 | 7/2008 | Ajilian |
| 2008/0176655 A1 | 7/2008 | James |
| 2008/0176713 A1 | 7/2008 | Olivera Brizzio |
| 2008/0176721 A1 | 7/2008 | Boren |
| 2008/0179214 A1 | 7/2008 | Hall |
| 2008/0182685 A1 | 7/2008 | Marty et al. |
| 2008/0182724 A1 | 7/2008 | Guthrie |
| 2008/0183049 A1 | 7/2008 | Karkanias et al. |
| 2008/0183052 A1 | 7/2008 | Teller |
| 2008/0188354 A1 | 8/2008 | Pauws et al. |
| 2008/0189733 A1 | 8/2008 | Apostolopoulos |
| 2008/0191864 A1 | 8/2008 | Wolfson |
| 2008/0195258 A1 | 8/2008 | Schendel |
| 2008/0200310 A1 | 8/2008 | Tagliabue |
| 2008/0200312 A1 | 8/2008 | Tagliabue |
| 2008/0200778 A1 | 8/2008 | Taskinen |
| 2008/0204225 A1 | 8/2008 | Kitchen |
| 2008/0207401 A1 | 8/2008 | Harding et al. |
| 2008/0207402 A1 | 8/2008 | Fisher et al. |
| 2008/0214358 A1 | 9/2008 | Ogg et al. |
| 2008/0214359 A1 | 9/2008 | Niva et al. |
| 2008/0214903 A1 | 9/2008 | Orbach |
| 2008/0218307 A1 | 9/2008 | Schoettle |
| 2008/0220941 A1 | 9/2008 | Shaw |
| 2008/0224988 A1 | 9/2008 | Whang |
| 2008/0229875 A1 | 9/2008 | Ray |
| 2008/0234023 A1 | 9/2008 | Mullahkhel et al. |
| 2008/0234113 A1 | 9/2008 | Einav |
| 2008/0242510 A1 | 10/2008 | Topel |
| 2008/0242511 A1 | 10/2008 | Munoz et al. |
| 2008/0242512 A1 | 10/2008 | Kim |
| 2008/0242513 A1 | 10/2008 | Skilken et al. |
| 2008/0249736 A1 | 10/2008 | Prstojevich |
| 2008/0253378 A1 | 10/2008 | Curry |
| 2008/0254420 A1 | 10/2008 | Nerenberg |

(56) References Cited

U.S. PATENT DOCUMENTS

| | | |
|---|---|---|
| 2008/0254947 A1 | 10/2008 | Mackay |
| 2008/0255430 A1 | 10/2008 | Alexandersson et al. |
| 2008/0261636 A1 | 10/2008 | Lau et al. |
| 2008/0261774 A1 | 10/2008 | Fisher |
| 2008/0261776 A1 | 10/2008 | Skiba |
| 2008/0262381 A1 | 10/2008 | Kolen |
| 2008/0262392 A1 | 10/2008 | Ananny et al. |
| 2008/0267444 A1 | 10/2008 | Simons-Nikolova et al. |
| 2008/0269016 A1 | 10/2008 | Ungari et al. |
| 2008/0269017 A1 | 10/2008 | Ungari |
| 2008/0273008 A1 | 11/2008 | Chang |
| 2008/0280732 A1 | 11/2008 | Jones |
| 2008/0287262 A1 | 11/2008 | Chou |
| 2008/0293023 A1 | 11/2008 | Diehl |
| 2008/0295129 A1 | 11/2008 | Laut |
| 2008/0296883 A1 | 12/2008 | Burkhardtsmaier |
| 2008/0300109 A1 | 12/2008 | Karkanias et al. |
| 2008/0300110 A1 | 12/2008 | Smith et al. |
| 2008/0300914 A1 | 12/2008 | Karkanias et al. |
| 2008/0305934 A1 | 12/2008 | Medina |
| 2008/0306762 A1 | 12/2008 | James |
| 2008/0312039 A1 | 12/2008 | Bucay-Bissu |
| 2008/0312041 A1 | 12/2008 | Schwabe et al. |
| 2008/0315371 A1 | 12/2008 | Tang et al. |
| 2008/0319787 A1 | 12/2008 | Stivoric |
| 2008/0319796 A1 | 12/2008 | Stivoric |
| 2008/0319855 A1 | 12/2008 | Stivoric |
| 2009/0005224 A1 | 1/2009 | Davis et al. |
| 2009/0011907 A1 | 1/2009 | Radow |
| 2009/0017991 A1 | 1/2009 | Hung |
| 2009/0023554 A1 | 1/2009 | Shim |
| 2009/0023556 A1 | 1/2009 | Daly |
| 2009/0024233 A1 | 1/2009 | Shirai et al. |
| 2009/0028005 A1 | 1/2009 | You et al. |
| 2009/0029831 A1 | 1/2009 | Weier |
| 2009/0040231 A1 | 2/2009 | Sano et al. |
| 2009/0040301 A1 | 2/2009 | Sandler et al. |
| 2009/0041298 A1 | 2/2009 | Sandler et al. |
| 2009/0042174 A1 | 2/2009 | Aries |
| 2009/0042696 A1 | 2/2009 | Wang |
| 2009/0043531 A1 | 2/2009 | Kahn et al. |
| 2009/0047645 A1 | 2/2009 | Dibenedetto et al. |
| 2009/0048044 A1 | 2/2009 | Oleson et al. |
| 2009/0048073 A1 | 2/2009 | Roimicher |
| 2009/0048493 A1 | 2/2009 | James et al. |
| 2009/0048939 A1 | 2/2009 | Williams |
| 2009/0049092 A1 | 2/2009 | Capio et al. |
| 2009/0054207 A1 | 2/2009 | Lin et al. |
| 2009/0061870 A1 | 3/2009 | Finkelstein et al. |
| 2009/0062598 A1 | 3/2009 | Haisma et al. |
| 2009/0069156 A1 | 3/2009 | Kurunmäki et al. |
| 2009/0069722 A1 | 3/2009 | Flaction et al. |
| 2009/0076335 A1 | 3/2009 | Schwarzberg et al. |
| 2009/0076903 A1 | 3/2009 | Schwarzberg et al. |
| 2009/0082880 A1 | 3/2009 | Saunders |
| 2009/0085873 A1 | 4/2009 | Betts et al. |
| 2009/0088248 A1 | 4/2009 | Stevens |
| 2009/0088299 A1 | 4/2009 | Chen |
| 2009/0093341 A1 | 4/2009 | James |
| 2009/0098980 A1 | 4/2009 | Waters |
| 2009/0098981 A1 | 4/2009 | Del Giorno |
| 2009/0105047 A1 | 4/2009 | Guidi et al. |
| 2009/0105052 A1 | 4/2009 | Dalebout et al. |
| 2009/0105560 A1 | 4/2009 | Solomon |
| 2009/0109346 A1 | 4/2009 | Viarani et al. |
| 2009/0111656 A1 | 4/2009 | Sullivan et al. |
| 2009/0111658 A1 | 4/2009 | Juan |
| 2009/0111670 A1 | 4/2009 | Williams |
| 2009/0117890 A1 | 5/2009 | Jacobsen et al. |
| 2009/0118099 A1 | 5/2009 | Fisher |
| 2009/0119032 A1 | 5/2009 | Meyer |
| 2009/0120208 A1 | 5/2009 | Meyer |
| 2009/0120210 A1 | 5/2009 | Phillips et al. |
| 2009/0124460 A1 | 5/2009 | Chen |
| 2009/0128342 A1 | 5/2009 | Cohen |
| 2009/0128516 A1 | 5/2009 | Rimon et al. |
| 2009/0137367 A1 | 5/2009 | Hendrickson et al. |
| 2009/0144080 A1 | 6/2009 | Gray et al. |
| 2009/0144084 A1 | 6/2009 | Neumaier |
| 2009/0144639 A1 | 6/2009 | Nims et al. |
| 2009/0149299 A1 | 6/2009 | Tchao et al. |
| 2009/0149721 A1 | 6/2009 | Yang |
| 2009/0150178 A1 | 6/2009 | Sutton et al. |
| 2009/0156364 A1 | 6/2009 | Simeoni |
| 2009/0163262 A1 | 6/2009 | Kang |
| 2009/0163323 A1 | 6/2009 | Bocchicchio |
| 2009/0171229 A1 | 7/2009 | Saldarelli |
| 2009/0174558 A1 | 7/2009 | White |
| 2009/0176526 A1 | 7/2009 | Altman |
| 2009/0176581 A1 | 7/2009 | Barnes et al. |
| 2009/0176625 A1 | 7/2009 | Giannelli et al. |
| 2009/0177068 A1 | 7/2009 | Stivoric et al. |
| 2009/0181826 A1 | 7/2009 | Turner |
| 2009/0191988 A1 | 7/2009 | Klein |
| 2009/0192391 A1 | 7/2009 | Lovitt et al. |
| 2009/0192871 A1 | 7/2009 | Deacon et al. |
| 2009/0193344 A1 | 7/2009 | Smyers |
| 2009/0195350 A1 | 8/2009 | Tsern et al. |
| 2009/0197739 A1 | 8/2009 | Hashimoto |
| 2009/0197740 A1 | 8/2009 | Julskjaer et al. |
| 2009/0204422 A1 | 8/2009 | James |
| 2009/0204668 A1 | 8/2009 | Huang |
| 2009/0205482 A1 | 8/2009 | Shirai et al. |
| 2009/0209393 A1 | 8/2009 | Crater et al. |
| 2009/0210078 A1 | 8/2009 | Crowley |
| 2009/0216629 A1 | 8/2009 | James |
| 2009/0217178 A1 | 8/2009 | Niyogi et al. |
| 2009/0221404 A1 | 9/2009 | Dorogusker et al. |
| 2009/0227429 A1 | 9/2009 | Baudhuin |
| 2009/0233769 A1 | 9/2009 | Pryor |
| 2009/0233771 A1 | 9/2009 | Quatrochi et al. |
| 2009/0238400 A1 | 9/2009 | Im |
| 2009/0239714 A1 | 9/2009 | Sellers |
| 2009/0240858 A1 | 9/2009 | Takebayashi |
| 2009/0247366 A1 | 10/2009 | Frumer |
| 2009/0253109 A1 | 10/2009 | Anvari |
| 2009/0253554 A1 | 10/2009 | Mcintosh |
| 2009/0257323 A1 | 10/2009 | Soltani |
| 2009/0258710 A1 | 10/2009 | Quatrochi et al. |
| 2009/0258758 A1 | 10/2009 | Hickman |
| 2009/0262088 A1 | 10/2009 | Moll-Carrillo et al. |
| 2009/0263772 A1 | 10/2009 | Root |
| 2009/0264260 A1 | 10/2009 | Piaget et al. |
| 2009/0265649 A1 | 10/2009 | Schlossberg et al. |
| 2009/0267783 A1 | 10/2009 | Vock et al. |
| 2009/0269728 A1 | 10/2009 | Verstegen et al. |
| 2009/0270226 A1 | 10/2009 | Watterson |
| 2009/0270743 A1 | 10/2009 | Dugan |
| 2009/0278707 A1 | 11/2009 | Biggins et al. |
| 2009/0282080 A1 | 11/2009 | Schlossberg et al. |
| 2009/0286653 A1 | 11/2009 | Wiber |
| 2009/0292178 A1 | 11/2009 | Ellis et al. |
| 2009/0298649 A1 | 12/2009 | Dyer et al. |
| 2009/0309891 A1 | 12/2009 | Karkanias et al. |
| 2009/0312151 A1 | 12/2009 | Thieberger |
| 2009/0312158 A1 | 12/2009 | Trevino et al. |
| 2009/0312658 A1 | 12/2009 | Thieberger |
| 2010/0003647 A1 | 1/2010 | Brown et al. |
| 2010/0009809 A1 | 1/2010 | Carrington |
| 2010/0009810 A1 | 1/2010 | Trzecieski |
| 2010/0016742 A1 | 1/2010 | James |
| 2010/0017402 A1 | 1/2010 | Fleming et al. |
| 2010/0019593 A1 | 1/2010 | Ritchey |
| 2010/0022354 A1 | 1/2010 | Fisher |
| 2010/0024590 A1 | 2/2010 | O'neill |
| 2010/0031803 A1 | 2/2010 | Lozada et al. |
| 2010/0035726 A1 | 2/2010 | Fisher et al. |
| 2010/0036736 A1 | 2/2010 | McGee et al. |
| 2010/0038149 A1 | 2/2010 | Corel |
| 2010/0041000 A1 | 2/2010 | Glass |
| 2010/0048358 A1 | 2/2010 | Tchao et al. |
| 2010/0050082 A1 | 2/2010 | Katz et al. |
| 2010/0056339 A1 | 3/2010 | Chen |
| 2010/0056340 A1 | 3/2010 | Ellis |

(56) References Cited

U.S. PATENT DOCUMENTS

| | | |
|---|---|---|
| 2010/0056876 A1 | 3/2010 | Ellis |
| 2010/0062818 A1 | 3/2010 | Haughay, Jr. et al. |
| 2010/0064255 A1 | 3/2010 | Rottler et al. |
| 2010/0068684 A1 | 3/2010 | Sabel |
| 2010/0075812 A1 | 3/2010 | Piaget et al. |
| 2010/0076278 A1 | 3/2010 | van der Zande et al. |
| 2010/0077564 A1 | 4/2010 | Saier et al. |
| 2010/0079291 A1 | 4/2010 | Kroll et al. |
| 2010/0081116 A1 | 4/2010 | Barasch et al. |
| 2010/0081548 A1 | 4/2010 | Labedz |
| 2010/0087701 A1 | 4/2010 | Berka et al. |
| 2010/0088023 A1 | 4/2010 | Werner |
| 2010/0093492 A1 | 4/2010 | Watterson et al. |
| 2010/0093493 A1 | 4/2010 | Eldridge |
| 2010/0099437 A1 | 4/2010 | Moerdijk |
| 2010/0099954 A1 | 4/2010 | Dickinson et al. |
| 2010/0112536 A1 | 5/2010 | Claassen et al. |
| 2010/0113222 A1 | 5/2010 | Radow |
| 2010/0113223 A1 | 5/2010 | Chiles et al. |
| 2010/0113948 A1 | 5/2010 | Yang et al. |
| 2010/0120585 A1 | 5/2010 | Quy |
| 2010/0125026 A1 | 5/2010 | Zavadsky et al. |
| 2010/0125029 A1 | 5/2010 | Nielson et al. |
| 2010/0125183 A1 | 5/2010 | Vayalattu et al. |
| 2010/0137049 A1 | 6/2010 | Epstein |
| 2010/0137106 A1 | 6/2010 | Oshima et al. |
| 2010/0146055 A1 | 6/2010 | Hannuksela |
| 2010/0152546 A1 | 6/2010 | Behan et al. |
| 2010/0156625 A1 | 6/2010 | Ruha |
| 2010/0156760 A1 | 6/2010 | Cheswick |
| 2010/0160013 A1 | 6/2010 | Sanders |
| 2010/0160014 A1 | 6/2010 | Galasso et al. |
| 2010/0160115 A1 | 6/2010 | Morris et al. |
| 2010/0167801 A1 | 7/2010 | Karkanias et al. |
| 2010/0167876 A1 | 7/2010 | Cheng |
| 2010/0173276 A1 | 7/2010 | Vasin |
| 2010/0179035 A1 | 7/2010 | Carnahan |
| 2010/0179883 A1 | 7/2010 | Devolites |
| 2010/0182436 A1 | 7/2010 | Boman et al. |
| 2010/0184565 A1 | 7/2010 | Avellino |
| 2010/0188405 A1 | 7/2010 | Haughay, Jr. et al. |
| 2010/0190610 A1 | 7/2010 | Pryor |
| 2010/0190615 A1 | 7/2010 | Baker et al. |
| 2010/0191462 A1 | 7/2010 | Kobuya et al. |
| 2010/0197462 A1 | 8/2010 | Piane, Jr. |
| 2010/0204013 A1 | 8/2010 | Chen |
| 2010/0208038 A1 | 8/2010 | Kutliroff et al. |
| 2010/0208082 A1 | 8/2010 | Buchner et al. |
| 2010/0211439 A1 | 8/2010 | Marci et al. |
| 2010/0216536 A1 | 8/2010 | Gagner |
| 2010/0216600 A1 | 8/2010 | Noffsinger |
| 2010/0216603 A1 | 8/2010 | Somers |
| 2010/0217096 A1 | 8/2010 | Nanikashvili |
| 2010/0217099 A1 | 8/2010 | Leboeuf |
| 2010/0217102 A1 | 8/2010 | LeBoeuf et al. |
| 2010/0222165 A1 | 9/2010 | Nurnberg et al. |
| 2010/0222178 A1 | 9/2010 | Shea |
| 2010/0222179 A1 | 9/2010 | Temple et al. |
| 2010/0227542 A1 | 9/2010 | Goldmann |
| 2010/0234184 A1 | 9/2010 | Le Page |
| 2010/0234185 A1 | 9/2010 | Watt et al. |
| 2010/0234693 A1 | 9/2010 | Srinivasan et al. |
| 2010/0240458 A1 | 9/2010 | Gaiba et al. |
| 2010/0240495 A1 | 9/2010 | Law |
| 2010/0240945 A1 | 9/2010 | Bikko |
| 2010/0241018 A1 | 9/2010 | Vogel |
| 2010/0243514 A1 | 9/2010 | Samain et al. |
| 2010/0247081 A1 | 9/2010 | Victoria Pons |
| 2010/0248900 A1 | 9/2010 | Ashby |
| 2010/0248901 A1 | 9/2010 | Martens |
| 2010/0251454 A1 | 10/2010 | Kiernan |
| 2010/0255884 A1 | 10/2010 | Konkka et al. |
| 2010/0255955 A1 | 10/2010 | Hickman |
| 2010/0255965 A1 | 10/2010 | Chen |
| 2010/0259043 A1 | 10/2010 | Balsamo |
| 2010/0261580 A1 | 10/2010 | Lannon |
| 2010/0271367 A1 | 10/2010 | Vaden et al. |
| 2010/0273610 A1 | 10/2010 | Johnson |
| 2010/0274100 A1 | 10/2010 | Behar |
| 2010/0279822 A1 | 11/2010 | Ford |
| 2010/0279823 A1 | 11/2010 | Waters |
| 2010/0281463 A1 | 11/2010 | Estrade |
| 2010/0283601 A1 | 11/2010 | Tai et al. |
| 2010/0289772 A1 | 11/2010 | Miller |
| 2010/0292050 A1 | 11/2010 | DiBenedetto et al. |
| 2010/0292599 A1 | 11/2010 | Oleson et al. |
| 2010/0292600 A1 | 11/2010 | Dibenedetto et al. |
| 2010/0298098 A1 | 11/2010 | Ercan |
| 2010/0298655 A1 | 11/2010 | McCombie et al. |
| 2010/0298656 A1 | 11/2010 | McCombie et al. |
| 2010/0298661 A1 | 11/2010 | Mccombie et al. |
| 2010/0300272 A1 | 12/2010 | Scherf |
| 2010/0302142 A1 | 12/2010 | French |
| 2010/0302250 A1 | 12/2010 | Hoebel |
| 2010/0304932 A1 | 12/2010 | Kolman et al. |
| 2010/0312596 A1 | 12/2010 | Saffari et al. |
| 2010/0324387 A1 | 12/2010 | Moon |
| 2010/0327603 A1 | 12/2010 | Suaan |
| 2011/0003663 A1 | 1/2011 | Chiu et al. |
| 2011/0003664 A1 | 1/2011 | Richard |
| 2011/0009240 A1 | 1/2011 | Chiu et al. |
| 2011/0009249 A1 | 1/2011 | Campanaro et al. |
| 2011/0014351 A1 | 1/2011 | Reider et al. |
| 2011/0015039 A1 | 1/2011 | Shea |
| 2011/0015041 A1 | 1/2011 | Shea |
| 2011/0015468 A1 | 1/2011 | Aarts et al. |
| 2011/0021319 A1 | 1/2011 | Nissila et al. |
| 2011/0021953 A1 | 1/2011 | Sanematsu et al. |
| 2011/0028277 A1 | 2/2011 | Merli |
| 2011/0032105 A1 | 2/2011 | Hoffman et al. |
| 2011/0034300 A1 | 2/2011 | Hall |
| 2011/0039659 A1 | 2/2011 | Kim et al. |
| 2011/0046519 A1 | 2/2011 | Raheman |
| 2011/0053131 A1 | 3/2011 | Regnier |
| 2011/0054242 A1 | 3/2011 | Bender |
| 2011/0054270 A1 | 3/2011 | Derchak |
| 2011/0054272 A1 | 3/2011 | Derchak |
| 2011/0054359 A1 | 3/2011 | Sazonov et al. |
| 2011/0054809 A1 | 3/2011 | Templeman |
| 2011/0061515 A1 | 3/2011 | Turner |
| 2011/0063114 A1 | 3/2011 | Ikoyan |
| 2011/0066056 A1 | 3/2011 | Huang |
| 2011/0072955 A1 | 3/2011 | Turner |
| 2011/0082006 A1 | 4/2011 | Ishii |
| 2011/0082007 A1 | 4/2011 | Birrell |
| 2011/0082010 A1 | 4/2011 | Dyer |
| 2011/0082011 A1 | 4/2011 | Ellis |
| 2011/0082015 A1 | 4/2011 | Dreissigacker et al. |
| 2011/0082397 A1 | 4/2011 | Alberts |
| 2011/0086707 A1 | 4/2011 | Loveland |
| 2011/0087076 A1 | 4/2011 | Brynelsen et al. |
| 2011/0087137 A1 | 4/2011 | Hanoun |
| 2011/0087446 A1 | 4/2011 | Redmond |
| 2011/0090092 A1 | 4/2011 | Birrell et al. |
| 2011/0091842 A1 | 4/2011 | Dugan |
| 2011/0092779 A1 | 4/2011 | Chang et al. |
| 2011/0096764 A1 | 4/2011 | Tunioli et al. |
| 2011/0098615 A1 | 4/2011 | Whalen et al. |
| 2011/0105278 A1 | 5/2011 | Fabbri |
| 2011/0105279 A1 | 5/2011 | Herranen |
| 2011/0105920 A1 | 5/2011 | Haataja |
| 2011/0106597 A1 | 5/2011 | Ferdman et al. |
| 2011/0117529 A1 | 5/2011 | Barash |
| 2011/0118084 A1 | 5/2011 | Tsai et al. |
| 2011/0118086 A1 | 5/2011 | Radow |
| 2011/0118089 A1 | 5/2011 | Ellis |
| 2011/0124469 A1 | 5/2011 | Uhlir |
| 2011/0124978 A1 | 5/2011 | Williams |
| 2011/0125063 A1 | 5/2011 | Shalon et al. |
| 2011/0131005 A1 | 6/2011 | Ueshima et al. |
| 2011/0136627 A1 | 6/2011 | Williams |
| 2011/0140904 A1 | 6/2011 | Kashi |
| 2011/0143769 A1 | 6/2011 | Jones et al. |
| 2011/0152032 A1 | 6/2011 | Barnett |

(56) References Cited

U.S. PATENT DOCUMENTS

| | | |
|---|---|---|
| 2011/0152033 A1 | 6/2011 | Yang |
| 2011/0152696 A1 | 6/2011 | Ryan |
| 2011/0163939 A1 | 7/2011 | Tam et al. |
| 2011/0164044 A1 | 7/2011 | Huang |
| 2011/0164175 A1 | 7/2011 | Chung et al. |
| 2011/0165995 A1 | 7/2011 | Paulus |
| 2011/0165996 A1 | 7/2011 | Paulus |
| 2011/0165997 A1 | 7/2011 | Reich |
| 2011/0165998 A1 | 7/2011 | Dreissigacker et al. |
| 2011/0167447 A1 | 7/2011 | Wong |
| 2011/0172058 A1 | 7/2011 | Deaconu |
| 2011/0172059 A1 | 7/2011 | Watterson et al. |
| 2011/0172060 A1 | 7/2011 | Morales et al. |
| 2011/0175744 A1 | 7/2011 | Englert et al. |
| 2011/0175989 A1 | 7/2011 | Islam |
| 2011/0176943 A1 | 7/2011 | Tran et al. |
| 2011/0177919 A1 | 7/2011 | Tamari |
| 2011/0179068 A1 | 7/2011 | O'brien |
| 2011/0181420 A1 | 7/2011 | Mack et al. |
| 2011/0183307 A1 | 7/2011 | Shum et al. |
| 2011/0184225 A1 | 7/2011 | Whitall et al. |
| 2011/0184247 A1 | 7/2011 | Contant et al. |
| 2011/0188668 A1 | 8/2011 | Donaldson |
| 2011/0191123 A1 | 8/2011 | Buzynski |
| 2011/0195819 A1 | 8/2011 | Shaw |
| 2011/0197157 A1 | 8/2011 | Hoffman et al. |
| 2011/0199393 A1 | 8/2011 | Nurse et al. |
| 2011/0201476 A1 | 8/2011 | Solomon |
| 2011/0202236 A1 | 8/2011 | Galasso et al. |
| 2011/0214148 A1 | 9/2011 | Gossweiler, III et al. |
| 2011/0218086 A1 | 9/2011 | Boren |
| 2011/0221672 A1 | 9/2011 | Osterhout et al. |
| 2011/0222375 A1 | 9/2011 | Tsubata et al. |
| 2011/0224057 A1 | 9/2011 | Wu |
| 2011/0224498 A1 | 9/2011 | Banet et al. |
| 2011/0229862 A1 | 9/2011 | Parikh |
| 2011/0230732 A1 | 9/2011 | Edman et al. |
| 2011/0238217 A1 | 9/2011 | Kume |
| 2011/0245633 A1 | 10/2011 | Goldberg et al. |
| 2011/0251021 A1 | 10/2011 | Zavadsky et al. |
| 2011/0263385 A1 | 10/2011 | Shea |
| 2011/0264305 A1 | 10/2011 | Choe |
| 2011/0267196 A1 | 11/2011 | Hu et al. |
| 2011/0270135 A1 | 11/2011 | Dooley |
| 2011/0275482 A1 | 11/2011 | Brodess et al. |
| 2011/0275489 A1 | 11/2011 | Apau |
| 2011/0276312 A1 | 11/2011 | Shalon et al. |
| 2011/0281249 A1 | 11/2011 | Gammell et al. |
| 2011/0283188 A1 | 11/2011 | Farrenkopf et al. |
| 2011/0283231 A1 | 11/2011 | Richstein et al. |
| 2011/0295083 A1 | 12/2011 | Doelling et al. |
| 2011/0311955 A1 | 12/2011 | Forsten et al. |
| 2011/0319229 A1 | 12/2011 | Corbalis et al. |
| 2011/0320380 A1 | 12/2011 | Zahn et al. |
| 2012/0004074 A1 | 1/2012 | Schelzig |
| 2012/0004076 A1 | 1/2012 | Fenster |
| 2012/0015778 A1 | 1/2012 | Lee et al. |
| 2012/0015779 A1 | 1/2012 | Powch et al. |
| 2012/0015784 A1 | 1/2012 | Reed |
| 2012/0021873 A1 | 1/2012 | Brunner |
| 2012/0024237 A1 | 2/2012 | Rice |
| 2012/0028761 A1 | 2/2012 | Dorogusker et al. |
| 2012/0035487 A1 | 2/2012 | Werner et al. |
| 2012/0036557 A1 | 2/2012 | Li |
| 2012/0050818 A1 | 3/2012 | Watanabe |
| 2012/0055718 A1 | 3/2012 | Chen |
| 2012/0065031 A1 | 3/2012 | Buzzanco |
| 2012/0071301 A1 | 3/2012 | Kaylor et al. |
| 2012/0078127 A1 | 3/2012 | McDonald et al. |
| 2012/0079429 A1 | 3/2012 | Stathacopoulos et al. |
| 2012/0079529 A1 | 3/2012 | Harris et al. |
| 2012/0081531 A1 | 4/2012 | DeAngelis et al. |
| 2012/0083669 A1 | 4/2012 | Abujbara |
| 2012/0083705 A1 | 4/2012 | Yuen et al. |
| 2012/0084807 A1 | 4/2012 | Thompson et al. |
| 2012/0084811 A1 | 4/2012 | Thompson |
| 2012/0084812 A1 | 4/2012 | Thompson et al. |
| 2012/0088634 A1 | 4/2012 | Heidecke |
| 2012/0090446 A1 | 4/2012 | Moreno |
| 2012/0092327 A1 | 4/2012 | Adhikari |
| 2012/0096357 A1 | 4/2012 | Folgner et al. |
| 2012/0096405 A1 | 4/2012 | Seo |
| 2012/0105867 A1 | 5/2012 | Komatsu |
| 2012/0108914 A1 | 5/2012 | Bravomalo |
| 2012/0113029 A1 | 5/2012 | Ye et al. |
| 2012/0115695 A1 | 5/2012 | Watterson et al. |
| 2012/0116550 A1 | 5/2012 | Hoffman et al. |
| 2012/0116684 A1 | 5/2012 | Ingrassia et al. |
| 2012/0116806 A1 | 5/2012 | Stark et al. |
| 2012/0122063 A1 | 5/2012 | Chen et al. |
| 2012/0125559 A1 | 5/2012 | Fadell et al. |
| 2012/0129139 A1 | 5/2012 | Partovi |
| 2012/0143358 A1 | 6/2012 | Adams et al. |
| 2012/0149996 A1 | 6/2012 | Stivoric et al. |
| 2012/0153015 A1 | 6/2012 | Gomez et al. |
| 2012/0157265 A1 | 6/2012 | Kao |
| 2012/0159563 A1 | 6/2012 | Gomez et al. |
| 2012/0165703 A1 | 6/2012 | Bottum |
| 2012/0174608 A1 | 7/2012 | Kumamoto et al. |
| 2012/0179278 A1 | 7/2012 | Riley et al. |
| 2012/0190504 A1 | 7/2012 | Lee et al. |
| 2012/0202656 A1 | 8/2012 | Dorsay |
| 2012/0208153 A1 | 8/2012 | Bolla et al. |
| 2012/0214590 A1 | 8/2012 | Newhouse et al. |
| 2012/0217758 A1 | 8/2012 | Chen |
| 2012/0218184 A1 | 8/2012 | Wissmar |
| 2012/0225412 A1 | 9/2012 | Wagner |
| 2012/0228385 A1 | 9/2012 | Deluca |
| 2012/0233002 A1 | 9/2012 | Abujbara |
| 2012/0237906 A9 | 9/2012 | Glass |
| 2012/0237911 A1 | 9/2012 | Watterson |
| 2012/0238800 A1 | 9/2012 | Naujokat et al. |
| 2012/0238851 A1 | 9/2012 | Kamen et al. |
| 2012/0251983 A1 | 10/2012 | Golden |
| 2012/0252580 A1 | 10/2012 | Dugan |
| 2012/0253234 A1 | 10/2012 | Yang et al. |
| 2012/0253487 A1 | 10/2012 | Dugan |
| 2012/0253489 A1 | 10/2012 | Dugan |
| 2012/0258433 A1 | 10/2012 | Hope et al. |
| 2012/0268592 A1 | 10/2012 | Aragones et al. |
| 2012/0271121 A1 | 10/2012 | Della Torre et al. |
| 2012/0277040 A1 | 11/2012 | Vincent et al. |
| 2012/0285986 A1 | 11/2012 | Irvin |
| 2012/0290109 A1 | 11/2012 | Engelberg et al. |
| 2012/0295764 A1 | 11/2012 | Brammer |
| 2012/0306643 A1 | 12/2012 | Dugan |
| 2012/0313776 A1 | 12/2012 | Utter, II |
| 2012/0315986 A1 | 12/2012 | Walling |
| 2012/0315987 A1 | 12/2012 | Walling |
| 2012/0316406 A1 | 12/2012 | Rahman et al. |
| 2012/0316455 A1 | 12/2012 | Rahman et al. |
| 2012/0316456 A1 | 12/2012 | Rahman et al. |
| 2012/0316458 A1 | 12/2012 | Rahman et al. |
| 2012/0317024 A1 | 12/2012 | Rahman et al. |
| 2012/0322628 A1 | 12/2012 | Gautier |
| 2012/0323496 A1 | 12/2012 | Burroughs |
| 2012/0329027 A1 | 12/2012 | Lewolt |
| 2012/0329611 A1 | 12/2012 | Bouchard |
| 2013/0002533 A1 | 1/2013 | Burroughs et al. |
| 2013/0011818 A1 | 1/2013 | Shum et al. |
| 2013/0014155 A1 | 1/2013 | Clarke et al. |
| 2013/0015945 A1 | 1/2013 | Chang |
| 2013/0017888 A1 | 1/2013 | King et al. |
| 2013/0018668 A1 | 1/2013 | Goldberg et al. |
| 2013/0029807 A1 | 1/2013 | Amsel |
| 2013/0035209 A1 | 2/2013 | Gilley et al. |
| 2013/0035612 A1 | 2/2013 | Mason et al. |
| 2013/0040271 A1 | 2/2013 | Rytky et al. |
| 2013/0040783 A1 | 2/2013 | Duda et al. |
| 2013/0041590 A1 | 2/2013 | Burich et al. |
| 2013/0041617 A1 | 2/2013 | Pease et al. |
| 2013/0053218 A1 | 2/2013 | Barker |
| 2013/0053717 A1 | 2/2013 | Vandine et al. |
| 2013/0053990 A1 | 2/2013 | Ackland |

(56) References Cited

U.S. PATENT DOCUMENTS

| | | |
|---|---|---|
| 2013/0065680 A1 | 3/2013 | Zavadsky |
| 2013/0073093 A1 | 3/2013 | Songkakul |
| 2013/0083003 A1 | 4/2013 | Perez et al. |
| 2013/0085038 A1 | 4/2013 | Fischer |
| 2013/0090565 A1 | 4/2013 | Quy |
| 2013/0097635 A1 | 4/2013 | Yerli |
| 2013/0105565 A1 | 5/2013 | Kamprath |
| 2013/0106684 A1 | 5/2013 | Weast et al. |
| 2013/0108995 A1 | 5/2013 | DePasqua et al. |
| 2013/0116091 A1 | 5/2013 | Fritz |
| 2013/0116092 A1 | 5/2013 | Martinez et al. |
| 2013/0116514 A1 | 5/2013 | Kroner et al. |
| 2013/0127636 A1 | 5/2013 | Aryanpur et al. |
| 2013/0129217 A1 | 5/2013 | Gupta |
| 2013/0135115 A1 | 5/2013 | Johnson et al. |
| 2013/0137552 A1 | 5/2013 | Kemp et al. |
| 2013/0144464 A1 | 6/2013 | Dorogusker et al. |
| 2013/0148861 A1 | 6/2013 | Ferlatte et al. |
| 2013/0154441 A1 | 6/2013 | Redmond |
| 2013/0158368 A1 | 6/2013 | Pacione et al. |
| 2013/0165195 A1 | 6/2013 | Watterson |
| 2013/0172152 A1 | 7/2013 | Watterson |
| 2013/0173156 A1 | 7/2013 | Wither et al. |
| 2013/0174273 A1 | 7/2013 | Grab et al. |
| 2013/0177884 A1 | 7/2013 | Root |
| 2013/0178334 A1 | 7/2013 | Brammer |
| 2013/0184843 A1 | 7/2013 | Ellis et al. |
| 2013/0190136 A1 | 7/2013 | Watterson |
| 2013/0191034 A1 | 7/2013 | Weast et al. |
| 2013/0196821 A1 | 8/2013 | Watterson et al. |
| 2013/0196822 A1 | 8/2013 | Watterson et al. |
| 2013/0203557 A1 | 8/2013 | Su |
| 2013/0208576 A1 | 8/2013 | Loree, IV et al. |
| 2013/0209972 A1 | 8/2013 | Carter et al. |
| 2013/0210578 A1 | 8/2013 | Birrell |
| 2013/0210581 A1 | 8/2013 | Watterson et al. |
| 2013/0210582 A1 | 8/2013 | Del Toro et al. |
| 2013/0216982 A1 | 8/2013 | Bennett et al. |
| 2013/0216990 A1 | 8/2013 | Chu et al. |
| 2013/0228063 A1 | 9/2013 | Turner |
| 2013/0231226 A1 | 9/2013 | Bonutti |
| 2013/0231575 A1 | 9/2013 | Erkkila et al. |
| 2013/0233097 A1 | 9/2013 | Hayner |
| 2013/0241696 A1 | 9/2013 | Fabrizio |
| 2013/0245966 A1 | 9/2013 | Burroughs et al. |
| 2013/0253943 A1 | 9/2013 | Lee et al. |
| 2013/0260965 A1 | 10/2013 | Chia et al. |
| 2013/0267385 A1 | 10/2013 | Watterson et al. |
| 2013/0273509 A1 | 10/2013 | Mutti |
| 2013/0274040 A1 | 10/2013 | Coza et al. |
| 2013/0274067 A1 | 10/2013 | Watterson et al. |
| 2013/0274069 A1 | 10/2013 | Watterson et al. |
| 2013/0274587 A1 | 10/2013 | Coza et al. |
| 2013/0274635 A1 | 10/2013 | Coza et al. |
| 2013/0274904 A1 | 10/2013 | Coza et al. |
| 2013/0282157 A1 | 10/2013 | Shin et al. |
| 2013/0282447 A1 | 10/2013 | Himanen et al. |
| 2013/0288223 A1 | 10/2013 | Watterson et al. |
| 2013/0289932 A1 | 10/2013 | Baechler |
| 2013/0290364 A1 | 10/2013 | Minvielle |
| 2013/0297642 A1 | 11/2013 | Minvielle |
| 2013/0298019 A1 | 11/2013 | Henderson |
| 2013/0303837 A1 | 11/2013 | Berka et al. |
| 2013/0310221 A1 | 11/2013 | Zuber |
| 2013/0310230 A1 | 11/2013 | Norris |
| 2013/0310658 A1 | 11/2013 | Ricks |
| 2013/0316830 A1 | 11/2013 | Sedzin et al. |
| 2013/0328416 A1 | 12/2013 | Whitworth et al. |
| 2013/0337974 A1 | 12/2013 | Yanev et al. |
| 2013/0345978 A1 | 12/2013 | Lush et al. |
| 2014/0011645 A1 | 1/2014 | Johnson et al. |
| 2014/0031174 A1 | 1/2014 | Huang |
| 2014/0031703 A1 | 1/2014 | Rayner et al. |
| 2014/0038781 A1 | 2/2014 | Foley |
| 2014/0039329 A1 | 2/2014 | Kampman et al. |
| 2014/0045656 A1 | 2/2014 | Zhang |
| 2014/0058806 A1 | 2/2014 | Guenette et al. |
| 2014/0066264 A1 | 3/2014 | Haddon |
| 2014/0069838 A1 | 3/2014 | Minvielle |
| 2014/0074265 A1 | 3/2014 | Arginsky |
| 2014/0077494 A1 | 3/2014 | Sutkowski |
| 2014/0080102 A1 | 3/2014 | Krishna |
| 2014/0081436 A1 | 3/2014 | Cowley |
| 2014/0085077 A1 | 3/2014 | Luna et al. |
| 2014/0087923 A1 | 3/2014 | Warren |
| 2014/0089836 A1 | 3/2014 | Damani et al. |
| 2014/0094941 A1 | 4/2014 | Ellis et al. |
| 2014/0099614 A1 | 4/2014 | Hu et al. |
| 2014/0100464 A1 | 4/2014 | Kaleal et al. |
| 2014/0106322 A1 | 4/2014 | Durand |
| 2014/0113779 A1 | 4/2014 | Loach |
| 2014/0121471 A1 | 5/2014 | Walker |
| 2014/0125618 A1 | 5/2014 | Panther et al. |
| 2014/0129240 A1 | 5/2014 | Zhang |
| 2014/0134582 A1 | 5/2014 | Konishi |
| 2014/0135173 A1 | 5/2014 | Watterson |
| 2014/0135631 A1 | 5/2014 | Brumback et al. |
| 2014/0139450 A1 | 5/2014 | Levesque et al. |
| 2014/0141396 A1 | 5/2014 | Spratt |
| 2014/0142403 A1 | 5/2014 | Brumback et al. |
| 2014/0145935 A1 | 5/2014 | Sztuk |
| 2014/0147829 A1 | 5/2014 | Jerauld |
| 2014/0150042 A1 | 5/2014 | Pacor et al. |
| 2014/0156041 A1 | 6/2014 | Martin |
| 2014/0156084 A1 | 6/2014 | Rahman et al. |
| 2014/0156308 A1 | 6/2014 | Ohnemus et al. |
| 2014/0156645 A1 | 6/2014 | Brust et al. |
| 2014/0162230 A1 | 6/2014 | Akopian |
| 2014/0163429 A1 | 6/2014 | Tropper et al. |
| 2014/0164611 A1 | 6/2014 | Molettiere et al. |
| 2014/0171272 A1 | 6/2014 | Hawkins, III et al. |
| 2014/0172873 A1 | 6/2014 | Varoglu et al. |
| 2014/0173660 A1 | 6/2014 | Correa et al. |
| 2014/0180480 A1 | 6/2014 | Lee et al. |
| 2014/0194260 A1 | 7/2014 | Campanaro et al. |
| 2014/0195103 A1 | 7/2014 | Nassef |
| 2014/0197946 A1 | 7/2014 | Park et al. |
| 2014/0200691 A1 | 7/2014 | Lee et al. |
| 2014/0203943 A1 | 7/2014 | Kates |
| 2014/0205980 A1 | 7/2014 | Braier et al. |
| 2014/0206506 A1 | 7/2014 | Huang |
| 2014/0212857 A1 | 7/2014 | Sullivan et al. |
| 2014/0213416 A1 | 7/2014 | Wang |
| 2014/0214446 A1 | 7/2014 | Pera, Jr. |
| 2014/0220514 A1 | 8/2014 | Waldron et al. |
| 2014/0221168 A1 | 8/2014 | Chen |
| 2014/0221784 A1 | 8/2014 | Pacione et al. |
| 2014/0221854 A1 | 8/2014 | Wai |
| 2014/0228118 A1 | 8/2014 | Hardy et al. |
| 2014/0228649 A1 | 8/2014 | Rayner et al. |
| 2014/0235409 A1 | 8/2014 | Salmon |
| 2014/0235411 A1 | 8/2014 | Dailey |
| 2014/0249440 A1 | 9/2014 | Banet |
| 2014/0257535 A1 | 9/2014 | Morris et al. |
| 2014/0257537 A1 | 9/2014 | Stroupe et al. |
| 2014/0265072 A1 | 9/2014 | Chiu |
| 2014/0266939 A1 | 9/2014 | Baringer et al. |
| 2014/0270375 A1 | 9/2014 | Canavan et al. |
| 2014/0272894 A1 | 9/2014 | Grimes et al. |
| 2014/0273858 A1 | 9/2014 | Panther et al. |
| 2014/0274564 A1 | 9/2014 | Greenbaum |
| 2014/0274574 A1 | 9/2014 | Shorten et al. |
| 2014/0275852 A1 | 9/2014 | Hong et al. |
| 2014/0275854 A1 | 9/2014 | Venkatraman et al. |
| 2014/0277637 A1 | 9/2014 | Ventura et al. |
| 2014/0278139 A1 | 9/2014 | Hong et al. |
| 2014/0278218 A1 | 9/2014 | Chang |
| 2014/0278220 A1 | 9/2014 | Yuen |
| 2014/0288390 A1 | 9/2014 | Hong et al. |
| 2014/0288438 A1 | 9/2014 | Venkatraman et al. |
| 2014/0288680 A1 | 9/2014 | Hoffman et al. |
| 2014/0308629 A1 | 10/2014 | Dugan |
| 2014/0309085 A1 | 10/2014 | Watterson et al. |
| 2014/0316192 A1 | 10/2014 | de Zambotti et al. |

(56) References Cited

U.S. PATENT DOCUMENTS

| | | |
|---|---|---|
| 2014/0335490 A1 | 11/2014 | Baarman et al. |
| 2014/0336796 A1 | 11/2014 | Agnew |
| 2014/0349257 A1 | 11/2014 | Connor |
| 2014/0351150 A1 | 11/2014 | Ainsworth et al. |
| 2014/0358012 A1 | 12/2014 | Richards et al. |
| 2014/0363797 A1 | 12/2014 | Hu et al. |
| 2014/0363800 A1 | 12/2014 | Harris et al. |
| 2014/0371887 A1 | 12/2014 | Hoffman et al. |
| 2014/0380167 A1 | 12/2014 | Bloch et al. |
| 2015/0004579 A1 | 1/2015 | Shelton |
| 2015/0004580 A1 | 1/2015 | Shum et al. |
| 2015/0011362 A1 | 1/2015 | Oh et al. |
| 2015/0018989 A1 | 1/2015 | Chen |
| 2015/0019135 A1 | 1/2015 | Kacyvenski et al. |
| 2015/0025660 A1 | 1/2015 | Prassler et al. |
| 2015/0031964 A1 | 1/2015 | Bly et al. |
| 2015/0079562 A1 | 3/2015 | Yeh et al. |
| 2015/0081209 A1 | 3/2015 | Yeh et al. |
| 2015/0081210 A1 | 3/2015 | Yeh et al. |
| 2015/0082408 A1 | 3/2015 | Yeh et al. |
| 2015/0087478 A1 | 3/2015 | Zhang et al. |
| 2015/0092972 A1 | 4/2015 | Lai et al. |
| 2015/0097700 A1 | 4/2015 | Holthouse |
| 2015/0099952 A1 | 4/2015 | Lain et al. |
| 2015/0105220 A1 | 4/2015 | Hong |
| 2015/0105881 A1 | 4/2015 | Guerrero et al. |
| 2015/0106868 A1 | 4/2015 | Lo |
| 2015/0118657 A1 | 4/2015 | Shrake et al. |
| 2015/0119197 A1 | 4/2015 | Liu |
| 2015/0126873 A1 | 5/2015 | Connor |
| 2015/0135284 A1 | 5/2015 | Bogard |
| 2015/0141202 A1 | 5/2015 | Ellis et al. |
| 2015/0151160 A1 | 6/2015 | Balakrishnan et al. |
| 2015/0154452 A1 | 6/2015 | Bentley et al. |
| 2015/0157918 A1 | 6/2015 | Tracy |
| 2015/0165269 A1 | 6/2015 | Herrala et al. |
| 2015/0168365 A1 | 6/2015 | Connor |
| 2015/0181314 A1 | 6/2015 | Swanson |
| 2015/0186609 A1 | 7/2015 | Utter, II |
| 2015/0190679 A1 | 7/2015 | Carbone |
| 2015/0199494 A1 | 7/2015 | Koduri et al. |
| 2015/0209617 A1 | 7/2015 | Hsiao |
| 2015/0224363 A1 | 8/2015 | Clark et al. |
| 2015/0238815 A1 | 8/2015 | Lee |
| 2015/0248844 A1 | 9/2015 | Ellis et al. |
| 2015/0250420 A1 | 9/2015 | Longinotti-Buitoni et al. |
| 2015/0251055 A1 | 9/2015 | Ashby |
| 2015/0253210 A1 | 9/2015 | Ashby et al. |
| 2015/0255002 A1 | 9/2015 | Harris et al. |
| 2015/0258382 A1 | 9/2015 | Nolan et al. |
| 2015/0258384 A1 | 9/2015 | Suzuki |
| 2015/0262459 A1 | 9/2015 | Munro et al. |
| 2015/0265903 A1 | 9/2015 | Kolen et al. |
| 2015/0269354 A1 | 9/2015 | Klassen |
| 2015/0272262 A1 | 10/2015 | Escamilla |
| 2015/0272473 A1 | 10/2015 | Zafiroglu |
| 2015/0273272 A1 | 10/2015 | Wang |
| 2015/0288926 A1 | 10/2015 | Glass et al. |
| 2015/0290490 A1 | 10/2015 | Badarneh |
| 2015/0296020 A1 | 10/2015 | Granqvist et al. |
| 2015/0305961 A1 | 10/2015 | Broerman et al. |
| 2015/0306456 A1 | 10/2015 | Pasini et al. |
| 2015/0310062 A1 | 10/2015 | Wang et al. |
| 2015/0318015 A1 | 11/2015 | Bose et al. |
| 2015/0320588 A1 | 11/2015 | Connor |
| 2015/0324751 A1 | 11/2015 | Orenstein et al. |
| 2015/0327804 A1 | 11/2015 | Lefever et al. |
| 2015/0331449 A1 | 11/2015 | Ng |
| 2015/0335288 A1 | 11/2015 | Toth et al. |
| 2015/0339946 A1 | 11/2015 | Pacione et al. |
| 2015/0342815 A1 | 12/2015 | Watson |
| 2015/0346994 A1 | 12/2015 | Chanyontpatanakul |
| 2015/0351690 A1 | 12/2015 | Toth et al. |
| 2015/0352404 A1 | 12/2015 | Schwenger |
| 2015/0360133 A1 | 12/2015 | Maccallum et al. |
| 2015/0364026 A1 | 12/2015 | Rubin et al. |
| 2015/0364058 A1 | 12/2015 | Lagree |
| 2015/0366746 A1 | 12/2015 | Ashby |
| 2015/0367158 A1 | 12/2015 | Pretz et al. |
| 2015/0369326 A1 | 12/2015 | Modrezejewski et al. |
| 2015/0370320 A1 | 12/2015 | Connor |
| 2015/0379239 A1 | 12/2015 | Basta et al. |
| 2015/0379891 A1 | 12/2015 | Wallace |
| 2015/0381736 A1 | 12/2015 | Seltzer |
| 2016/0012749 A1 | 1/2016 | Connor |
| 2016/0018119 A1 | 1/2016 | Desmet et al. |
| 2016/0042660 A1 | 2/2016 | Radovcic |
| 2016/0051184 A1 | 2/2016 | Wisbey et al. |
| 2016/0058245 A1 | 3/2016 | Smith et al. |
| 2016/0059077 A1 | 3/2016 | Paul et al. |
| 2016/0059078 A1 | 3/2016 | Liao |
| 2016/0059079 A1 | 3/2016 | Watterson |
| 2016/0061300 A1 | 3/2016 | Aoto et al. |
| 2016/0063615 A1 | 3/2016 | Watterson |
| 2016/0066818 A1 | 3/2016 | Cowley et al. |
| 2016/0067537 A1 | 3/2016 | Bayerlein et al. |
| 2016/0071014 A1 | 3/2016 | Brand et al. |
| 2016/0074701 A1 | 3/2016 | Wiener |
| 2016/0074705 A1 | 3/2016 | Wiener |
| 2016/0077547 A1 | 3/2016 | Aimone et al. |
| 2016/0089569 A1 | 3/2016 | Blahnik |
| 2016/0107029 A1 | 4/2016 | Kim et al. |
| 2016/0112684 A1 | 4/2016 | Connor |
| 2016/0114211 A1 | 4/2016 | Schmidt |
| 2016/0121161 A1 | 5/2016 | Mountain |
| 2016/0136483 A1 | 5/2016 | Reich |
| 2016/0148535 A1 | 5/2016 | Ashby |
| 2016/0148536 A1 | 5/2016 | Ashby |
| 2016/0151603 A1 | 6/2016 | Shouldice et al. |
| 2016/0157740 A1 | 6/2016 | Kampman et al. |
| 2016/0166881 A1 | 6/2016 | Ridgel et al. |
| 2016/0171110 A1 | 6/2016 | Gao et al. |
| 2016/0184635 A1 | 6/2016 | Kwon |
| 2016/0206922 A1 | 7/2016 | Dalebout et al. |
| 2016/0219968 A1 | 8/2016 | Martin |
| 2016/0232811 A9 | 8/2016 | Connor |
| 2016/0249365 A1 | 8/2016 | Harel |
| 2016/0250519 A1 | 9/2016 | Watterson |
| 2016/0253918 A1 | 9/2016 | Watterson |
| 2016/0256082 A1 | 9/2016 | Ely et al. |
| 2016/0256745 A1 | 9/2016 | Brammer |
| 2016/0263426 A1 | 9/2016 | Mueller et al. |
| 2016/0279462 A1 | 9/2016 | Sutherland |
| 2016/0279470 A1 | 9/2016 | Hampton |
| 2016/0296053 A1 | 10/2016 | Bakhsh |
| 2016/0317866 A1 | 11/2016 | Fung |
| 2016/0321932 A1 | 11/2016 | Mitchell |
| 2016/0346598 A1 | 12/2016 | Manzke et al. |
| 2016/0346616 A1 | 12/2016 | Kirby et al. |
| 2016/0351070 A1 | 12/2016 | Aillon-Sohl |
| 2016/0367857 A1 | 12/2016 | Aragones et al. |
| 2016/0371998 A1 | 12/2016 | Fazeel |
| 2016/0375307 A1 | 12/2016 | Durham |
| 2016/0375308 A1 | 12/2016 | Anderson |
| 2017/0007886 A1 | 1/2017 | Alessandri |
| 2017/0011210 A1 | 1/2017 | Cheong et al. |
| 2017/0014661 A1 | 1/2017 | Lin |
| 2017/0020440 A1 | 1/2017 | Flitsch et al. |
| 2017/0036106 A1 | 2/2017 | Stechschulte et al. |
| 2017/0050069 A1 | 2/2017 | Ky |
| 2017/0050102 A1 | 2/2017 | Kelly |
| 2017/0056726 A1 | 3/2017 | Dalebout et al. |
| 2017/0063567 A1 | 3/2017 | Tanaka et al. |
| 2017/0065187 A1 | 3/2017 | Hsieh et al. |
| 2017/0065947 A1 | 3/2017 | Haney et al. |
| 2017/0082983 A1 | 3/2017 | Katzer et al. |
| 2017/0093451 A1 | 3/2017 | Chen et al. |
| 2017/0097717 A1 | 4/2017 | Anisetti et al. |
| 2017/0100636 A1 | 4/2017 | Umetsu et al. |
| 2017/0104425 A1 | 4/2017 | Meloche |
| 2017/0128783 A1 | 5/2017 | Hasegawa et al. |
| 2017/0128784 A1 | 5/2017 | Molins et al. |
| 2017/0136293 A1 | 5/2017 | Caccia |
| 2017/0136301 A1 | 5/2017 | Cameron |

(56) References Cited

U.S. PATENT DOCUMENTS

| | | |
|---|---|---|
| 2017/0136339 A1 | 5/2017 | Habiche |
| 2017/0144051 A1 | 5/2017 | Oleson et al. |
| 2017/0164876 A1 | 6/2017 | Hyde et al. |
| 2017/0180535 A1 | 6/2017 | Esenwein et al. |
| 2017/0193578 A1 | 7/2017 | Watterson |
| 2017/0225034 A1 | 8/2017 | Kass et al. |
| 2017/0235922 A1 | 8/2017 | Weast et al. |
| 2017/0252623 A1 | 9/2017 | Sharifi |
| 2017/0252641 A1 | 9/2017 | Morimura et al. |
| 2017/0266503 A1 | 9/2017 | Watterson et al. |
| 2017/0266532 A1 | 9/2017 | Watterson |
| 2017/0266533 A1 | 9/2017 | Dalebout |
| 2017/0266534 A1 | 9/2017 | Watterson |
| 2017/0270820 A1 | 9/2017 | Ashby |
| 2017/0274237 A1 | 9/2017 | Chang |
| 2017/0311817 A9 | 11/2017 | Hsieh et al. |
| 2017/0333755 A1 | 11/2017 | Rider |
| 2017/0354846 A1 | 12/2017 | Von Rueckmann |
| 2017/0364661 A1 | 12/2017 | Hamilton, II et al. |
| 2017/0365048 A1 | 12/2017 | Hamilton, II et al. |
| 2018/0008865 A9 | 1/2018 | Lannon et al. |
| 2018/0036572 A1 | 2/2018 | Hsu |
| 2018/0056111 A1 | 3/2018 | Chiang et al. |
| 2018/0084817 A1 | 3/2018 | Capell et al. |
| 2018/0085630 A1 | 3/2018 | Capell et al. |
| 2018/0085654 A1 | 3/2018 | Black et al. |
| 2018/0089396 A1 | 3/2018 | Capell et al. |
| 2018/0092603 A1 | 4/2018 | Duan et al. |
| 2018/0099116 A1 | 4/2018 | Ashby |
| 2018/0099184 A1 | 4/2018 | Eder |
| 2018/0099205 A1 | 4/2018 | Watterson |
| 2018/0109838 A1 | 4/2018 | Garcia et al. |
| 2018/0111034 A1 | 4/2018 | Watterson |
| 2018/0116599 A1 | 5/2018 | Bastide et al. |
| 2018/0117383 A1 | 5/2018 | Workman |
| 2018/0154206 A1 | 6/2018 | Kim |

FOREIGN PATENT DOCUMENTS

| | | |
|---|---|---|
| KR | 10-2016-0063126 | 6/2016 |
| WO | 2015021289 | 2/2015 |

OTHER PUBLICATIONS

English Translation of Abstract of KR10-2016-0063126 dated Jun. 3, 2016.

English Translation of Abstract of KR10-2016-0054325 dated May 16, 2016.

About Me

1. When's your birthday? [mm/dd/yy] — 212
2. What's your height? ☐ Feet ☐ Inches — 214
3. What's your sex? ☐ Male ☐ Female — 216
4. What's your current weight? [____] ○ lbs ○ kg — 218
5. What's your goal weight? [____] ○ lbs ○ kg — 220

*FIG. 2A*

CUSTOMIZING RECIPE RECOMMENDATIONS

RELATED APPLICATIONS

This application claims priority to U.S. patent application Ser. No. 62/400,773 titled "Customizing Recipe Recommendations" and filed on 28 Sep. 2016, which application is herein incorporated by reference for all that it discloses.

BACKGROUND

Recipes for nutritious meals are used by many consumers in an effort to achieve a healthy diet. There are perhaps millions or even billions of different recipes available in various publications such as recipe books, magazines, health books, and online recipe databases.

One common problem faced by consumers of recipes is selecting an appropriate recipe from among the overwhelming number of choices available. One way a consumer may deal with this problem is to consult with a dietitian, who may make a recommendation of one or more recipes based on an analysis of the consumer's preferences and healthy and unhealthy habits. However, such a consultation can be expensive, time consuming, and subjective, and may also be unhelpful due to the consumer providing subjective and inaccurate information to the dietitian, given that consumers notoriously overestimate their healthy habits and underestimate their unhealthy habits.

SUMMARY

In one aspect of the disclosure, a method for customizing recipe recommendations may include receiving a target number of calories for a user, receiving physical movement data of the user from one or more electronic sensors configured to directly measure physical movement of the user, analyzing the received physical movement data, determining one or more physical movement parameters based on the analysis of the received physical movement data, determining the recentness of each of the recipes being recommended or logged to the user, assigning a weight to each of the recipes based on the received target number of calories for the user, the determined one or more physical movement parameters, and the determined recentness of the recipe being recommended or logged to the user, ranking the recipes based on their assigned weights, and generating a custom recipe recommendation for the user based on the ranking of the recipes.

Another aspect of the disclosure may include any combination of the above-mentioned features and may further include the determined one or more physical movement parameters including number of calories burned by the user.

Another aspect of the disclosure may include any combination of the above-mentioned features and may further include the one or more electronic sensors including a wearable electronic sensor configured to be worn on a wrist of the user.

Another aspect of the disclosure may include any combination of the above-mentioned features and may further include the one or more electronic sensors including an exercise machine electronic sensor.

Another aspect of the disclosure may include any combination of the above-mentioned features and may further include the one or more electronic sensors including a sleep electronic sensor configured to be positioned in a bed of the user.

Another aspect of the disclosure may include any combination of the above-mentioned features and may further include the determined one or more physical movement parameters including a sleep quality experienced by the user.

Another aspect of the disclosure may include any combination of the above-mentioned features and may further include the method further including receiving a cuisine preference of the user and the assigning of the weight to each of the recipes being further based on the received cuisine preference of the user.

Another aspect of the disclosure may include any combination of the above-mentioned features and may further include the method further including receiving a diet preference of the user and the assigning of the weight to each of the recipes being further based on the received diet preference of the user.

Another aspect of the disclosure may include any combination of the above-mentioned features and may further include the method further including receiving an allergy status of the user and the assigning of the weight to each of the recipes being further based on the received allergy status of the user.

Another aspect of the disclosure may include any combination of the above-mentioned features and may further include the method further including receiving a meat preference of the user and the assigning of the weight to each of the recipes being further based on the received meat preference of the user.

Another aspect of the disclosure may include any combination of the above-mentioned features and may further include one or more non-transitory computer-readable media storing one or more programs that are configured, when executed, to cause one or more processors to perform the method for customizing recipe recommendations.

BRIEF DESCRIPTION OF THE DRAWINGS

The accompanying drawings illustrate various embodiments of the present method and system and are a part of the specification. The illustrated embodiments are merely examples of the present system and method and do not limit the scope thereof.

FIGS. 2A-2B are example webpages of an example website that may be employed in connection with the example health system of FIG. 1.

Throughout the drawings, identical reference numbers designate similar, but not necessarily identical, elements.

DETAILED DESCRIPTION

Methods for customizing recipe recommendations are disclosed herein. Specifically, the present methods generate custom recipe recommendations for users based on various data that is received or determined. For example, the received data may include a target number of calories for a user and physical movement data of the user. The received physical movement data may be received from one or more electronic sensors configured to directly measure physical movement of the user. This received physical movement data may then be analyzed and then one or more physical movement parameters may be determined based on the analysis of the received physical movement data. Further, the recentness of each of the recipes being recommended or logged to the user may be determined. A weight may then be assigned to each of the recipes based on the target number of calories for the user, the determined one or more physical movement parameters, and the determined recentness of the recipe being recommended or logged to the user. The recipes may then be ranked based on their assigned weights. Finally, the custom recipe recommendation for the user may be generated based on the ranking of the recipes. The methods for customizing recipe recommendations are described in detail below.

Figure 1:
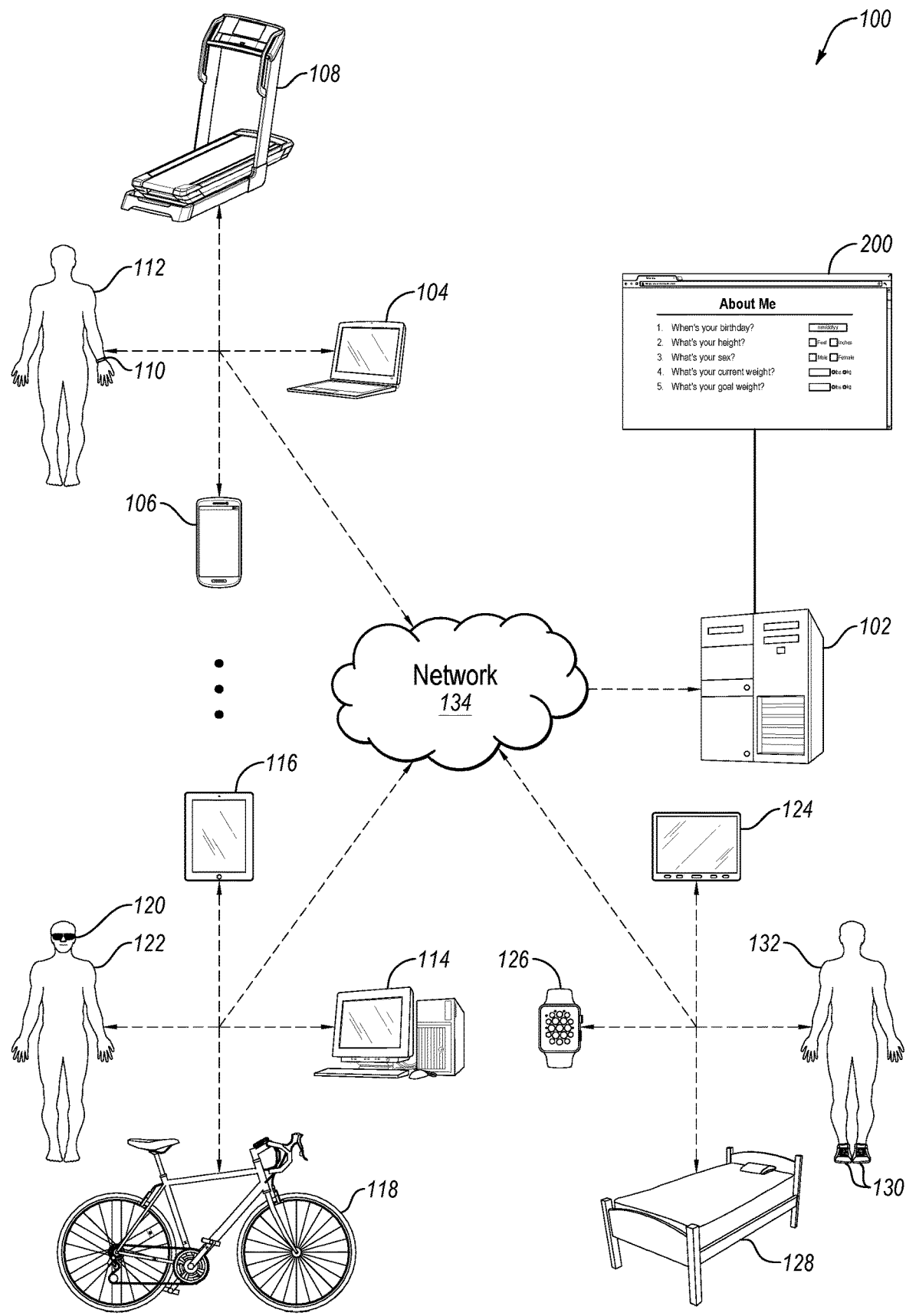
FIG. 1 is a diagram of an example health system.

FIG. 1 is a diagram of an example health system 100. The system 100 may include a server 102 that hosts a website 200. The system 100 may also include a laptop computer 104, a smartphone 106, a treadmill 108, and an activity tracker watch 110 configured to be worn on the wrist of a first user 112. The system 100 may further include a desktop computer 114, a tablet 116, a bicycle 118, and smart glasses 120 configured to be worn by a second user 122. The system 100 may also include a smart panel 124 of a smart home network, a smart watch 126, a smart bed 128, and smart shoes 130 configured to be worn on the feet of a third user 132.

As disclosed in FIG. 1, each of the computing devices in the system 100 may be configured to communicate with one another wirelessly, either locally or remotely via a network 134. In particular, the activity tracker watch 110 worn by the first user 112 may include an electronic sensor, such as an accelerometer, that is configured to directly measure physical movement of the first user 112, such as the number of steps taken by the first user 112 or tracking movement of the first user 112 while in bed, resulting in physical movement data. Similarly, the treadmill 108 may include multiple electronic sensors, such as an odometer, a tilt sensor, and a resistance sensor, that are configured to directly measure physical movement of the first user 112, such as the simulated distance run by the first user 112 on the treadmill 108, the incline while running, and the amount of effort expended by the first user 112 on the treadmill 108, resulting in physical movement data. The physical movement data from the activity tracker watch 110 and the treadmill 108 may be sent to, and received by, the laptop computer 104, the smartphone 106, or the server 102, or some combination thereof. A software application running on the laptop computer 104, the smartphone 106, or the server 102, or some combination thereof, may then be configured to analyze the physical movement data and then determine, based on the analysis of the physical movement data, one or more physical movement parameters. These one or more physical movement parameters may include a number of calories burned by the first user 112. After the software application has determined the one or more physical movement parameters, the software application may then generate a custom recipe recommendation for the first user 112 based at least in part on the one or more physical movement parameters.

Further, the smart glasses 120 worn by the second user 122 may include multiple electronic sensors, such as a GPS receiver and a video camera, that are configured to directly measure physical movement of the second user 122, such as the distance traveled and the amount of head movement by the second user 122, resulting in physical movement data. Similarly, the bicycle 118 may include an electronic sensor, such as a cadence sensor, that is configured to directly measure physical movement of the second user 122, such as the number of pedal strokes performed by the second user 122 on the bicycle 118, resulting in physical movement data. The physical movement data from the smart glasses 120 and the bicycle 118 may be sent to, and received by, the desktop computer 114, the tablet 116, or the server 102, or some combination thereof. A software application running on the desktop computer 114, the tablet 116, or the server 102, or some combination thereof, may then be configured to analyze the physical movement data and then determine, based on the analysis of the physical movement data, one or more physical movement parameters. After the software application has determined the one or more physical movement parameters, the software application may then generate a custom recipe recommendation for the second user 122 based at least in part on the one or more physical movement parameters.

Also, the smart shoes 130 worn by the third user 132 may include multiple electronic sensors, such as insole-mounted motion sensors, that are configured to directly measure physical movement of the third user 132, such as movement of the feet of the third user 132, resulting in physical movement data. Similarly, the smart bed 128 may include an electronic sensor, such as a sleep sensor positioned in the smart bed 128, that is configured to directly measure physical movement of the third user 132, such as tracking movement of the third user 132 while in the smart bed 128, resulting in physical movement data. Further, the sleep sensor may be configured to track the temperature of the room while the third user 132 is in the smart bed 128. The physical movement data from the smart shoes 130 and the smart bed 128 may be sent to, and received by, the smart panel 124, the smart watch 126, or the server 102, or some combination thereof. A software application running on the smart panel 124, the smart watch 126, or the server 102, or some combination thereof, may then be configured to analyze the physical movement data and then determine, based on the analysis of the physical movement data, one or more physical movement parameters. These one or more physical movement parameters may include a sleep quality experienced by the third user 132. After the software application has determined the one or more physical movement parameters, the software application may then generate a custom recipe recommendation for the third user 132 based at least in part on the one or more physical movement parameters.

Figure 2B:
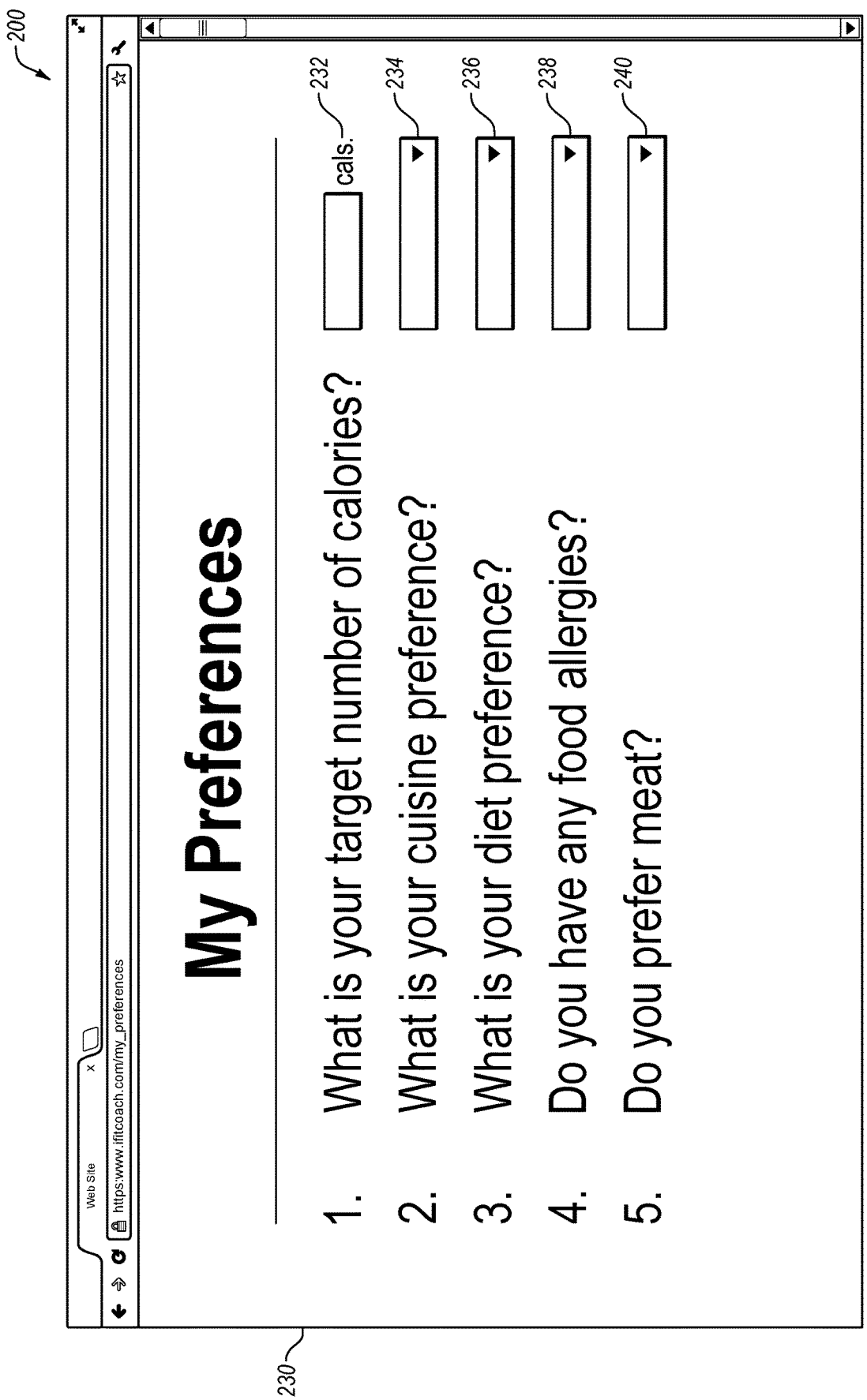

FIGS. 2A-2B are example webpages of the website 200 that may be employed in connection with the system 100 of FIG. 1.

As disclosed in FIG. 2A, a first webpage 210 of the website 200 may be configured to be presented to a user in order to receive data about the user. In particular, the first webpage 210 may be configured to receive the user's birthday, height, sex, current weight, and weight loss goal in data entry fields 212-220, respectively.

As disclosed in FIG. 2B, a second webpage 230 of the website 200 may be configured to be presented to a user in order to receive data regarding the preferences of the user. In particular, the second webpage 230 may be configured to receive the user's target number of calories, cuisine preference, diet preference, allergy status, and meat preference in data entry fields 232-240, respectively.

Figure 3A:
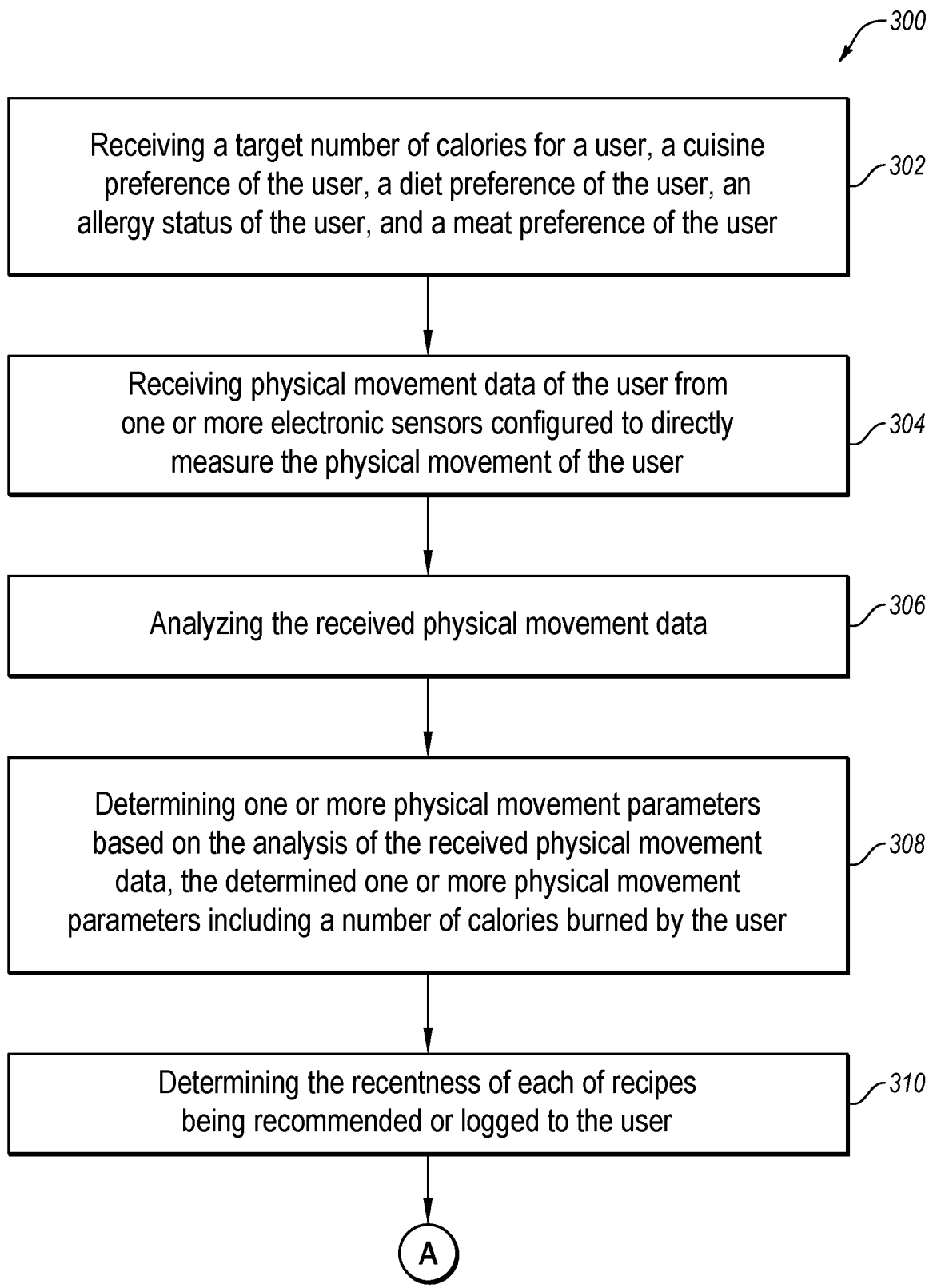
FIGS. 3A-3B are a diagram of an example method for customizing recipe recommendations.
Figure 3B:
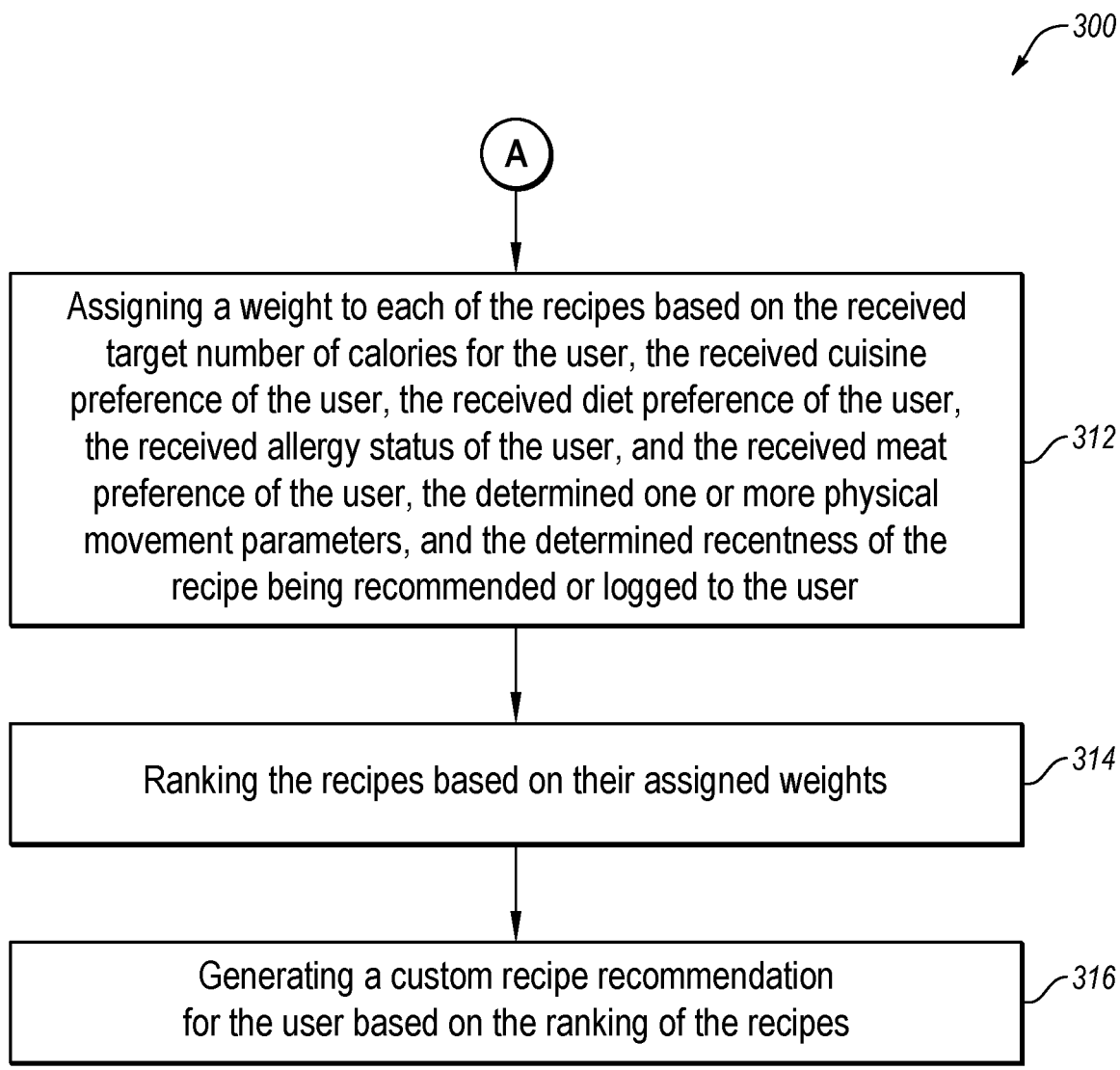

FIGS. 3A-3B are a diagram of an example method 300 for customizing recipe recommendations. The method 300 may be performed, for example, by a software application being executed on the server 102, the laptop computer 104, the smartphone 106, the desktop computer 114, the tablet 116, the smart panel 124, or the smart watch 126, or some combination therefore, of FIG. 1.

The method 300 may include receiving, at 302, a target number of calories for a user, a cuisine preference of the user, a diet preference of the user, an allergy status of the user, and a meat preference of the user.

The method 300 may include receiving, at 304, physical movement data of the user from one or more electronic sensors configured to directly measure physical movement of the user.

The method 300 may include analyzing, at 306, the received physical movement data.

The method 300 may include determining, at 308, one or more physical movement parameters based on the analysis of the physical movement data. The determined one or more physical movement parameters may include a number of calories burned by the user.

The method 300 may include determining, at 310, the recentness of each of the recipes being recommended or logged to the user.

The method 300 may include assigning, at 312, a weight to each of the recipes based on the received target number of calories for the user, the received cuisine preference of the user, the received diet preference of the user, the received allergy status of the user, and the received meat preference of the user, the determined one or more physical movement parameters, and the determined recentness of the recipe being recommended or logged to the user.

The method 300 may include ranking, at 314, the recipes based on their assigned weights.

The method 300 may include generating, at 316, a custom recipe recommendation for the user based on the ranking of the recipes.

INDUSTRIAL APPLICABILITY

In general, the methods for customizing recipe recommendations disclosed above generate custom recipe recommendations for users based on various data that is received or determined. Various modifications to the methods disclosed above will now be disclosed.

The software application disclosed herein that is configured to receive data, analyze data, make determinations with respect to data, and generate custom recipe recommendations may be configured to be executed on one or more computing devices. For example, the computing devices may include, but are not limited to, an application or app that is executed on a smartphone, a smart watch, a smart panel of a smart home network, an exercise machine, a laptop computer, a tablet, or a desktop computer. Further, the software application may be distributed across two or more computing devices that communicate with each other over a wired or wireless network.

Further, the software application disclosed herein may be configured to execute according to one or more formulas. For example, the weight assigned to each recipe by the software application disclosed herein may be calculated according to the following formula:

$$A*B*C*D*E*F*G*H = \text{Recipe Weight}$$

where:
 A=Recently logged recipe weight
 B=Recently recommended recipe weight
 C=Target calorie weight
 D=Cuisine weight
 E=Diet weight
 F=Allergen weight
 G=Preferred meat weight
 H=Poor sleep adaptation weight Using this formula, a weight=1 may be considered neutral, a weight>1 may be preferred, a 0<weight<1 may not be preferred but allowed, and a weight=0 may not be allowed and never recommended. Since the weights for all different preference settings in this formula are multiplied together for each recipe, if a recipe has a total weight of 1.2, it is twice as likely to be recommended as a recipe that has a weight of 0.6. For example, where a recipe has not been logged in the past 10 days (1), but was recommended four days ago (0.8704), falls within the allowed calorie range (1), is a preferred cuisine type selected by the user (1.5), falls in the diet the user has selected their goal (1), has no allergens (1), uses a meat that is not preferred (0.2), and the user had a good night's rest (1), the weight for the recipe will be 1*0.8704*1*1.5*1*1*0.2*1=0.26112. With a weight of 0.26112, this weight is far less likely to be recommended than average. Calculations of each of the individual weights A-H will now be described.

The following formula may be used to calculate the weight A, which affects how often a recipe will be recommended again after it has been logged.

$$1-(0.85^{\wedge}(t-1))=A$$

This formula assumes that that t represents a number of days, with t=0 on the day the recipe is logged, and this formula is only employed where t≤10. For example, if a user logged the recipe six days ago, the weight A will be 1−(0.85^(6−1))=0.5563. Once t=10, the weight A=1.

The following formula may be used to calculate the weight B, which affects how often a recipe will be recommended again after it has been recommended but not logged.

$$1-(0.6^{\wedge}t)=B$$

This formula assumes that t represents a number of days, t=0 on the day the recipe is recommended but not logged, and this formula is only employed where t≤5. For example, if a user was recommended the recipe three days ago but the recipe was not logged, the weight B will be 1−(0.85^3) =0.784. Once t=5, the weight B=1.

The weight C may affect how often a recipe will be recommended based on a target calorie intake. For example, if a recipe is more or less than the target calorie intake by 50 calories, the weight C=0, otherwise the weight C=1. For example, if the target number of calories for the user is 450 calories, recipes from 400 to 500 calories will have a weight C =1, and all other recipes will have a weight C=0.

The weight D may affect how often a recipe will be recommended based on if the recipe is the preferred cuisine type of a user. For example, the weight D=1.5 if the recipe falls within the user's preferred cuisine, and the weight D=1 if the recipe falls outside the user's preferred cuisine.

The weight E may affect whether a recipe will be recommended based on if the recipe fits within a user's specified diet. For example, if no diet is selected by the user, the weight E=1 for all recipes. If a diet is selected by the user, the weight E=1 if the recipe falls within the selected diet and the weight E=0 if the recipe does not fall within the selected diet.

The weight F may affect whether a recipe will be recommended based on if the recipe includes foods to which the user is allergic. For example, the weight F=1 if the recipe does not include any foods to which the user is allergic and the weight F=0 if the recipe does include any food to which the user is allergic.

The weight G may affect how often a recipe will be recommended based on if the recipe includes meats that the user prefers. For example, if no meat preference is selected by the user, the weight G=1 for all recipes. If a meat preference is selected by the user, the weight G=1 if the recipe includes meats the user prefers and the weight G=0.2 if the recipe includes other meats.

The weight H may affect how often a recipe will be recommended based on the user's sleep quality during the night prior to the day of the recipe recommendation. For example, if the user had high quality sleep, the weight H=1 for all recipes. If the user had poor quality sleep, the weight H=2.0 if the recipe has a fiber content of more than 6 grams and/or the recipe has 30% or more of its calories from protein, otherwise the recipe receives a weight H=0.5. A poor quality sleep may be a sleep with a score less than or equal to 60 or a sleep time of less than six hours.

It is understood that the various weights A-H employed in the Recipe Weight formula above may be combined in a variety of ways including eliminating one or more of the weights A-H from the Recipe Weight formula.

Further, the software application disclosed herein may include the use of a special-purpose or general-purpose computer, including various computer hardware or software. The software application may be implemented using non-transitory computer-readable media for carrying or having computer-executable instructions or data structures stored thereon. Such computer-readable media may be any available media that may be accessed by a general-purpose or special-purpose computer. By way of example, and not limitation, such computer-readable media may include non-transitory computer-readable storage media including RAM, ROM, EEPROM, CD-ROM or other optical disk storage, magnetic disk storage or other magnetic storage devices, or any other storage medium which may be used to carry or store one or more desired programs having program code in the form of computer-executable instructions or data structures and which may be accessed and executed by a general-purpose computer, special-purpose computer, or virtual computer such as a virtual machine. Combinations of the above may also be included within the scope of computer-readable media. Computer-executable instructions comprise, for example, instructions and data which, when executed by one or more processors, cause a general-purpose computer, special-purpose computer, or virtual computer such as a virtual machine to perform a certain method, function, or group of methods or functions.

The communication between computing devices disclosed herein may be accomplished over any wired or wireless communication network including, but not limited to, a Local Area Network (LAN), a Wide Area Network (WAN), a Wireless Application Protocol (WAP) network, a Bluetooth network, an ANT network, or an Internet Protocol (IP) network such as the Internet, or some combination thereof.

The receipt of data from a user disclosed herein in connection with various webpages of a website may additionally or alternatively be accomplished using other data gathering technologies including, but not limited to, receiving data from a user via data entry interfaces of an app on a smartphone or gathering data regarding a user by accessing databases that already store the desired data such as registration databases of an app server or a website server, or some combination thereof. Further, the receipt of data from a user disclosed herein in connection with various webpages of a website is example data only, and other types and specificity of data may additionally or alternatively be received from a user.

The electronic sensors disclosed herein that are configured to directly measure physical movement of the user may include both portable as well as stationary electronic sensors. Portable electronic sensors may include, but are not limited to, electronic sensors built into smart watches, fitness trackers, sport watches, head mounted displays, smart clothing, smart jewelry, vehicles, sports equipment, or implantables configured to be implanted in the human body, or some combination thereof. Stationary electronic sensors may include, but are not limited to, sensors built into exercise machines, furniture, beds or bedding (to measure physical movement while in bed and/or while asleep), flooring, walls, ceilings, doorways, or fixtures along paths and roadways, or some combination thereof. These sensors configured to measure physical movement of the user may include, but are not limited to, sensors that measure physical movement using infrared, microwave, ultrasonic, tomographic, GPS, accelerometer, gyroscope, odometer, tilt, speedometer, piezoelectric, or video technologies, or some combination thereof.

The use of one or more electronic sensors in the example methods disclosed herein may solve the problem of a subjective recommendation from a dietitian that is based on subjective information provided by a user. In particular, since a dietitian is a human being, the dietitian is inherently biased and any recommendations are necessarily subjective instead of objective. Further, there are severe limitations to what types of information, and accuracy of information, that a human user can gather and convey to the human dietitian. The use of one or more electronic sensors in the example methods disclosed herein may solve these problems by using highly sophisticated and specialized electronic sensors that are configured to objectively and directly measure physical movement of the user resulting in objective physical movement data and then sending that objective physical movement data to the objective software application disclosed herein instead of a subjective human dietitian. These electronic sensors may have specific tolerances and may enable a single computing device to measure multiple users in multiple remote locations. None of these capabilities are available to a human user absent these highly sophisticated and specialized electronic sensors. These highly sophisticated and specialized electronic sensors may therefore solve the problems with the prior art method by objectively and accurately measuring physical movement of the user instead of relying on subjective and biased observations of a user.

Further, the example methods disclosed herein are not directed to an abstract idea because they solve a technical problem using highly sophisticated and specialized electronic sensors. The data generated by these electronic sensors simply has no equivalent to pre-electronic sensor, manual paper-and-pencil data.

Also, the example methods disclosed herein may improve the technical field of automated recipe recommendations. For example, the technical field of automated recipe recommendations may be improved by the example methods disclosed herein at least because the prior art method did not enable the automatic measurement of the physical movement of a user and the automatic sending of physical movement data to a software application capable of customizing a recipe recommendation based on an automatic analysis and determination of parameters from the received physical movement data.

What is claimed is:

1. A method for customizing recipe recommendations, the method comprising:
   receiving, at a server, a target number of calories for a user, entered on a webpage of a website hosted at the server;
   receiving, at the server, physical movement data of the user from one or more electronic sensors configured to directly measure physical movement of the user and configured to wirelessly transmit the physical movement data to the server over a network;
analyzing, at the server, the received physical movement data;
determining, at the server, one or more physical movement parameters based on the analysis of the received physical movement data;
determining, at the server, a recentness of each of multiple recipes being recommended or logged to the user;
assigning, at the server, a weight to each of the recipes based on the received target number of calories for the user, the determined one or more physical movement parameters, and the determined recentness of the recipe being recommended or logged to the user;
ranking, at the server, the recipes based on their assigned weights; and
generating, at the server, a custom recipe recommendation for the user based on the ranking of the recipes.

2. The method of claim 1, wherein the determined one or more physical movement parameters include a number of calories burned by the user.

3. The method of claim 2, wherein the one or more electronic sensors are included in a wearable activity tracker configured to be worn on a wrist of the user.

4. The method of claim 2, wherein the one or more electronic sensors includes an exercise machine electronic sensor.

5. The method of claim 1, wherein the one or more electronic sensors includes a sleep electronic sensor configured to be positioned in a bed of the user.

6. The method of claim 5, wherein the determined one or more physical movement parameters include a sleep quality experienced by the user.

7. The method of claim 1, wherein:
the method further comprises receiving, via the webpage of the website hosted at the server, a cuisine preference of the user; and
the assigning, at the server, of the weight to each of the recipes is further based on the received cuisine preference of the user.

8. The method of claim 1, wherein:
the method further comprises receiving, via the webpage of the website hosted at the server, a diet preference of the user; and
the assigning, at the server, of the weight to each of the recipes is further based on the received diet preference of the user.

9. The method of claim 1, wherein:
the method further comprises receiving, via the webpage of the website hosted at the server, an allergy status of the user; and
the assigning, at the server, of the weight to each of the recipes is further based on the received allergy status of the user.

10. The method of claim 1, wherein:
the method further comprises receiving, via the webpage of the website hosted at the server, a meat preference of the user; and
the assigning, at the server, of the weight to each of the recipes is further based on the received meat preference of the user.

11. A method for customizing recipe recommendations, the method comprising:
receiving, at a server, a target number of calories for a user, a cuisine preference of the user, a diet preference of the user, an allergy status of the user, and a meat preference of the user, entered on a webpage of a website hosted at the server;
receiving, at the server, physical movement data of the user from one or more electronic sensors configured to directly measure physical movement of the user and configured to wirelessly transmit the physical movement data to the server over a network;
analyzing, at the server, the received physical movement data;
determining, at the server, one or more physical movement parameters based on the analysis of the received physical movement data, the determined one or more physical movement parameters including a number of calories burned by the user;
determining, at the server, a recentness of each of multiple recipes being recommended or logged to the user;
assigning, at the server, a weight to each of the recipes based on the received target number of calories for the user, the received cuisine preference of the user, the received diet preference of the user, the received allergy status of the user, and the received meat preference of the user, the determined one or more physical movement parameters, and the determined recentness of the recipe being recommended or logged to the user;
ranking, at the server, the recipes based on their assigned weights; and
generating, at the server, a custom recipe recommendation for the user based on the ranking of the recipes.

12. The method of claim 11, wherein the one or more electronic sensors are included in a wearable activity tracker configured to be worn on a wrist of the user and configured to count the steps of the user.

13. The method of claim 11, wherein the one or more electronic sensors includes an exercise machine electronic sensor configured to track an amount of effort expended by the user on the exercise machine.

14. The method of claim 11, wherein the one or more electronic sensors includes a sleep electronic sensor configured to be positioned in a bed of the user and configured to track movement of the user while in the bed.

15. The method of claim 14, wherein the determined one or more physical movement parameters include a sleep quality experienced by the user.

16. One or more non-transitory computer-readable media storing one or more programs that are configured, when executed, to cause one or more processors to perform a method for customizing recipe recommendations, the method comprising:
receiving, at a server, a target number of calories for a user, a cuisine preference of the user, a diet preference of the user, an allergy status of the user, and a meat preference of the user, entered on a webpage of a website hosted at the server;
receiving, at the server, physical movement data of the user from one or more electronic sensors, the one or more electronic sensors configured to directly measure physical movement of the user and configured to wirelessly transmit the physical movement data to the server over a network;
analyzing, at the server, the physical movement data;
determining, at the server, one or more physical movement parameters based on the analysis of the physical movement data, the determined one or more physical movement parameters including a number of calories burned by the user;
determining, at the server, a recentness of each of multiple recipes being recommended or logged to the user;

assigning, at the server, a weight to each of the recipes based on the received target number of calories for the user, the received cuisine preference of the user, the received diet preference of the user, the received allergy status of the user, and the received meat preference of the user, the determined one or more physical movement parameters, and the determined recentness of the recipe being recommended or logged to the user;

ranking, at the server, the recipes based on their assigned weights; and generating, at the server, a custom recipe recommendation for the user based on the ranking of the recipes.

17. The one or more non-transitory computer-readable media of claim 16, wherein the one or more electronic sensors are included in a wearable activity tracker configured to be worn on a wrist of the user and configured to count the steps of the user and configured to track movement of the user while in bed.

18. The one or more non-transitory computer-readable media of claim 16, wherein the one or more electronic sensors includes an exercise machine electronic sensor configured to track an amount of effort expended by the user on the exercise machine and configured to track a simulated distance traveled by the user on the exercise machine.

19. The one or more non-transitory computer-readable media of claim 16, wherein the one or more electronic sensors includes a sleep electronic sensor configured to be positioned in a bed in a room of the user and configured to track movement of the user while in the bed and track a temperature of the room while the user is in the bed.

20. The one or more non-transitory computer-readable media of claim 19, wherein the determined one or more physical movement parameters include a sleep quality experienced by the user.

* * * * *